US012606804B2

(12) United States Patent
Moser et al.

(10) Patent No.: US 12,606,804 B2
(45) Date of Patent: Apr. 21, 2026

(54) INFLUENZA VIRUS BACKBONE

(71) Applicant: FluGen, Inc., Madison, WI (US)

(72) Inventors: Michael J. Moser, Madison, WI (US);
Yasuko Hatta, Madison, WI (US);
Pamuk Bilsel, Madison, WI (US);
Lindsay Hill-Batorski, Lodi, WI (US)

(73) Assignee: FluGen, Inc., Madison, WI (US)

( * ) Notice: Subject to any disclaimer, the term of this
patent is extended or adjusted under 35
U.S.C. 154(b) by 589 days.

(21) Appl. No.: 18/017,374

(22) PCT Filed: Jul. 21, 2021

(86) PCT No.: PCT/US2021/042572
§ 371 (c)(1),
(2) Date: Jan. 20, 2023

(87) PCT Pub. No.: WO2022/020469
PCT Pub. Date: Jan. 27, 2022

(65) Prior Publication Data
US 2023/0295582 A1     Sep. 21, 2023

Related U.S. Application Data

(60) Provisional application No. 63/054,676, filed on Jul.
21, 2020.

(51) Int. Cl.
*C12N 7/00*     (2006.01)
*A61K 39/12*     (2006.01)
*C07K 14/11*     (2006.01)
*A61K 39/00*     (2006.01)

(52) U.S. Cl.
CPC ............... *C12N 7/00* (2013.01); *A61K 39/12*
(2013.01); *C07K 14/11* (2013.01); *A61K*
*2039/522* (2013.01); *C12N 2760/16121*
(2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 6,270,958 B1 | 8/2001 | Olivo et al. | |
| 6,544,785 B1 | 4/2003 | Palese et al. | |
| 6,872,395 B2 | 3/2005 | Kawaoka | |
| 7,176,021 B2 | 2/2007 | Kawaoka | |
| 7,226,774 B2 | 6/2007 | Kawaoka | |
| 7,276,356 B1 | 10/2007 | Palese et al. | |
| 7,312,064 B2 | 12/2007 | Hoffmann | |
| 7,384,774 B2 | 6/2008 | Palese et al. | |
| 7,459,162 B2 | 12/2008 | Yang et al. | |
| 7,510,719 B2 | 3/2009 | Dang et al. | |
| 7,566,458 B2 | 7/2009 | Yang et al. | |
| 7,585,657 B2 | 9/2009 | Kawaoka | |
| 7,588,769 B2 | 9/2009 | Kawaoka | |
| 7,723,094 B2 | 5/2010 | Kawaoka et al. | |

| | | | |
|---|---|---|---|
| 7,790,434 B2 | 9/2010 | Duke et al. | |
| 7,959,930 B2 | 6/2011 | De Wit et al. | |
| 7,968,101 B2 | 6/2011 | Kawaoka et al. | |
| 7,972,843 B2 | 7/2011 | Hoffmann | |
| 7,993,924 B2 | 8/2011 | Billeter et al. | |
| 8,012,736 B2 | 9/2011 | Hoffman et al. | |
| 8,012,737 B2 | 9/2011 | Dang et al. | |
| 8,043,856 B2 | 10/2011 | Kawaoka et al. | |
| 8,048,430 B2 | 11/2011 | Yang et al. | |
| 8,057,806 B2 | 11/2011 | Kawaoka | |
| 8,163,523 B2 | 4/2012 | Bilsel et al. | |
| 8,202,726 B2 | 6/2012 | Liu et al. | |
| 8,288,145 B2 | 10/2012 | Röthl et al. | |
| 8,298,805 B2 | 10/2012 | Kawaoka | |
| 8,333,975 B2 | 12/2012 | Yang et al. | |
| 8,404,248 B2 | 3/2013 | Yang et al. | |
| 8,465,960 B2 | 6/2013 | Kawaoka et al. | |
| 8,475,806 B2 | 7/2013 | Kawaoka et al. | |
| 8,507,247 B2 | 8/2013 | Kawaoka et al. | |
| 8,574,593 B2 | 11/2013 | Yang et al. | |
| 8,592,196 B2 | 11/2013 | Kittel et al. | |
| 8,597,661 B2 | 12/2013 | Kawaoka et al. | |
| 8,673,613 B2 | 3/2014 | Jin et al. | |
| 8,679,819 B2 | 3/2014 | Kawaoka | |

(Continued)

FOREIGN PATENT DOCUMENTS

| CN | 102864127 A | 1/2013 |
|---|---|---|
| CN | 102864128 A | 1/2013 |

(Continued)

OTHER PUBLICATIONS

Clark, et al., "Functional Evolution of Influenza Virus NS1 Protein
in Currently Circulating Human 2009 Pandemic H1N1 Viruses,"
*Journal of Virology*, 91(17): 1-22 (Aug. 10, 2017).
Davis et al., "Identification of influenza A nucleoprotein body
domain residues essential for viral RNA expression expose antiviral
target," *Virology Journal*, 14(22): 1-13 (Feb. 7, 2017).
Globaldata Healthcare, "Influenza vaccine: FluGen has successful
Phase II trial for M2SR," Feb. 22. 2019, XP093027811, Retrieved
from the Internet Mar. 1, 2023 https://www.pharmaceutical-technology.
com/comment/flugen-successbrings-the-reality-of-universal-influenza-
vaccines-closer/.

(Continued)

*Primary Examiner* — Agnieszka Boesen
(74) *Attorney, Agent, or Firm* — Leydig, Voit & Mayer,
Ltd.

(57) ABSTRACT

The invention provides an influenza virus that demonstrates
enhanced growth in Vero cells. The influenza virus includes
PA, NP, and NS gene segments having selected nucleotides
and encoding proteins having amino acid sequences with
selected amino aids. The invention also provides a pharma-
ceutical formulation containing the influenza virus, as well
as a method of eliciting an immune response in a mammal
by administering the influenza virus to the mammal, and a
method for generating the influenza virus.

28 Claims, 27 Drawing Sheets
Specification includes a Sequence Listing.

(56)  References Cited

U.S. PATENT DOCUMENTS

| | | | |
|---|---|---|---|
| 8,685,410 B2 | 4/2014 | Yang et al. | |
| 8,691,239 B2 | 4/2014 | Yang et al. | |
| 8,715,940 B2 | 5/2014 | Kawaoka et al. | |
| 8,859,208 B2 | 10/2014 | Kawaoka et al. | |
| 8,877,209 B2 | 11/2014 | Kawaoka et al. | |
| 8,877,210 B2 | 11/2014 | Yang et al. | |
| 8,877,448 B2 | 11/2014 | Kawaoka et al. | |
| 8,883,479 B2 | 11/2014 | Krenn et al. | |
| 9,023,603 B2 | 5/2015 | Kawaoka et al. | |
| 9,068,986 B2 | 6/2015 | Jin et al. | |
| 9,085,753 B2 | 7/2015 | Liu et al. | |
| 9,101,653 B2 | 8/2015 | Kawaoka et al. | |
| 9,109,013 B2 | 8/2015 | Kawaoka et al. | |
| 9,119,810 B2 | 9/2015 | Montelione et al. | |
| 9,157,096 B2 | 10/2015 | Kawaoka et al. | |
| 9,254,318 B2 | 2/2016 | Kawaoka et al. | |
| 9,284,533 B2 | 3/2016 | Bilsel et al. | |
| 9,474,798 B2 | 10/2016 | Watanabe et al. | |
| 9,580,693 B2 | 2/2017 | Kawaoka et al. | |
| 9,732,313 B2 | 8/2017 | Hirschel et al. | |
| 9,757,446 B2 | 9/2017 | LeFebvre et al. | |
| 9,890,363 B2 | 2/2018 | Kawaoka et al. | |
| 9,919,042 B2 | 3/2018 | Bilsel et al. | |
| 9,919,043 B2 | 3/2018 | Bilsel et al. | |
| 9,926,535 B2 | 3/2018 | Kawaoka et al. | |
| 9,950,057 B2 | 4/2018 | Kawaoka et al. | |
| 10,022,434 B2 | 7/2018 | Weiner et al. | |
| 10,053,671 B2 | 8/2018 | Kawaoka et al. | |
| 10,059,925 B2 | 8/2018 | Kawaoka et al. | |
| 10,119,124 B2 | 11/2018 | Watanabe et al. | |
| 10,130,697 B2 | 11/2018 | Watanabe et al. | |
| 10,172,934 B2 | 1/2019 | Kawaoka et al. | |
| 10,246,686 B2 | 4/2019 | Kawaoka et al. | |
| 10,358,630 B2 | 7/2019 | Kawaoka et al. | |
| 10,494,613 B2 | 12/2019 | Kawaoka et al. | |
| 10,500,267 B2 | 12/2019 | LeFebvre et al. | |
| 10,513,692 B2 | 12/2019 | Kawaoka et al. | |
| 10,570,376 B2 | 2/2020 | Peterka et al. | |
| 10,633,422 B2 | 4/2020 | Kawaoka et al. | |
| 10,808,229 B2 | 10/2020 | Kawaoka et al. | |
| 11,007,262 B2 | 5/2021 | Watanabe et al. | |
| 11,046,934 B2 | 6/2021 | Kawaoka et al. | |
| 11,180,737 B2 | 11/2021 | Kawaoka et al. | |
| 11,197,925 B2 * | 12/2021 | Kawaoka | A61P 31/16 |
| 2003/0035814 A1 | 2/2003 | Kawaoka et al. | |
| 2004/0180058 A1 | 9/2004 | Shneider et al. | |
| 2009/0246830 A1 | 10/2009 | Kawaoka et al. | |
| 2011/0300604 A1 | 12/2011 | Kawaoka et al. | |
| 2013/0115242 A1 | 5/2013 | Moules et al. | |
| 2013/0243804 A1 * | 9/2013 | Stoloff | C07K 14/005 530/324 |
| 2015/0017205 A1 | 1/2015 | Kawaoka et al. | |
| 2015/0166967 A1 | 6/2015 | Kawaoka et al. | |
| 2015/0368621 A1 | 12/2015 | Kawaoka et al. | |
| 2016/0002606 A1 | 1/2016 | Peterka et al. | |
| 2016/0284020 A1 | 9/2016 | Williams | |
| 2017/0198264 A1 | 7/2017 | Kawaoka et al. | |
| 2017/0216425 A1 | 8/2017 | Ahmed et al. | |
| 2017/0258888 A1 | 9/2017 | Kawaoka et al. | |
| 2017/0354730 A1 | 12/2017 | Kawaoka et al. | |
| 2018/0340152 A1 | 11/2018 | Kawaoka et al. | |
| 2019/0048324 A1 | 2/2019 | Kawaoka et al. | |
| 2019/0060441 A1 | 2/2019 | Bilsel et al. | |
| 2019/0167781 A1 | 6/2019 | Kawaoka et al. | |
| 2019/0184007 A1 | 6/2019 | Ahmed et al. | |
| 2020/0061182 A1 | 2/2020 | Bilsel et al. | |
| 2020/0188506 A1 | 6/2020 | Kawaoka et al. | |
| 2020/0263143 A1 | 8/2020 | Kawaoka et al. | |
| 2022/0241397 A1 * | 8/2022 | Hatta | C07K 14/005 |
| 2023/0256086 A1 * | 8/2023 | Moser | A61K 39/215 424/204.1 |

FOREIGN PATENT DOCUMENTS

| | | | |
|---|---|---|---|
| CN | 102864129 A | 1/2013 | |
| WO | 2005115448 A2 | 12/2005 | |
| WO | 2006083286 A2 | 8/2006 | |
| WO | WO 2010/117786 A1 | 10/2010 | |
| WO | 2011014504 A1 | 2/2011 | |
| WO | 2015063085 A1 | 5/2015 | |
| WO | 2015142671 A2 | 9/2015 | |
| WO | WO 2017/007839 A1 | 1/2017 | |
| WO | 2017184626 A1 | 10/2017 | |
| WO | WO 2018/157028 A1 | 8/2018 | |
| WO | WO 2018/157047 A1 | 8/2018 | |
| WO | WO 2022/020460 A1 | 1/2022 | |
| WO | WO 2022/020469 A1 | 1/2022 | |

OTHER PUBLICATIONS

Hatta et al., "M2SR, a novel live influenza vaccine, protects mice and ferrets against highly pathogenic avian influenza," *Vaccine* 35(33): 4177-4183 (2017).

Hu et al., "A Vero-cell-adapted vaccine donor strain of influenza A virus generated by serial passages," *Vaccine* 33(2): 374-381 (2014).

Liedmann et al., "Viral suppressors of the RIG-I-mediated interferon responses are pre-packaged in influenza virions," *Nature Communications*, 5(5645): 1-8 (Dec. 9, 2014).

Yamaji et al., "Mammalian Adaptive Mutations of the PA Protein of Highly Pathogenic Avian H5N1 Influenza Virus," *Journal of Virology*, 89(8): 4117-4133 (Jan. 28, 2015).

European Patent Office, Extended European Search Report in European Patent Application No. 20 818 294.9 (Mar. 13, 2023).

U.S. Patent and Trademark Office, International Search Report in International Patent Application No. PCT/US2021/042561 (Dec. 21, 2021).

U.S. Patent and Trademark Office, Written Opinion in International Patent Application No. PCT/US2021/042561 (Dec. 21, 2021).

Ping et al., "Development of high-yield influenza A virus vaccine viruses," *Nat. Commun.*, 6: 8148 (2015).

U.S. Patent and Trademark Office, International Search Report for International Patent Application PCT/US2020/036455 (Sep. 30, 2020).

U.S. Patent and Trademark Office, International Search Report in International Patent Application No. PCT/US2021/042572 (Nov. 10, 2021).

U.S. Patent and Trademark Office, Written Opinion in International Patent Application No. PCT/US2021/042572 (Nov. 10, 2021).

Uniprot, Identification No. A0A0M3Z509_9INFA, NP.5 (Jun. 5, 2019) [retrieved from the internet URL https://www.uniprot.org/uniprot/A0A0M3Z509.txt?version=21> on Sep. 2, 2020].

Uniprot, Identification No. A0A0M5HQ96_9INFA, PB1.5 (Jun. 5, 2019) [retrieved from the internet URL https://www.uniprot.org/uniprot/A0A0M5HQ96.txt?version=20> on Sep. 2, 2020].

Watanabe et al., "Influenza A Virus Lacking M2 Protein as a Live Attenuated Vaccine," *Journal of Virology*, 83(11): 5947-5950 (2009).

Furusawa et al., "Influenza Virus Polymerase Mutation Stabilizes a Foreign Gene Inserted into the Virus Genome by Enhancing the Transcription/Replication Efficiency of the Modified Segment," mBio 10(5): e01794-19 (2019).

Heaton et al., "In Vivo Bioluminescent Imaging of Influenza A Virus Infection and Characterization of Novel Cross-Protective Monoclonal Antibodies," Journal of Virology, 87(15): 8272-8281 (2013).

Hoffmann et al., "Universal primer set for the full-length amplification of all influenza A viruses," Arch. Virol., 146: 2275-2289 (2001).

Jin et al., "Multiple amino acid residues confer temperature sensitivity to human influenza virus vaccine strains (FluMist) derived from cold-adapted A/Ann Arbor/6/60," Virology, 306: 18-24 (2003).

Manicassamy et al., "Analysis of in vivo dynamics of influenza virus infection in mice using a GFP reporter virus," PNAS, 107(25): 11531-11536 (2010).

Nogales et al., "A Novel Fluorescent and Bioluminescent Bireporter Influenza A Virus To Evaluate Viral Infections," Journal of Virology, 93(10): e00032-19 (2019).

(56) References Cited

OTHER PUBLICATIONS

Pan et al., "Development and application of bioluminescence imaging for the influenza A virus," J. Thorac. Dis., 10 (Suppl. 19): S2230-S2237 (2018).

Wang et al., "Generation of a Reassortant Influenza A Subtype H3N2 Virus Expressing Gaussia Luciferase," Viruses, 11(7): 665 (2019).

European Patent Office, Extended European Search Report in European Patent Application No. 21845261.3 (Sep. 30, 2024).

European Patent Office, Extended European Search Report in European Patent Application No. 21845413.0 (Oct. 14, 2024).

Japan Patent Office, Notice of Reasons for Refusal in Japanese Patent Application No. 504319-2023 (Jul. 29, 2025).

\* cited by examiner

Body Weight Change after Challenge

Body Weight Change after Prime immunization

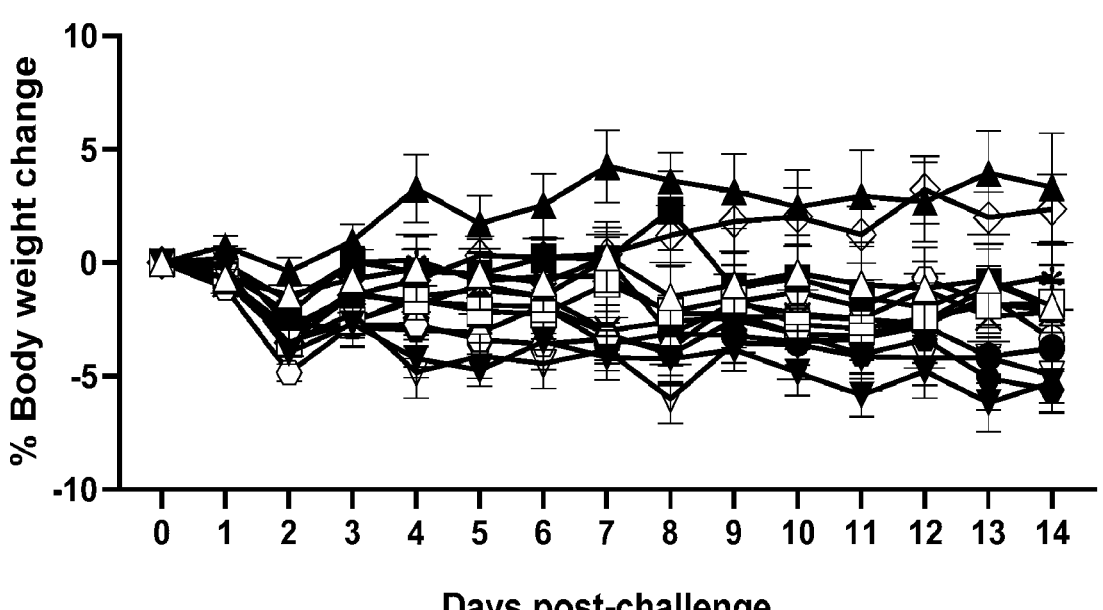

% Body Weight Change

- Group 1: WT/M2SR Quad
- Group 2: WT/FLUMIST$^{TM}$Quad
- Group 3: WT/FLUZONE$^{TM}$Quad
- Group 4: WT/PBS
- Group 5: PBS/M2SR Quad
- Group 6: PBS/FLUMIST$^{TM}$Quad
- Group 7: PBS/FLUZONE$^{TM}$Quad
- Group 8: PBS/PBS
- Group 9: PBS/M2SR Tri-Yam
- Group 10: M2SR Tri-Yam/M2SR Tri-Yam
- Group 11: M2SR Quad/M2SR Quad
- Group 12: FLUMIST$^{TM}$Quad/FLUMIST$^{TM}$Quad
- Group 13: FLUZONE$^{TM}$Quad/FLUZONE$^{TM}$Quad

FIG. 19A

Body Temperature Change

-△- Group 1: WT/M2SR Quad

-▲- Group 2: WT/FLUMIST™ Quad

-▼- Group 3: WT/FLUZONE™ Quad

-▽- Group 4: WT/PBS

-□- Group 5: PBS/M2SR Quad

-■- Group 6: PBS/FLUMIST™ Quad

-◇- Group 7: PBS/FLUZONE™ Quad

-⬟- Group 8: PBS/PBS

-✳- Group 9: PBS/M2SR Tri-Yam

-●- Group 10: M2SR Tri-Yam/M2SR Tri-Yam

-○- Group 11: M2SR Quad/M2SR Quad

-✱- Group 12: FLUMIST™ Quad/FLUMIST™ Quad

-◈- Group 13: FLUZONE™ Quad/FLUZONE™ Quad

SEQUENCE LISTING

<160> NUMBER OF SEQ ID NOS: 20

<210> SEQ ID NO 1
<211> LENGTH: 3
<212> TYPE: RNA
<213> ORGANISM: Influenza B virus

<400> SEQUENCE: 1 aug                                                                    3

<210> SEQ ID NO 2
<211> LENGTH: 9
<212> TYPE: RNA
<213> ORGANISM: Influenza B virus

<400> SEQUENCE: 2 aaaaaaaug                                                              9

<210> SEQ ID NO 3
<211> LENGTH: 10
<212> TYPE: RNA
<213> ORGANISM: Influenza B virus

<400> SEQUENCE: 3
aaaaaaaaug                                                             10

<210> SEQ ID NO 4
<211> LENGTH: 1100
<212> TYPE: DNA
<213> ORGANISM: Influenza B virus

<400> SEQUENCE: 4
agcagaagca gaggatttgt ttagtcactg gcaaacggga aaaaaatggc ggacaacatg      60
accacaacac aaattgaggt gggtccggga gcaaccaatg ccactataaa cttttgaagca    120 ggaattttgg agtgctatga aaggctttca tggcaaagag cccttgacta ccctggtcaa     180
gaccgcctaa acagactaaa gagaaaatta gaatcaagaa taaagactca caacaaaagt     240
gagcctgaaa gtaaaaggat gtctcttgaa gagagaaaag caattggggt aaaaatgatg     300
aaagtgctcc tatttatgaa cccatctgct ggaattgaag ggtttgagcc atactgtatg     360
aaaaattcct ccaatagcaa ctgcccaaac tgcaattggg ccgattaccc tccaacatca     420
sgaaagtgcc ttgatgacat agaagaagaa ccggagaatg ttgatgaccc aactgaaata     480
gtattaaggg acatgaacaa caaagatgca aggcaaaaga taaaagagga agtaaacact     540
cagaaagaag ggaagttccg tttgacaata aaaaagggat atacgtaatg tgttgtcctt     600
gagagtgttg gtaaacggaa cattcctcaa gcaccctaat ggatacaagt ccttatcaac     660
tctgcataga ttgaatgcat atgaccagag tggaaggctt gttgctaaac ttgttgctac     720
tgatgatctt acagtggagg atgaagaaga tggccatcgg atcctcaact cactcttcga     780 gcgtttttaat gaaggacatt caaagccaat tcgagcagct gaaactgcgg tgggagtctt    840
atcccaattt ggtcaagagc accgattatc accagaggag ggagacaatt agactggtta     900
cggaagaact ttatctttta agtaaaagaa ttgatgataa catattgttc cacaaaacag     960
taatagctaa cagctccata atagctgaca tgattgtatc attatcatta ttggaaacat    1020
tgtatgagat gaaggatgtg gttgaagtgt acagcaggca gtgcttgtga atttaaaata    1080
aaaatcctct tgttactact                                                1100

```
<210> SEQ ID NO 5
<211> LENGTH: 4
<212> TYPE: PRT
<213> ORGANISM: Influenza B virus

<400> SEQUENCE: 5

Lys Gly Tyr Thr
1

<210> SEQ ID NO 6
<211> LENGTH: 3
<212> TYPE: DNA
<213> ORGANISM: Influenza B virus

<400> SEQUENCE: 6 taa                                                                      3

<210> SEQ ID NO 7
<211> LENGTH: 180
<212> TYPE: PRT
<213> ORGANISM: Influenza B virus
<220> FEATURE:
<221> NAME/KEY: misc_feature
<222> LOCATION: (126)..(126)
<223> OTHER INFORMATION: Xaa can be any amino acid

<400> SEQUENCE: 7

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asn Pro Ser Ala Gly
                85                  90                  95

Ile Glu Gly Phe Glu Pro Tyr Cys Met Lys Asn Ser Ser Asn Ser Asn
            100                 105                 110

Cys Pro Asn Cys Asn Trp Ala Asp Tyr Pro Pro Thr Ser Xaa Lys Cys
        115                 120                 125

Leu Asp Asp Ile Glu Glu Glu Pro Glu Asn Val Asp Asp Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Lys Gly Tyr Thr
            180

<210> SEQ ID NO 8
<211> LENGTH: 2369
<212> TYPE: DNA
<213> ORGANISM: Influenza B virus

<400> SEQUENCE: 8
agcagaagcg gagcctttaa gatgaatata aatccttatt ttctcttcat agatgtaccc      60
atacaggcag caatttcaac aacattccca tacaccggtg ttccccctta ttcccatgga     120
```

```
acgggaacag gctacacaat agacaccgtg atcagaacac atgagtactc aaacaaggga      180
aaacagtaca tttctgatgt tacaggatgt acaatggtag atccaacaaa tgggccatta      240
cccgaagaca atgagccgag tgcctatgca caattagatt gcgttctgga ggctttggat      300
agaatggatg aagaacatcc aggtctgttt caagcagcct cacagaatgc catggaggca      360
ctaatggtca caactgtaga caaattaacc caggggagac agacttttga ttggacagta      420
tgcagaaacc aacctgctgc aacggcactg aacacaacaa taacctcttt taggttgaat      480
gatttgaatg gagccgacaa gggtggatta gtacccttt gccaagatat cattgattca       540
ttggacagac ctgaaatgac tttcttctca gtaaagaata taaagaaaaa attgcctgct      600
aaaaacagaa agggtttcct cataaagaga ataccaatga aggtaaaaga cagaataacc      660
agagtggaat acatcaaaag agcattatca ttaaacacaa tgacaaaaga tgctgaaaga      720
ggcaaactaa aaagaagagc gattgccacc gctggaatac aaatcagagg gtttgtatta      780
gtagttgaaa acttggctaa aaatatctgt gaaaatctag aacaaagtgg tttgccagta      840
ggtggaaacg agaagaaggc caaactgtca aatgcagtgg ccaaaatgct cagtaactgc      900
ccaccaggag ggatcagcat gacagtaaca ggagacaata ccaaatggaa tgaatgctta      960
aatccaagaa tcttttttggc tatgactgaa agaataacca gagacagccc aatttggttc     1020
cgggattttt gtagtatagc accggtcttg ttctccaata aaatagccag attgggaaaa     1080
gggtttatga taacaagcaa aacaaaaaga ctgaaggctc aaataccttg tcctgatctg     1140
tttagtatac cattagaaag atataatgaa gaaacaaggg caaaattgaa aaagctgaaa     1200
ccattcttca atgaagaagg aacggcatct ttgtcgcctg ggatgatgat gggaatgttt     1260
aatatgctat ctaccgtgtt gggagtagcc gcactaggta tcaaaaacat tggaaacaaa     1320
gaatacttat gggatggact gcaatcttct gatgatttg ctctgtttgt taatgcaaaa      1380
gatgaagaga catgtatgga aggaataaac gacttttacc gaacatgtaa actattggga     1440
ataaacatga gcaaaagaa aagttactgt aatgaaactg gaatgtttga atttacaagc      1500
atgttctaca gagatggatt tgtatctaat tttgcaatgg aacttccttc atttggagtt     1560
gctggagtaa atgaatcagc agatatggca ataggaatga caataataaa gaacaatatg     1620
atcaacaatg gatgggtcc agcaacagca caaacagcca tacaattatt catagctgat      1680
tatagataca cctacaaatg ccacagggga gattccaaag tggaaggaaa gagaatgaaa     1740
attataaagg agctatggga aaacactaaa ggaagagatg gtctgttagt agcagatggt      1800
gggcctaaca tttacaattt gagaaacttg catatcccag aaatagtatt aaagtacaac     1860
ctaatggacc ctgaatacaa agggcggtta cttcatcctc aaaatccctt gtgtaggacat     1920 ttgtctattg agggcatcaa agaggcagat ataaccccag cacatggtcc agtaaagaaa     1980
atggactatg atgcggtgtc tggaactcat agttggagaa ccaaaaggaa cagatctata     2040
ctaaacactg atcagaggaa catgattctt gaggaacaat gctacgctaa gtgttgcaac     2100 cttttttgagg cctgtttttaa cagtgcatca tacaggaaac cagtaggtca gcacagcatg     2160
cttgaggcta tggcccacag attaagaatg gatgcacgac tagattatga atcaggaaga     2220
atgtcaaagg atgattttga aaagcaatg gctcaccttg tgagattgg gtacatataa       2280 gcttcgaaga tgtctatggg gttattggtc atcattgaat acatgcggta cacaaatgat     2340
taaaatgaaa aaaggctcgt gtttctact                                       2369
```

<210> SEQ ID NO 9

-continued

```
<211> LENGTH: 2396
<212> TYPE: DNA
<213> ORGANISM: Influenza B virus

<400> SEQUENCE: 9
agcagaagcg gagcgttttc aagatgacat tggctaaaat tgaattgtta aaacaactgt      60
taagggacaa cgaagccaaa acagtattga aacaaacaac ggtagaccaa tataacataa     120
taagaaaatt caatacatca agaattgaaa agaacccttc attaaggatg aagtgggcca     180
tgtgttctaa ttttcccttg gctctgacca agggtgatat ggcaaataga atcccccttgg    240 aatacaaggg aatacaactt aaaacaaatg ctgaagacat aggaaccaaa ggccaaatgt     300
gctcaatagc agcagttacc tggtggaata catatggacc aataggagac actgaaggtt     360
tcgaaaaggt ctacgaaagc ttctttctca gaaagatgag acttgacaat gccacttggg     420
gccgaataac ttttggccca gttgaaagag taagaaaaag ggtactgcta aaccctctca     480
ccaaggaaat gcctccagat gaagcgagca atgtgataat ggaaatattg ttccctaagg     540
aagcaggaat accaagagaa tctacttgga tacatgggga actgataaaa gaaaaaagag     600
aaaaattgaa aggaacgatg ataactccca ttgtactggc atacatgctt gagagagaat     660
tggttgcccg aagaaggttc ctgccagtgg caggagcaac atcagctgag ttcatagaaa     720
tgctacactg cttacaaggt gaaaattgga caaaatata tcacccagga gggaataaac     780
taactgaatc taggtctcaa tcaatgattg tagcttgtag aaaaataatc agaagatcaa     840
tagtcgcatc aaacccacta gagctagctg tagaaattgc aaacaagact gtgatagata     900
ctgaaccttt aaaatcatgt ctggcagcca tagacggagg tgatgtagcc tgtgacataa     960
tgagagctgc attaggacta aagatcagac aaagacaaag atttggacgg cttgaactaa    1020
agagaatatc aggaagagga ttcaaaaatg atgaagaaat attgatcggg aacggaacaa    1080
tacagaagat tggaatatgg gacggagaag aggagttcca tgtaagatgt ggtgaatgca    1140 gggaatatt aaaaaagagc aaaatgaaa tggaaaaact actaataaat tcagccaaaa    1200
aggaggacat gaaagattta ataatcttgt gcatggtatt ttctcaagac actaggatgt    1260
tccaaggagt gagaggagaa ataaattttc ttaatcgagc aggccaactt ttatctccaa    1320
tgtaccaact ccaaagatat tttttgaata ggagcaacga tctttttgat caatgggggt    1380
atgaggaatc acccaaagca agtgaactac atgggataaa tgaattaatg aatgcatctg    1440
attatacgtt gaaaggggtt gtagtaacaa aaaatgtgat tgatgacttt agttctactg    1500
aaacagaaaa agtatctata acaaaaaatc ttagtttaat aaaaagaact ggggaagtca    1560 taatggggc taatgacgta agtgaattag aatcacaagc tcagctaatg ataacatatg    1620
atacacctaa gatgtgggag atgggaacaa ccaaagaact ggtgcaaaac acctaccaat    1680
gggtgctaaa aaatttggta acactgaagg ctcagtttct tctaggaaaa aagacatgt    1740 tccaatggga tgcatttgaa gcatttgaaa gcataatccc ccagaagatg ctggccagt     1800 acagtggatt tgcaagggca gtgctcaaac aaatgagaga ccaagaggtt atgaaaactg    1860
accagttcat aaagttgttg cctttctgtt tctcaccacc aaaattaagg agcaatgggg    1920
agccttatca attcttgagg cttatattga gggaggagg agaaaatttc atcgaagtaa    1980
ggaaagggtc ccctctattc tcctacaatc cacaaacaga agtcctaact atatgcggca    2040
gaatgatgtc attaaaaggg aaaattgaag atgaagaaag gaatagatca atggggaatg    2100
cagtattggc aggctttctc gttagtggca agtatgaccc gatcttggga gatttcaaaa    2160
ctattgaaga acttgaaaag ctaaaaccgg gggagaaagc aaacatctta ctttatcaag    2220
```

-continued

```
gaaagcccgt taaagtagtt aaaaggaaaa gatatagtgc tttatccaat gacatttcac    2280
aaggaattaa gagacaaaga atgacagttg agtccatggg gtgggccttg agctaatata    2340
aatttatcca ttaattcaat aaacacaatt gagtgaaaaa tgctcgtgtt tctact       2396

<210> SEQ ID NO 10
<211> LENGTH: 2308
<212> TYPE: DNA
<213> ORGANISM: Influenza B virus

<400> SEQUENCE: 10
agcagaagcg gtgcgtttga tttgccataa tggatacttt tattacaaga aacttccaga     60
ctacaataat acaaaaggcc aaaaacacaa tggcagaatt tagtgaagat cctgaattac    120
aaccagcaat gctattcaac atctgcgtcc atctggaggt ctgctatgta ataagtgata    180
tgaattttct tgatgaagaa ggaaaagcat atacagcatt agaaggacaa ggaaaagaac    240
aaaacttgag accacaatat gaagtgattg agggaatgcc aagaacata gcatggatgg    300 ttcaaagatc cttagcccaa gagcatggga tagagactcc aaggtatctg gctgatttgt    360
tcgattataa aactaagagg tttatagaag ttggaataac aaagggattg gctgatgatt    420
acttctggaa aaagaaagaa aagctgggga atagcatgga actgatgata ttcagctaca    480
atcaagacta ttcgttaagt aatgaatcct cattggatga ggaaggaaaa gggagagtgc    540
taagcagact cacagaactt caggctgagt taagtctgaa aaatctatgg caagttctca    600
taggagaaga agatattgaa aaaggaattg acttcaaact tggacaaaca atatctaaac    660
taagggatat atctgttcca gctggtttct ccaattttga aggaatgagg agctacatag    720
acaatataga tcctaaagga gcaatagaga gaaatctagc aaggatgtct cccttagtat    780
cagttacacc taaaaagttg aaatgggagg acctaagacc aatagggcct cacatttaca    840
accatgagct accagaagtt ccatataatg cctttcttct aatgtctgat gaattggggc    900
tggctaatat gactgaaggg aagtccaaga accgaagac cttagccaaa gagtgcctag    960
aaaagtactc aacactacgg gatcaaactg acccaatatt aataatgaaa agcgaaaaag   1020
ctaatgaaca cttcctatgg aaactgtgga gggactgtgt aaatacaata agtaatgagg   1080
aaacaagtaa cgaattacag aaaaccaatt atgccaagtg ggccacagga gatggattaa   1140
catatcagaa aataatgaaa gaagtagcaa tagatgacga acaatgtac caagaagagc   1200 ccaaaatacc taacaaatgt agagtggctg cttgggttca aacagagatg aatctattga   1260
gcactctgac aagtaaaagg gccctggatc tgccagaaat agggccagac gtagcacccg   1320
tggagcatgt agggagtgaa agaaggaaat actttgttaa tgaaatcaac tactgtaagg   1380
cctctaccgt tatgatgaag tatgtgcttt ttcacacttc attattaaat gaaagcaatg   1440
ccagtatggg aaaatataaa gtaataccaa taaccaacag agtagtaaat gaaaagggag   1500
aaagttttga catgctttat ggtctagcgg ttaaagggca atctcatctg aggggagata   1560
ctgatgttgt aacagttgtg actttcgaat ttagtagtac agatcccaga gtggactcag   1620
gaaagtggcc aaaatatact gtatttagaa ttggctcctt atttgtgagt gggagggaa   1680 aatctgtata cctatattgc cgagtgaatg gtacaaataa gatccaaatg aaatggggaa   1740
tggaagctag aagatgtctg cttcaatcaa tgcaacaaat ggaagcaatt gttgaacaag   1800
aatcatcgat acaaggatat gacatgacca aagcttgttt caaggagac agagtgaata   1860 gtccaaaaac tttcagtatt gggactcaag aaggaaaact agtgaaagga tcctttggga   1920
```

-continued

```
aagcactaag agtaatattc accaaatgtt tgatgcacta tgtatttgga aatgcccaat    1980 tggagggggtt tagtgccgaa tctaggagac ttctactgtt aattcaggca ttaaaagaca    2040
gaaagggccc ttgggtattc gacttagagg gaatgtattc tggaatagaa gaatgtatta    2100
gtaacaaccc ttgggtaata cagagtgcat actggtttaa tgaatggttg ggctttgaaa    2160 aagagggggag taaagtatta gaatcagtag atgaaataat ggatgaatga aagaagggca    2220
tagtgctcaa tttggtacta ttttgttcat tatgtatcta aacatccaat ataaagaatt    2280
gagaattaaa aatgcacgtg tttctact                                       2308
```

```
<210> SEQ ID NO 11
<211> LENGTH: 1843
<212> TYPE: DNA
<213> ORGANISM: Influenza B virus

<400> SEQUENCE: 11
agcagaagca cagcattttc ttgtgaactt caagtaccaa caaaaaactg aaaatcaaaa     60
tgtccaacat ggacattgac ggcatcaaca ctggaataat tgacaaaaca ccagaagaaa    120
taacttccgg aaccagtggg gcaaccagac caatcatcag accagcaacc cttgcctcac    180
caagcaacaa acgaaccaga aacccatccc cggaaagggc aaccacaagc agtgaagctg    240
atgtcggaag gaaaacccaa aagaaacaaa ctccgacaga gataaagaag agcgtctaca    300
atatggtagt gaaactgggt gaattctaca accagatgat ggtcaaagct ggactcaacg    360
atgacatgga gagaaaccta atccaaaatg cacatgctgt ggaaagaatt ctattggctg    420
ctactgatga caagaaaact gaattccaaa agaaaaagaa tgccagagac gtcaaagaag    480
ggaaagaaga aatagaccat aacaaaacag gaggcacctt ttacaagatg gtaagagata    540
ataaaaccat ctacttcagc cctataagaa ttaccttttt aaaagaagag gtgaaaacaa    600
tgtacaaaac caccatggggg agtgacggtt tcagtggact aaatcacatc atgattgggc    660
attcacagac gaacgatgtc tgtttccaaa gatcaaaggc actaaaaaga gttggacttg    720
acccttcatt aatcagtact tttgcaggaa gcacactccc cagaagatca ggtacaactg    780
gtgttgcgac caaaggaggt ggaactttag tggcagaagc cattcgattt ataggaagag    840
caatggcaga cagagggcta ttgagagaca tcagagccaa gacggcctat gaaaagattc    900
ttctgaatct gaaaaacaag tgctctgcgc cccaacaaaa ggctctggtt gatcaagtga    960
tcggaagtag aaatccaggg attgcagaca tagaagatct caccctgctt gctcgaagta    1020
tggtcgttgt taggccctct gtagcaagca aagtggtgct tcccataagc atctatgcta    1080
aaatacctca actggggttc aacgttgaag aatactctat ggttgggtat gaagccatgg    1140
ctctttataa tatggcaaca cctgtttcca tattaagaat gggagacgat gcaaaagata    1200
aatcacaatt attcttcatg tcttgctttg gagctgccta tgaagaccta agagttctgt    1260
ctgcactaac aggcacggaa ttcaagccta ggtcagcatt aaagtgcaaa ggtttccacg    1320
ttccagcaaa ggagcaagtg gaaggaatgg gggcagctct gatgtccatc aagctccagt    1380
tttgggctcc aatgaccaga tctgggggga atgaagtagg tggagacgga gggtctggtc    1440
aaataagttg cagcccgtg tttgcagtag aaagacctat tgctctaagc aagcaagctg    1500
taagaagaat gctgtcaatg aatattgagg acgtgatgc agatgtcaaa ggaaatctac    1560
tcaagatgat gaatgattca atggctaaga aaaccaatgg aaatgctttc attgggaaga    1620
aaatgttcca aatatcagac aaaaacaaaa ccaatcccgt tgagattcca attaagcaga    1680 ccatcccccag tttcttcttt gggaggggaca cagcagagga ttatgatgac ctcgattatt    1740
```

```
aaagcaacaa aatagacact atggctgtga ttgtttcagt acgtttggaa tgtgggtgtt   1800
tactcttatt gaaataaatg taaaaaatgc tgttgtttct act                     1843

<210> SEQ ID NO 12
<211> LENGTH: 1098
<212> TYPE: DNA
<213> ORGANISM: Influenza B virus

<400> SEQUENCE: 12
agcagaagca gaggatttgt ttagtcactg gcaaacggga aaaaatggcg gacaacatga     60
ccacaacaca aattgaggtg ggtccgggag caaccaatgc cactataaac tttgaagcag    120
gaattttgga gtgctatgaa aggctttcat ggcaaagagc ccttgactac cctggtcaag    180
accgcctaaa cagactaaag agaaaattag aatcaagaat aaagactcac aacaaaagtg    240
agcctgaaag taaaaggatg tctcttgaag agagaaaagc aattggggta aaaatgatga    300
aagtgctcct atttatgaac ccatctgctg gaattgaagg gtttgagcca tactgtatga    360
aaaattcctc caatagcaac tgcccaaact gcaattgggc cgattaccct ccaacatcag    420
gaaagtgcct tgatgacata gaagaagaac cggagaatgt tgatgaccca actgaaatag    480
tattaaggga catgaacaac aaagatgcaa ggcaaaagat aaaagaggaa gtaaacactc    540
agaaagaagg gaagttccgt ttgacaatac aaagggatat acgtaatgtg ttgtccttga    600
gagtgttggt aaacggaaca ttcctcaagc accctaatgg atacaagtcc ttatcaactc    660
tgcatagatt gaatgcatat gaccagagtg gaaggcttgt tgctaaactt gttgctactg    720
atgatcttac agtggaggat gaagaagatg gccatcggat cctcaactca ctcttcgagc    780 gtttttaatga aggacattca aagccaattc gagcagctga aactgcggtg ggagtcttat    840
cccaatttgg tcaagagcac cgattatcac cagaggaggg agacaattag actggttacg    900
gaagaacttt atcttttaag taaaagaatt gatgataaca tattgttcca caaacagta    960 atagctaaca gctccataat agctgacatg attgtatcat tatcattatt ggaaacattg   1020
tatgagatga aggatgtggt tgaagtgtac agcaggcagt gcttgtgaat ttaaaataaa   1080
aatcctcttg ttactact                                                1098

<210> SEQ ID NO 13
<211> LENGTH: 752
<212> TYPE: PRT
<213> ORGANISM: Influenza B virus

<400> SEQUENCE: 13

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
                20                  25                  30

Gly Thr Gly Thr Gly Tyr Thr Ile Asp Thr Val Ile Arg Thr His Glu
            35                  40                  45

Tyr Ser Asn Lys Gly Lys Gln Tyr Ile Ser Asp Val Thr Gly Cys Thr
        50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110
```

-continued

```
Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
        130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Arg
                165                 170                 175

Pro Glu Met Thr Phe Phe Ser Val Lys Asn Ile Lys Lys Lys Leu Pro
                180                 185                 190

Ala Lys Asn Arg Lys Gly Phe Leu Ile Lys Arg Ile Pro Met Lys Val
        195                 200                 205

Lys Asp Arg Ile Thr Arg Val Glu Tyr Ile Lys Arg Ala Leu Ser Leu
        210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
        260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
        290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
                340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
        370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
        420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
        450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Leu Pro Ser Phe Gly
                500                 505                 510

Val Ala Gly Val Asn Glu Ser Ala Asp Met Ala Ile Gly Met Thr Ile
        515                 520                 525
```

-continued

```
Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
            595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
            675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735

Asp Asp Phe Glu Lys Ala Met Ala His Leu Gly Glu Ile Gly Tyr Ile
                740                 745                 750

<210> SEQ ID NO 14
<211> LENGTH: 770
<212> TYPE: PRT
<213> ORGANISM: Influenza B virus

<400> SEQUENCE: 14

Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
                20                  25                  30

Ile Arg Lys Phe Asn Thr Ser Arg Ile Glu Lys Asn Pro Ser Leu Arg
            35                  40                  45

Met Lys Trp Ala Met Cys Ser Asn Phe Pro Leu Ala Leu Thr Lys Gly
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
                100                 105                 110

Phe Glu Lys Val Tyr Glu Ser Phe Phe Leu Arg Lys Met Arg Leu Asp
            115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160
```

-continued

```
Ala Ser Asn Val Ile Met Glu Ile Leu Phe Pro Lys Glu Ala Gly Ile
            165             170             175

Pro Arg Glu Ser Thr Trp Ile His Arg Glu Leu Ile Lys Glu Lys Arg
            180             185             190

Glu Lys Leu Lys Gly Thr Met Ile Thr Pro Ile Val Leu Ala Tyr Met
            195             200             205

Leu Glu Arg Glu Leu Val Ala Arg Arg Arg Phe Leu Pro Val Ala Gly
    210             215             220

Ala Thr Ser Ala Glu Phe Ile Glu Met Leu His Cys Leu Gln Gly Glu
225             230             235             240

Asn Trp Arg Gln Ile Tyr His Pro Gly Gly Asn Lys Leu Thr Glu Ser
                245             250             255

Arg Ser Gln Ser Met Ile Val Ala Cys Arg Lys Ile Ile Arg Arg Ser
            260             265             270

Ile Val Ala Ser Asn Pro Leu Glu Leu Ala Val Glu Ile Ala Asn Lys
            275             280             285

Thr Val Ile Asp Thr Glu Pro Leu Lys Ser Cys Leu Ala Ala Ile Asp
            290             295             300

Gly Gly Asp Val Ala Cys Asp Ile Met Arg Ala Ala Leu Gly Leu Lys
305             310             315             320

Ile Arg Gln Arg Gln Arg Phe Gly Arg Leu Glu Leu Lys Arg Ile Ser
            325             330             335

Gly Arg Gly Phe Lys Asn Asp Glu Glu Ile Leu Ile Gly Asn Gly Thr
            340             345             350

Ile Gln Lys Ile Gly Ile Trp Asp Gly Glu Glu Glu Phe His Val Arg
            355             360             365

Cys Gly Glu Cys Arg Gly Ile Leu Lys Lys Ser Lys Met Arg Met Glu
    370             375             380

Lys Leu Leu Ile Asn Ser Ala Lys Lys Glu Asp Met Lys Asp Leu Ile
385             390             395             400

Ile Leu Cys Met Val Phe Ser Gln Asp Thr Arg Met Phe Gln Gly Val
            405             410             415

Arg Gly Glu Ile Asn Phe Leu Asn Arg Ala Gly Gln Leu Leu Ser Pro
            420             425             430

Met Tyr Gln Leu Gln Arg Tyr Phe Leu Asn Arg Ser Asn Asp Leu Phe
            435             440             445

Asp Gln Trp Gly Tyr Glu Glu Ser Pro Lys Ala Ser Glu Leu His Gly
    450             455             460

Ile Asn Glu Leu Met Asn Ala Ser Asp Tyr Thr Leu Lys Gly Val Val
465             470             475             480

Val Thr Lys Asn Val Ile Asp Asp Phe Ser Ser Thr Glu Thr Glu Lys
            485             490             495

Val Ser Ile Thr Lys Asn Leu Ser Leu Ile Lys Arg Thr Gly Glu Val
            500             505             510

Ile Met Gly Ala Asn Asp Val Ser Glu Leu Glu Ser Gln Ala Gln Leu
            515             520             525

Met Ile Thr Tyr Asp Thr Pro Lys Met Trp Glu Met Gly Thr Thr Lys
            530             535             540

Glu Leu Val Gln Asn Thr Tyr Gln Trp Val Leu Lys Asn Leu Val Thr
545             550             555             560

Leu Lys Ala Gln Phe Leu Leu Gly Lys Glu Asp Met Phe Gln Trp Asp
            565             570             575
```

-continued

```
Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
            595                 600                 605

Val Met Lys Thr Asp Gln Phe Ile Lys Leu Leu Pro Phe Cys Phe Ser
            610                 615                 620

Pro Pro Lys Leu Arg Ser Asn Gly Glu Pro Tyr Gln Phe Leu Arg Leu
625                 630                 635                 640

Ile Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
            675                 680                 685

Ser Met Gly Asn Ala Val Leu Ala Gly Phe Leu Val Ser Gly Lys Tyr
            690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
            755                 760                 765

Leu Ser
    770
```

```
<210> SEQ ID NO 15
<211> LENGTH: 702
<212> TYPE: PRT
<213> ORGANISM: Influenza B virus

<400> SEQUENCE: 15
```

```
Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
            35                  40                  45

Ser Asp Met Asn Phe Leu Asp Glu Glu Gly Lys Ala Tyr Thr Ala Leu
        50                  55                  60

Glu Gly Gln Gly Lys Glu Gln Asn Leu Arg Pro Gln Tyr Glu Val Ile
65                  70                  75                  80

Glu Gly Met Pro Arg Asn Ile Ala Trp Met Val Gln Arg Ser Leu Ala
                85                  90                  95

Gln Glu His Gly Ile Glu Thr Pro Arg Tyr Leu Ala Asp Leu Phe Asp
            100                 105                 110

Tyr Lys Thr Lys Arg Phe Ile Glu Val Gly Ile Thr Lys Gly Leu Ala
            115                 120                 125

Asp Asp Tyr Phe Trp Lys Lys Lys Glu Lys Leu Gly Asn Ser Met Glu
            130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
                165                 170                 175
```

-continued

```
Leu Gln Ala Glu Leu Ser Leu Lys Asn Leu Trp Gln Val Leu Ile Gly
        180                 185                 190

Glu Glu Asp Ile Glu Lys Gly Ile Asp Phe Lys Leu Gly Gln Thr Ile
        195                 200                 205

Ser Lys Leu Arg Asp Ile Ser Val Pro Ala Gly Phe Ser Asn Phe Glu
        210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Val Thr Pro Lys Lys
                245                 250                 255

Leu Lys Trp Glu Asp Leu Arg Pro Ile Gly Pro His Ile Tyr Asn His
                260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
        290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu His Phe Leu
                325                 330                 335

Trp Lys Leu Trp Arg Asp Cys Val Asn Thr Ile Ser Asn Glu Glu Thr
                340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
        370                 375                 380

Thr Met Tyr Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
                420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
        450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
        500                 505                 510

Val Val Thr Val Val Thr Phe Glu Phe Ser Ser Thr Asp Pro Arg Val
        515                 520                 525

Asp Ser Gly Lys Trp Pro Lys Tyr Thr Val Phe Arg Ile Gly Ser Leu
        530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
                580                 585                 590
```

-continued

```
Ser Ile Gln Gly Tyr Asp Met Thr Lys Ala Cys Phe Lys Gly Asp Arg
        595             600             605

Val Asn Ser Pro Lys Thr Phe Ser Ile Gly Thr Gln Glu Gly Lys Leu
        610             615             620

Val Lys Gly Ser Phe Gly Lys Ala Leu Arg Val Ile Phe Thr Lys Cys
625             630             635             640

Leu Met His Tyr Val Phe Gly Asn Ala Gln Leu Glu Gly Phe Ser Ala
            645             650             655

Glu Ser Arg Arg Leu Leu Leu Leu Ile Gln Ala Leu Lys Asp Arg Lys
            660             665             670

Gly Pro Trp Val Phe Asp Leu Glu Gly Met Tyr Ser Gly Ile Glu Glu
            675             680             685

Cys Ile Ser Asn Asn Pro Trp Val Ile Gln Ser Ala Tyr Trp
        690             695             700

<210> SEQ ID NO 16
<211> LENGTH: 560
<212> TYPE: PRT
<213> ORGANISM: Influenza B virus

<400> SEQUENCE: 16

Met Ser Asn Met Asp Ile Asp Gly Ile Asn Thr Gly Ile Ile Asp Lys
1               5               10              15

Thr Pro Glu Glu Ile Thr Ser Gly Thr Ser Gly Ala Thr Arg Pro Ile
            20              25              30

Ile Arg Pro Ala Thr Leu Ala Ser Pro Ser Asn Lys Arg Thr Arg Asn
        35              40              45

Pro Ser Pro Glu Arg Ala Thr Thr Ser Ser Glu Ala Asp Val Gly Arg
    50              55              60

Lys Thr Gln Lys Lys Gln Thr Pro Thr Glu Ile Lys Lys Ser Val Tyr
65              70              75              80

Asn Met Val Val Lys Leu Gly Glu Phe Tyr Asn Gln Met Met Val Lys
            85              90              95

Ala Gly Leu Asn Asp Asp Met Glu Arg Asn Leu Ile Gln Asn Ala His
            100             105             110

Ala Val Glu Arg Ile Leu Leu Ala Ala Thr Asp Asp Lys Lys Thr Glu
            115             120             125

Phe Gln Lys Lys Lys Asn Ala Arg Asp Val Lys Glu Gly Lys Glu Glu
        130             135             140

Ile Asp His Asn Lys Thr Gly Gly Thr Phe Tyr Lys Met Val Arg Asp
145             150             155             160

Asn Lys Thr Ile Tyr Phe Ser Pro Ile Arg Ile Thr Phe Leu Lys Glu
            165             170             175

Glu Val Lys Thr Met Tyr Lys Thr Thr Met Gly Ser Asp Gly Phe Ser
            180             185             190

Gly Leu Asn His Ile Met Ile Gly His Ser Gln Thr Asn Asp Val Cys
            195             200             205

Phe Gln Arg Ser Lys Ala Leu Lys Arg Val Gly Leu Asp Pro Ser Leu
        210             215             220

Ile Ser Thr Phe Ala Gly Ser Thr Leu Pro Arg Arg Ser Gly Thr Thr
225             230             235             240

Gly Val Ala Thr Lys Gly Gly Gly Thr Leu Val Ala Glu Ala Ile Arg
            245             250             255

Phe Ile Gly Arg Ala Met Ala Asp Arg Gly Leu Leu Arg Asp Ile Arg
            260             265             270
```

-continued

```
Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
                340                 345                 350

Ser Met Val Gly Tyr Glu Ala Met Ala Leu Tyr Asn Met Ala Thr Pro
                355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
                420                 425                 430

Ala Leu Met Ser Ile Lys Leu Gln Phe Trp Ala Pro Met Thr Arg Ser
                435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
                500                 505                 510

Asn Gly Asn Ala Phe Ile Gly Lys Lys Met Phe Gln Ile Ser Asp Lys
    515                 520                 525

Asn Lys Thr Asn Pro Val Glu Ile Pro Ile Lys Gln Thr Ile Pro Ser
    530                 535                 540

Phe Phe Phe Gly Arg Asp Thr Ala Glu Asp Tyr Asp Asp Leu Asp Tyr
545                 550                 555                 560
```

```
<210> SEQ ID NO 17
<211> LENGTH: 281
<212> TYPE: PRT
<213> ORGANISM: Influenza B virus

<400> SEQUENCE: 17

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
                20                  25                  30

Arg Leu Ser Trp Gln Arg Ala Leu Asp Tyr Pro Gly Gln Asp Arg Leu
            35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asn Pro Ser Ala Gly
```

-continued

```
                    85              90              95

Ile Glu Gly Phe Glu Pro Tyr Cys Met Lys Asn Ser Ser Asn Ser Asn
            100             105             110

Cys Pro Asn Cys Asn Trp Ala Asp Tyr Pro Pro Thr Ser Gly Lys Cys
            115             120             125

Leu Asp Asp Ile Glu Glu Glu Pro Glu Asn Val Asp Asp Pro Thr Glu
            130             135             140

Ile Val Leu Arg Asp Met Asn Asn Lys Asp Ala Arg Gln Lys Ile Lys
145             150             155             160

Glu Glu Val Asn Thr Gln Lys Glu Gly Lys Phe Arg Leu Thr Ile Gln
                165             170             175

Arg Asp Ile Arg Asn Val Leu Ser Leu Arg Val Leu Val Asn Gly Thr
                180             185             190

Phe Leu Lys His Pro Asn Gly Tyr Lys Ser Leu Ser Thr Leu His Arg
            195             200             205

Leu Asn Ala Tyr Asp Gln Ser Gly Arg Leu Val Ala Lys Leu Val Ala
            210             215             220

Thr Asp Asp Leu Thr Val Glu Asp Glu Glu Asp Gly His Arg Ile Leu
225             230             235             240

Asn Ser Leu Phe Glu Arg Phe Asn Glu Gly His Ser Lys Pro Ile Arg
                245             250             255

Ala Ala Glu Thr Ala Val Gly Val Leu Ser Gln Phe Gly Gln Glu His
                260             265             270

Arg Leu Ser Pro Glu Glu Gly Asp Asn
            275             280

<210> SEQ ID NO 18
<211> LENGTH: 1111
<212> TYPE: DNA
<213> ORGANISM: Influenza B virus

<400> SEQUENCE: 18
agcagaagca cgcactttct taaaatgtcg ctgtttggag acacaattgc ctacctgctt       60
tcattgacag aagatggaga aggcaaagca gaactagcag aaaaattaca ctgttggttc      120
ggtgggaaag aatttgacct agactctgcc ttggaatgga taaaaaacaa aagatgctta      180
actgacatac agaaagcact aattggcgcc tctatctgct ttttaaaacc caaagaccag      240
gaaagaaaaa gaagattcat cacagagccc ctatcaggaa tggggacaac agcaacaaaa      300
aagaagggcc tgattctagc tgagagaaaa atgagaagat gtgtgagctt ccatgaagca      360
tttgaaatag cagaaggcca tgaaagctca gcgttactat attgtctcat ggtcatgtac      420
ctgaatcctg aaattattc aatgcaagta aaactaggaa cgctctgtgc tttgtgcgaa      480
aaacaagcat cacattcaca cagggctcat agcagagcag cgagatcttc agtgcctgga      540
gtgagacggg aaatgcagat ggtctcagct atgaacacag caaaaacaat gaatggaatg      600
ggaaaaggag aagacgttca aaaactggca gaagaactgc aaagcaacat tggagtattg      660
agatctcttg gggcaagtca aaagaatggg gaaggaattg caaggatgt aatggaagtg      720 ctaaagcaga gctctatggg aaattcagct cttgtgaaga ataacctata atgctcgaac      780
catttcagat tctttcaatt tgttagatag ctaaaagggg ccaaataaag agacaataaa      840
cagagaggta tcaattttga cacacagtta ccaaaaagaa atccaggcca agaagcaat      900 gaaggaagta ctctctgaca acatggaggt attgagtgac cacatagtaa ttgaggggct      960
ttctgctgaa gagataataa aaatgggtga aacagttttg gaggtagaag aattgcatta     1020
```

```
aattcaattt ttactgtact tcttactatg catttaagca aattgtaatc aatgtcagca    1080
aataaactgg aaaaagtgcg ttgtttctac t                                   1111

<210> SEQ ID NO 19
<211> LENGTH: 109
<212> TYPE: PRT
<213> ORGANISM: Influenza B virus

<400> SEQUENCE: 19

Met Leu Glu Pro Leu Gln Ile Leu Ser Ile Cys Ser Phe Ile Leu Ser
1               5                   10                  15

Ala Leu His Phe Met Ala Trp Thr Ile Gly His Leu Asn Gln Ile Arg
            20                  25                  30

Arg Gly Val Asn Leu Lys Ile Gln Ile Arg Asn Pro Asn Lys Glu Ala
        35                  40                  45

Ile Asn Arg Glu Val Ser Ile Leu Arg His Asn Tyr Gln Lys Glu Ile
    50                  55                  60

Gln Ala Lys Glu Thr Met Lys Lys Ile Leu Ser Asp Asn Met Glu Val
65                  70                  75                  80

Leu Gly Asp His Ile Val Val Glu Gly Leu Ser Thr Asp Glu Ile Ile
                85                  90                  95

Lys Met Gly Glu Thr Val Leu Glu Val Glu Glu Leu Gln
            100                 105

<210> SEQ ID NO 20
<211> LENGTH: 11
<212> TYPE: PRT
<213> ORGANISM: Influenza B virus

<400> SEQUENCE: 20

Met Leu Glu Pro Phe Gln Ile Leu Ser Ile Cys
1               5                   10
```

INFLUENZA VIRUS BACKBONE

CROSS-REFERENCE TO RELATED APPLICATIONS

This patent application is the U.S. national phase of International Patent Application No. PCT/US2021/042572, filed Jul. 21, 2021, which claims the benefit of U.S. Provisional Patent Application No. 63/054,676, filed Jul. 21, 2020, each of which is incorporated by reference in its entirety herein.

STATEMENT REGARDING FEDERALLY SPONSORED RESEARCH OR DEVELOPMENT

This invention was made with Government support under Grant Number AI109925 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 46,917 Byte ASCII (Text) file named "755023 Sequence-Listing.txt," created on Jul. 20, 2021.

BACKGROUND OF THE INVENTION

Influenza, i.e., the "flu," is a highly contagious viral infection that claims the lives of hundreds of thousands of humans globally each year. There are four types of influenza viruses (i.e., A, B, C, and D) categorized based on their core proteins, although seasonal epidemics are most often caused by circulating Influenza A and B viruses.

While vaccines are the best way to prevent influenza, influenza vaccines must be re-formulated often, as the influenza virus is subject to antigenic drift and antigenic shift. Moreover, because influenza viruses generally exhibit a high rate of mutation and evolution, influenza vaccine strains may mismatch circulating strains, thereby resulting in minimal vaccine effectiveness. However, when circulating flu viruses are well-matched to the flu vaccine, vaccination can reduce the risk of flu-related illness by 40%-60% among the overall population. Accordingly, researchers have been studying vaccines that can induce cross-protective immunity between different influenza subtypes. One such example is a vaccine comprising a live, attenuated influenza virus that does not express a functional M2 protein (e.g., the M2SR vaccine for influenza A).

Influenza vaccines are preferably propagated in Madin-Darby canine kidney (MDCK) cells and African Green Monkey (Vero) cells, as mammalian-cell cultures provide advantages over egg-based production. These advantages include lower costs, faster production time, and a reduced risk of antigenic mutation in the virus. For example, the M2SR vaccine is propagated in Vero cells that stably express M2 protein. However, vaccine production in cell cultures has often resulted in undesirable yields. Moreover, MDCK cells are generally more permissive than Vero cells, such that vaccine production in Vero cells is comparatively inefficient.

Modifications to the virus backbone, i.e., the six internal gene segments consisting of PB1, PB2, PA, NP, M, and NS, have been shown to boost vaccine production. For example, the high-yield influenza A vaccine backbone "PR8-HY"

developed and described in in Ping et al., *Nature Communications,* 6: 8148 (2015), and the high-yield influenza B vaccine backbone developed and described in Ping et al., *PNAS,* 113(51): E8296-E8305 (2016), comprise specific amino acid mutations in the PB1, PB2, PA, NP, and NS1 proteins, and were expected to improve the titers of pandemic and seasonal influenza vaccines in both cell and egg culture systems. However, these modifications described in the art have been ineffective in increasing viral growth in Vero cells, particularly under preferred manufacturing conditions. Therefore, a need exists to enhance viral growth in Vero cells, such that vaccines can be produced more efficiently and effectively.

BRIEF SUMMARY OF THE INVENTION

The invention provides an influenza virus having enhanced growth in Vero cells. The influenza virus comprises gene segments encoding proteins, e.g., the PB1, PB2, PA, NP, and NS1 proteins, wherein at least the PA, NP, and NS gene segments have amino acid sequences comprising selected amino acids. In particular the PA gene segment comprises a thymine at nucleotide position 2272. The NP protein comprises a serine at position 40, and asparagine or glycine at position 161, a threonine at position 204, and optionally a valine at position 93. The NS gene segment comprises a guanine at nucleotide position 39, and the NS gene segment encodes an NS1 protein that comprises a glutamine at position 176.

The invention also provides a pharmaceutical formulation comprising the influenza virus, a method of eliciting an immune response in a mammal comprising administering the influenza virus to the mammal, and a method of generating the influenza virus.

BRIEF DESCRIPTION OF THE SEVERAL VIEWS OF THE DRAWING(S)

Figure 13A:
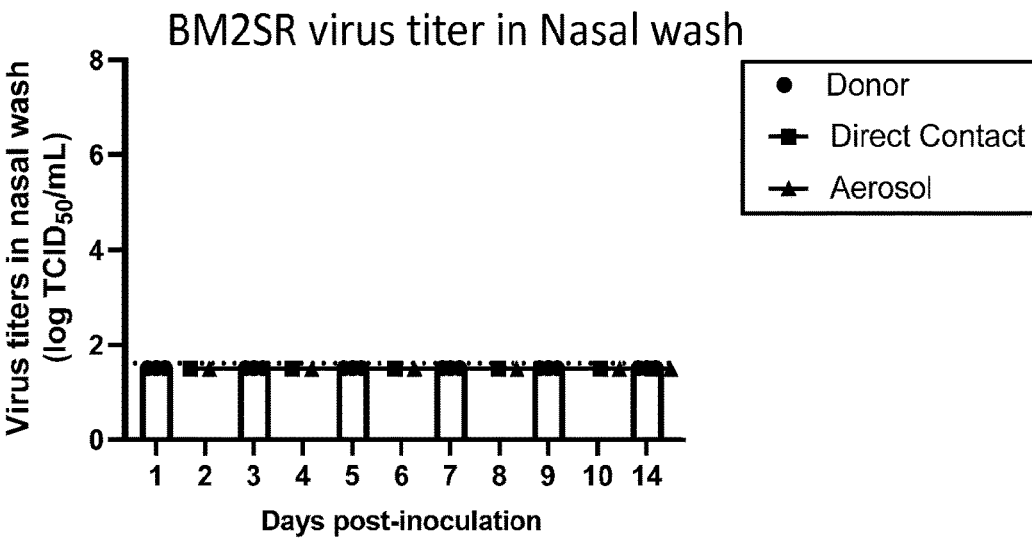
FIG. 13A is a graph depicting BM2SR-Vic virus titers in nasal wash from BM2SR-Vic donor ferrets and their direct contact and aerosol contact ferrets versus time (days post-inoculation). Virus detection limit was 1.67 log $TCID_{50}$/mL (dash line).
Figure 13B:
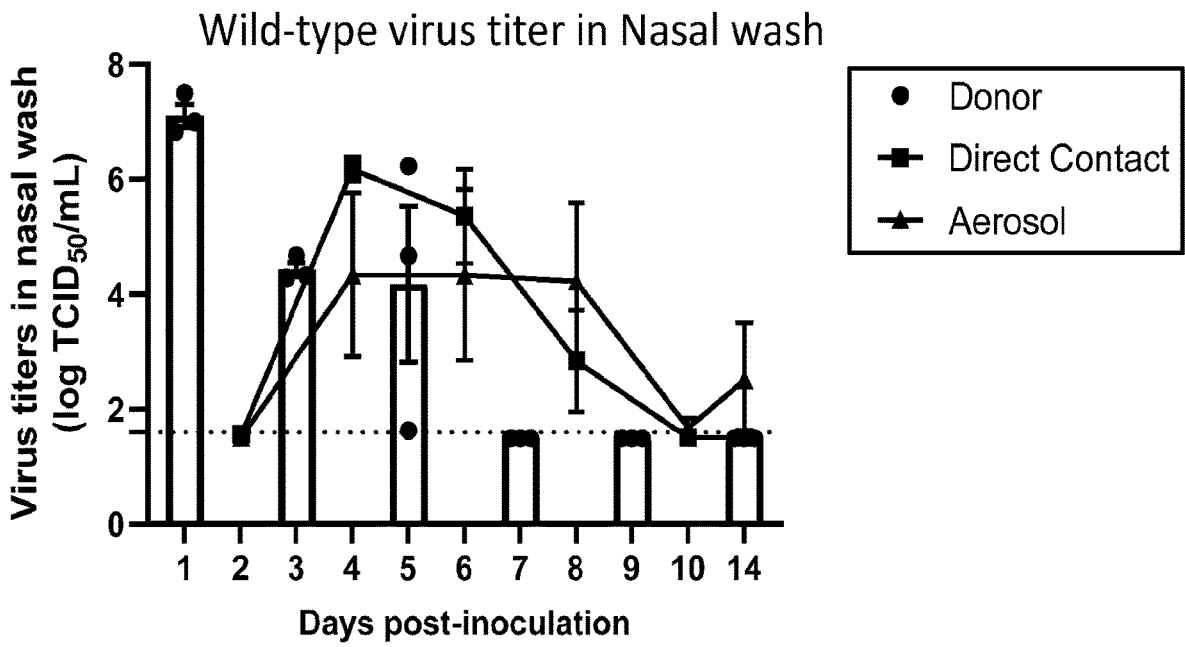

FIG. 13B is a graph depicting wild-type influenza B (Vic) virus titers in nasal wash from influenza B (Vic) donor ferrets and their direct contact and aerosol contact ferrets versus time (days post-inoculation). Virus titer for individual ferret, group average and standard error of the mean are plotted. Virus detection limit was 1.67 log $TCID_{50}$/mL (dash line).

Figure 14A:
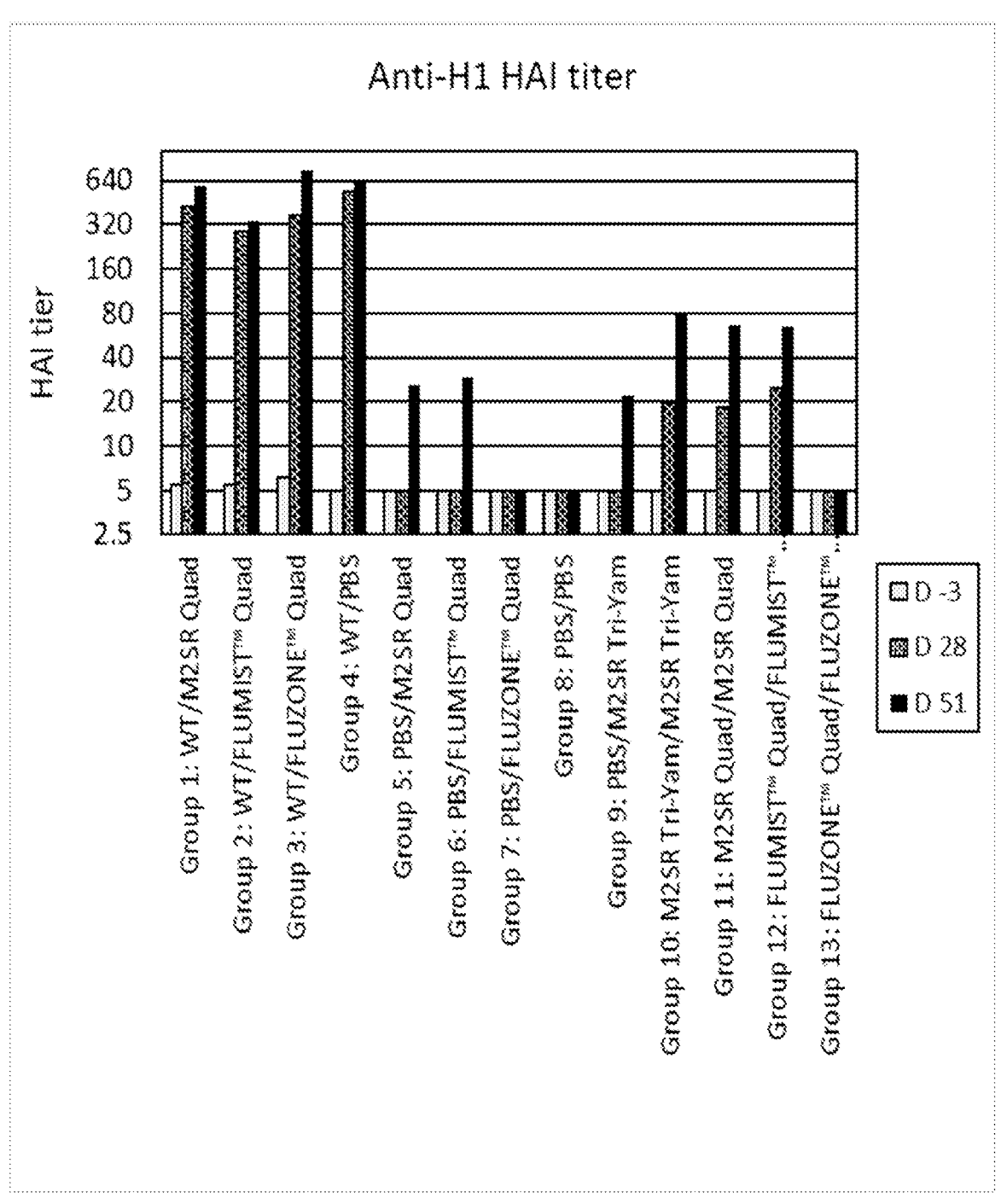

FIG. 14A is a graph depicting the anti-influenza A/H1 HAI titers in sera of 13 ferret groups immunized as described in Table 10 versus time (Study Days). Average titers per group are plotted. Detection limit was 7.5.

Figure 14B:
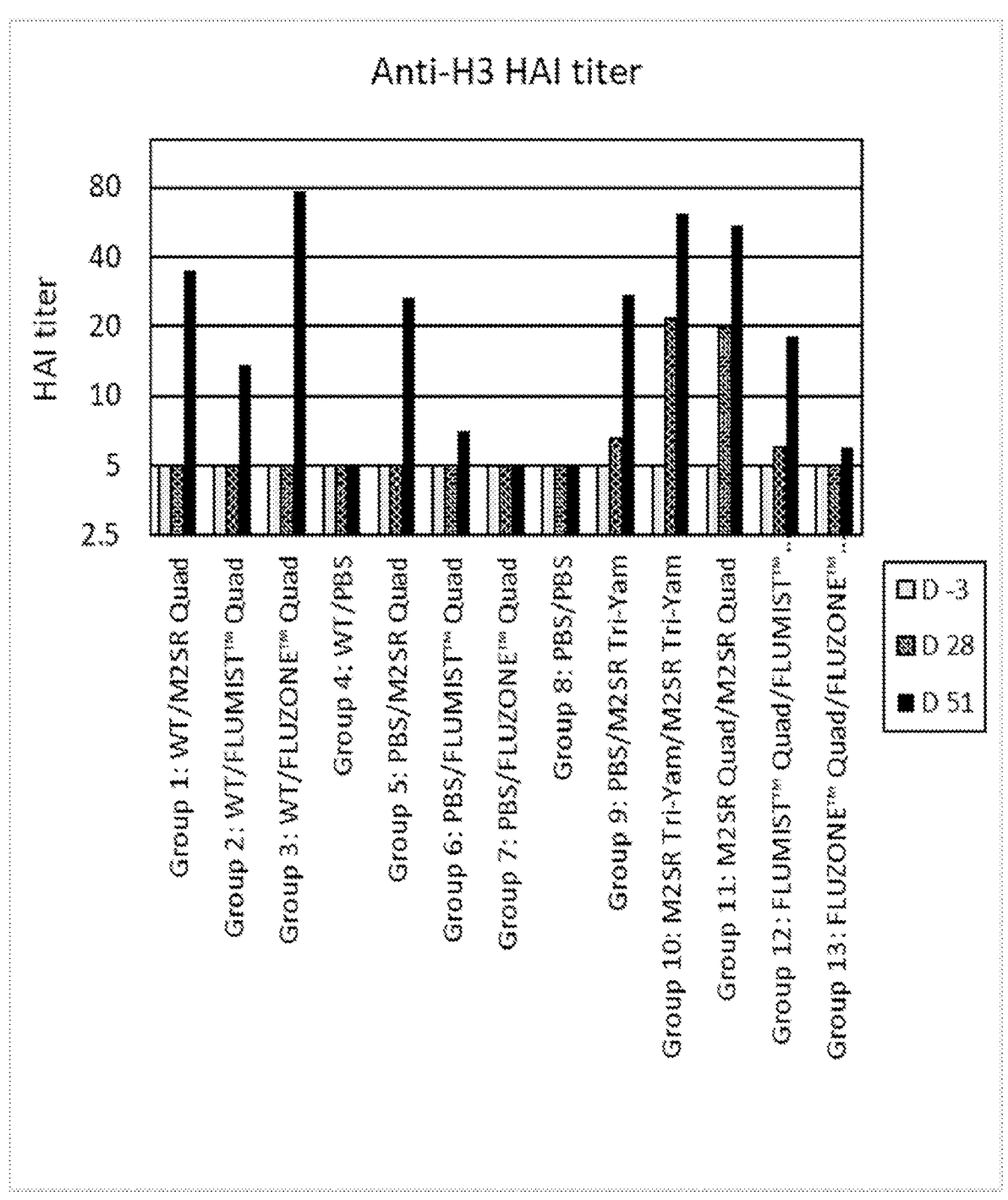

FIG. 14B is a graph depicting the anti-influenza A/H3 HAI titers in sera of 13 ferret groups immunized as described in Table 10 versus time (Study Days). Average titers per group are plotted. Detection limit was 7.5.

Figure 14C:
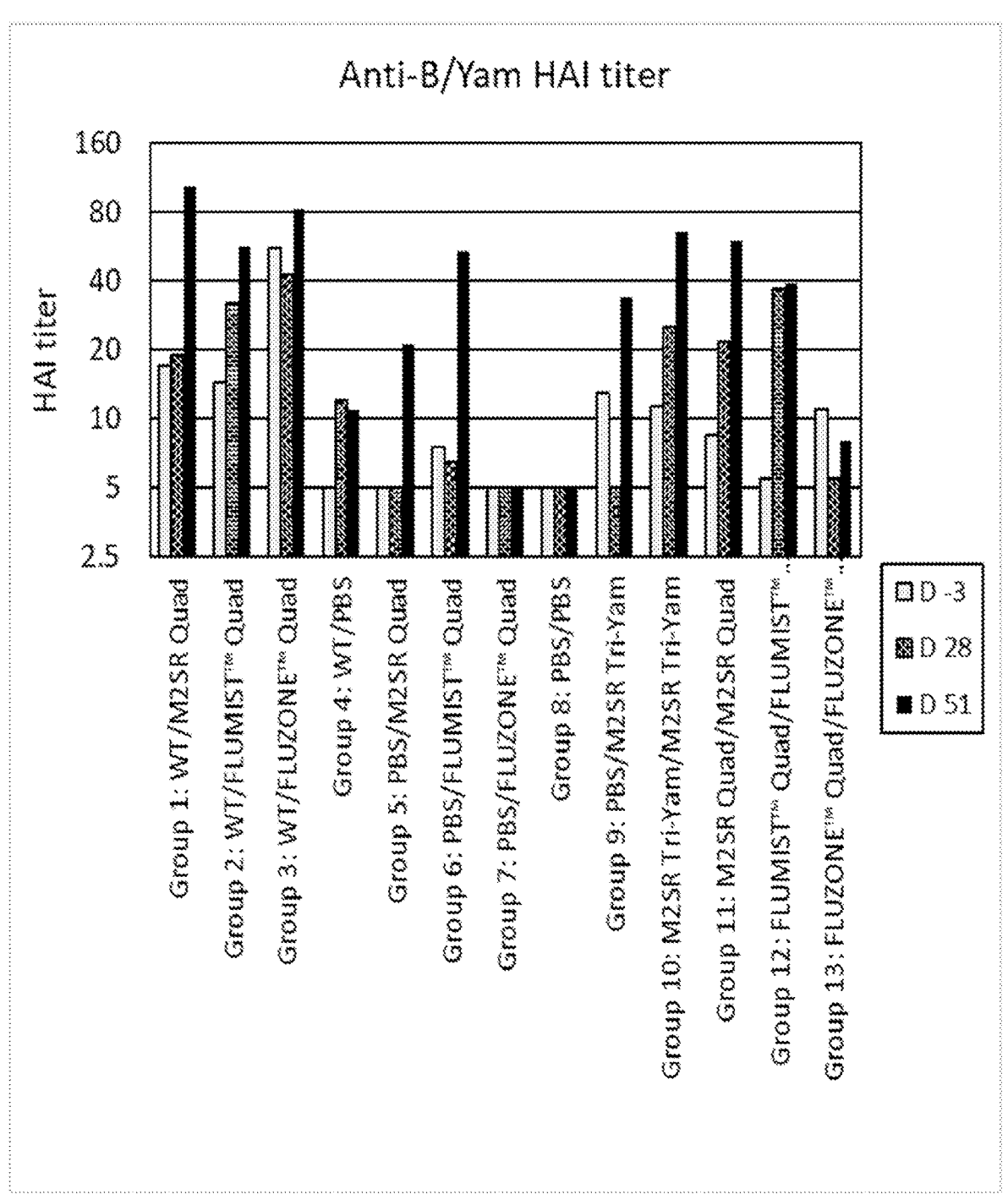

FIG. 14C is a graph depicting the anti-influenza B/Yam HAI titers in sera of 13 ferret groups immunized as described in Table 10 versus time (Study Days). Average titers per group are plotted. Detection limit was 7.5.

Figure 14D:
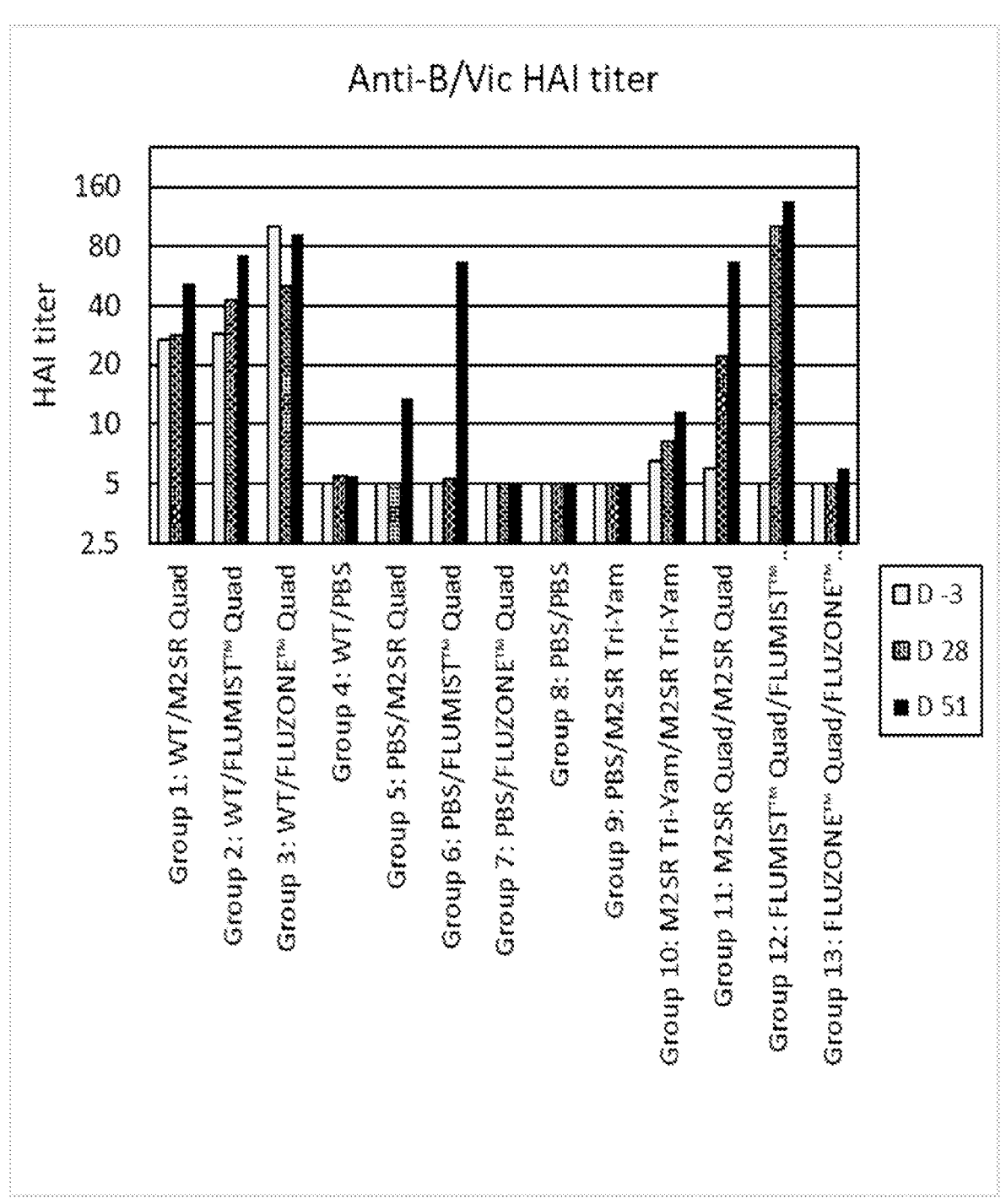

FIG. 14D is a graph depicting the anti-influenza A/Vic HAI titers in sera of 13 ferret groups immunized as described in Table 10 versus time (Study Days). Average titers per group are plotted. Detection limit was 7.5.

Figure 15A:
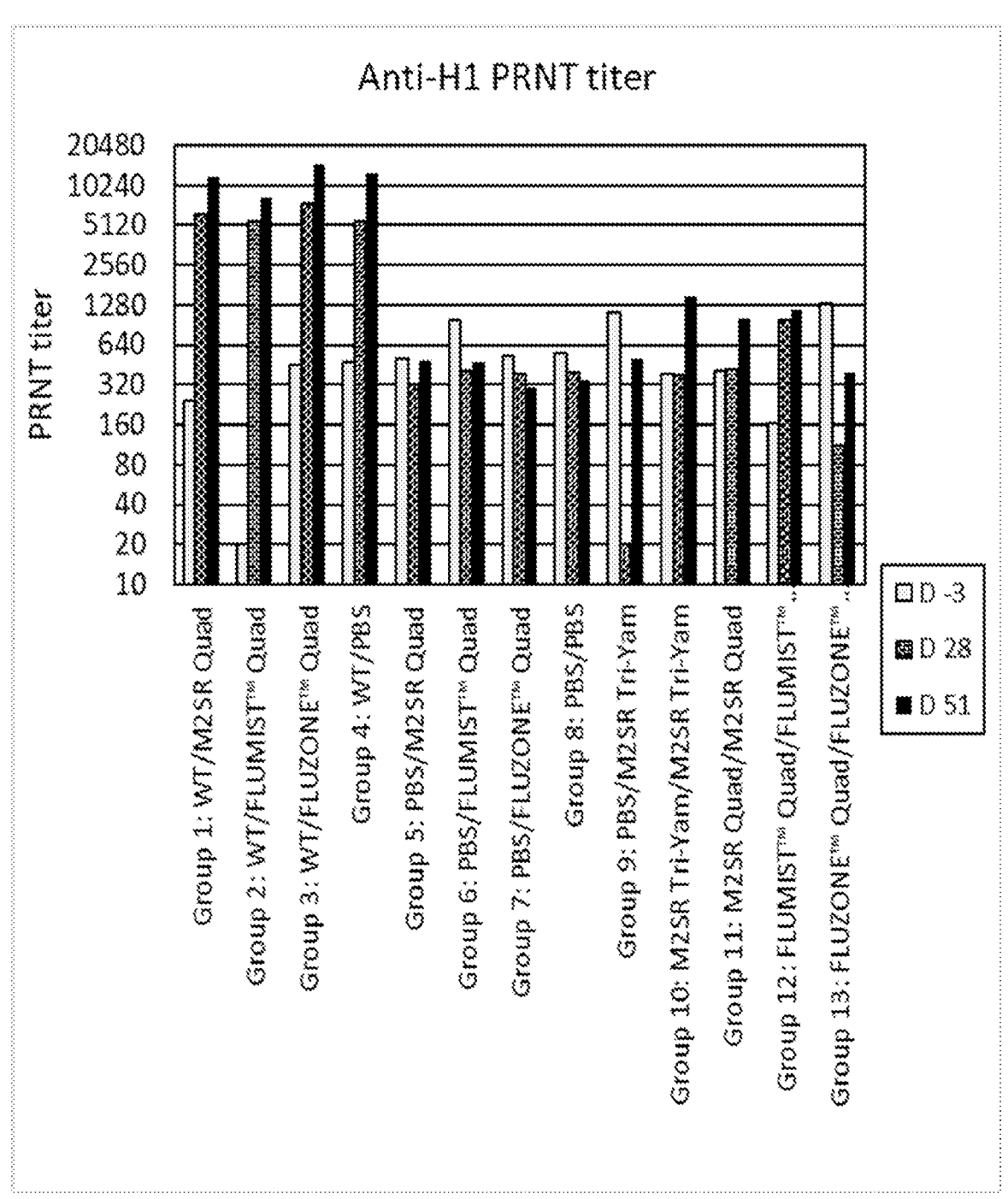

FIG. 15A is a graph depicting the anti-influenza A/H1 PRNT titers in sera of 13 ferret groups immunized as described in Table 10 versus time (Study Days). Average titers per group are plotted. Detection limit was 15.

Figure 15B:
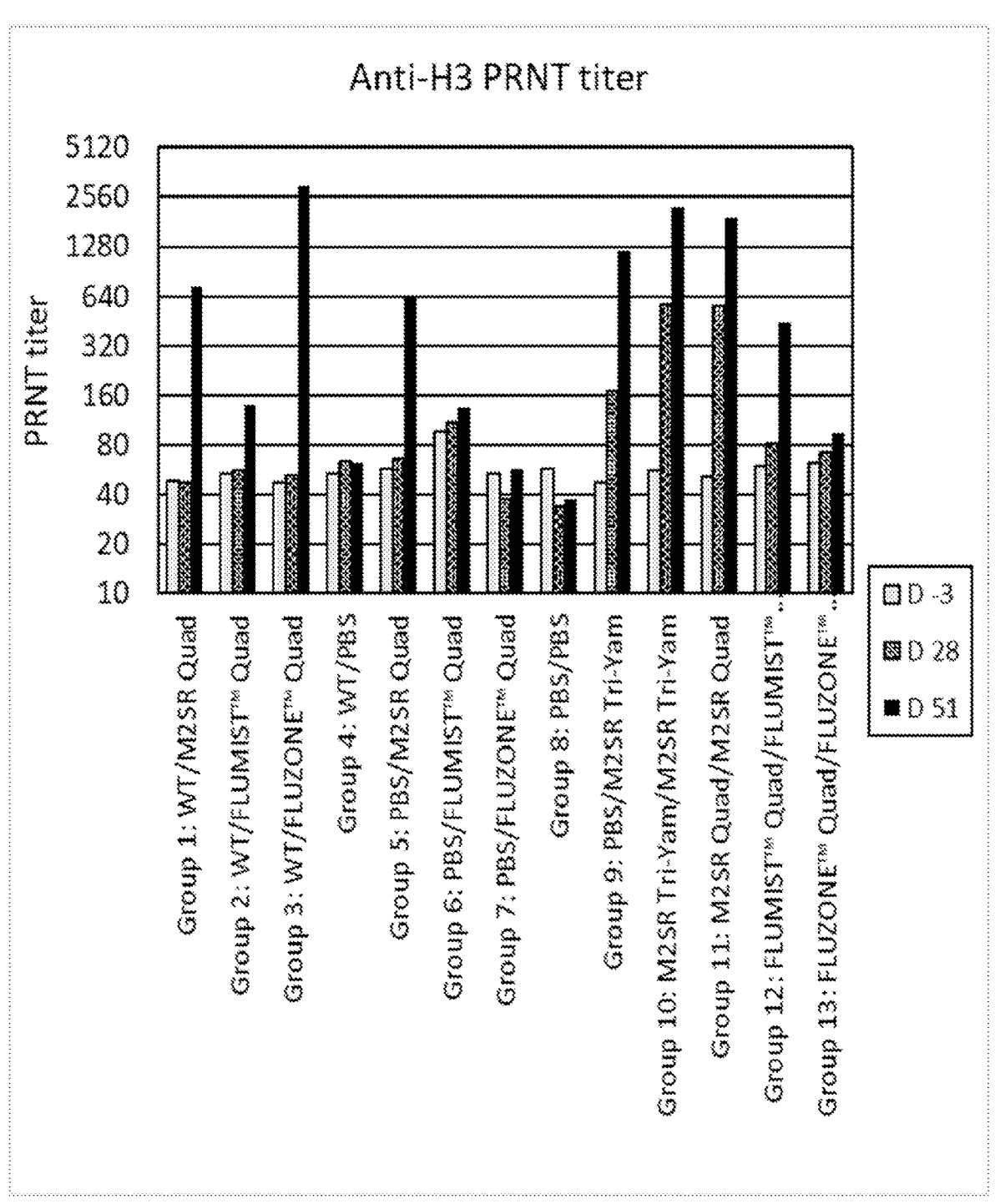

FIG. 15B is a graph depicting the anti-influenza A/H3 PRNT titers in sera of 13 ferret groups immunized as described in Table 10 versus time (Study Days). Average titers per group are plotted. Detection limit was 15.

Figure 15C:
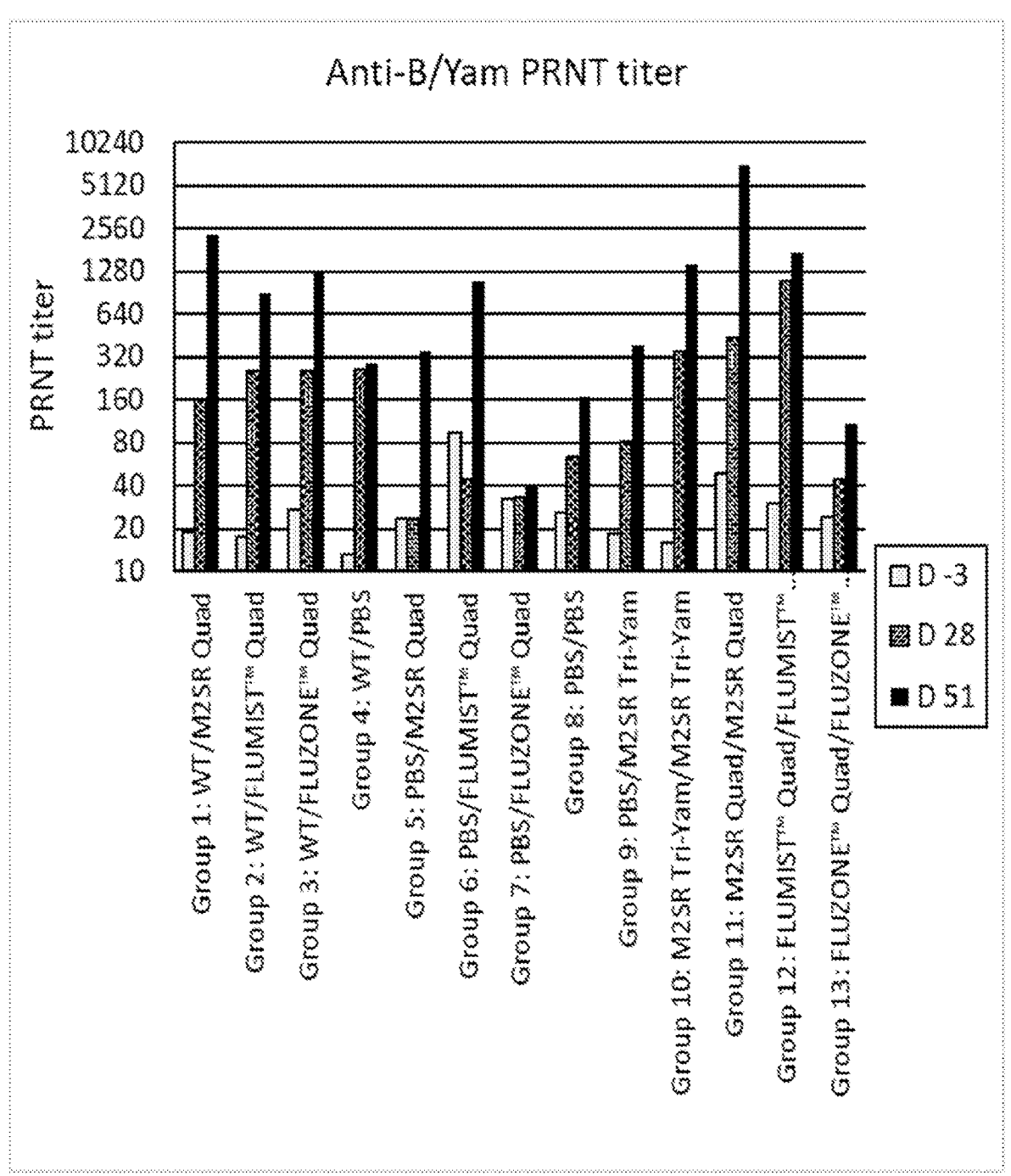

FIG. 15C is a graph depicting the anti-influenza B/Yam PRNT titers in sera of 13 ferret groups immunized as described in Table 10 versus time (Study Days). Average titers per group are plotted. Detection limit was 15.

Figure 15D:
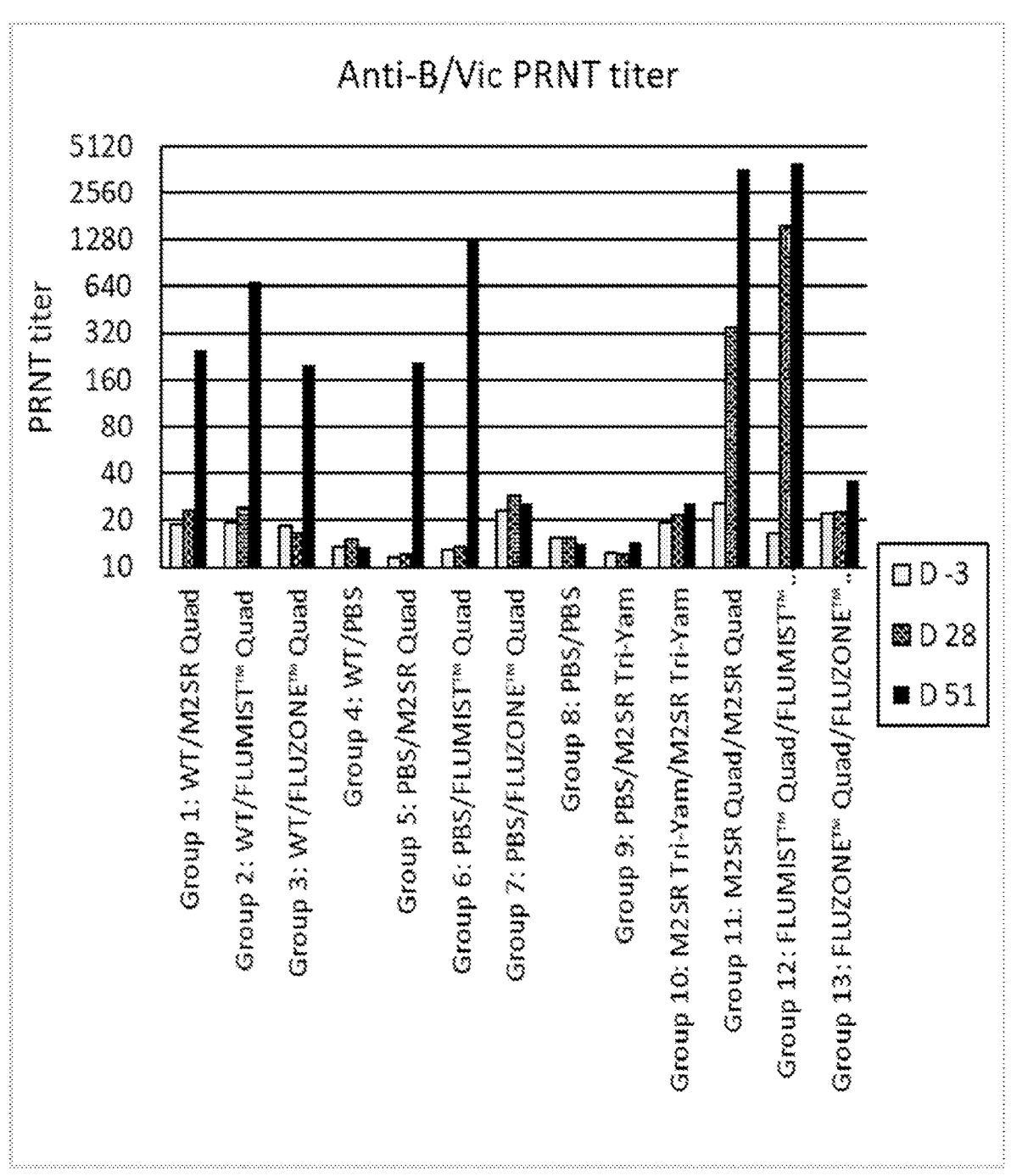

FIG. 15D is a graph depicting the anti-influenza A/Vic PRNT titers in sera of 13 ferret groups immunized as described in Table 10 versus time (Study Days). Average titers per group are plotted. Detection limit was 15.

Figure 16:
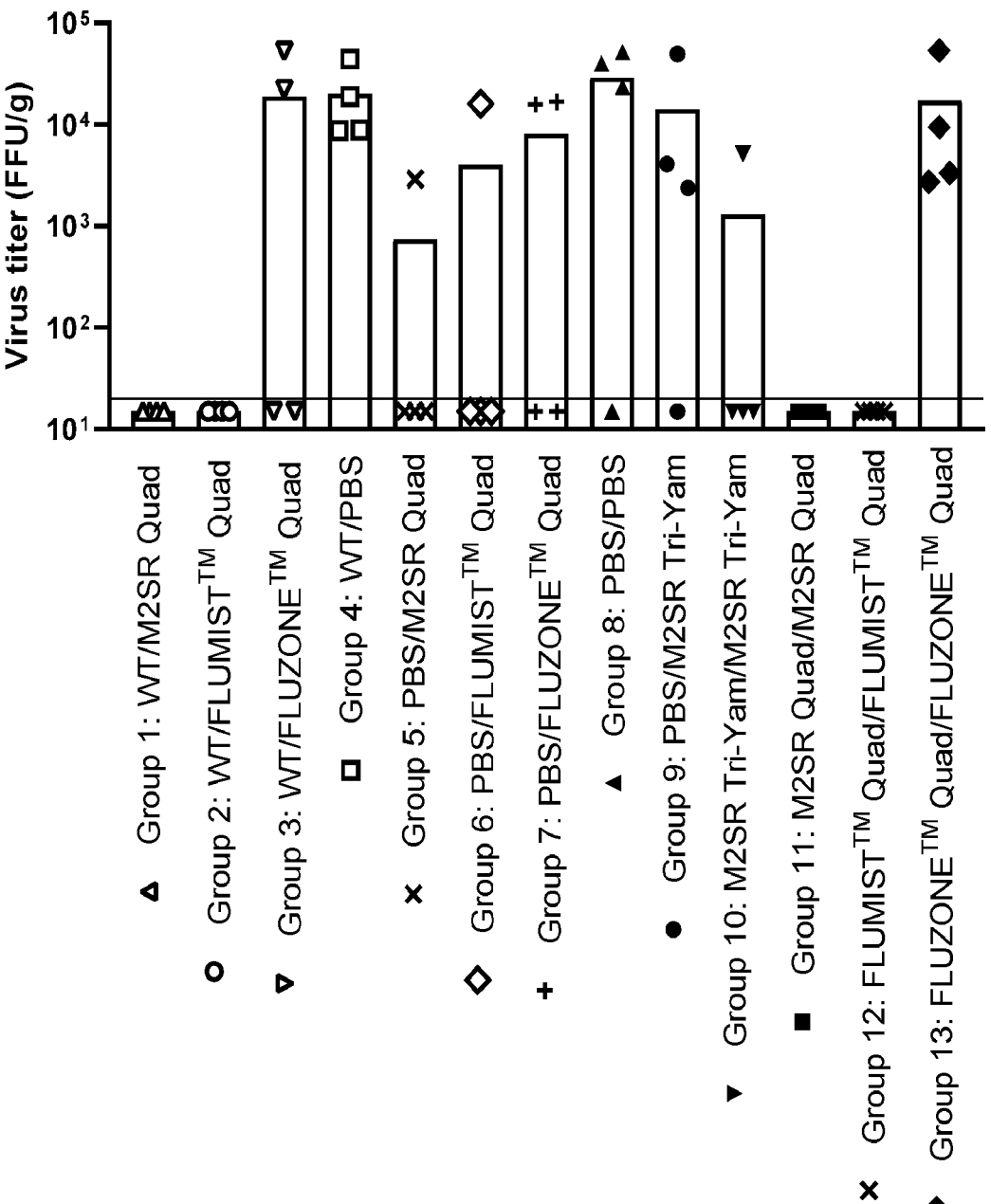

FIG. 16 is a graph depicting the challenge virus titers in nasal turbinates on day 3 post-challenge with influenza B/Vic as described in Example 14. Average titers per group are plotted. Detection limit was 1.3 log FFU/g.

Figure 17:
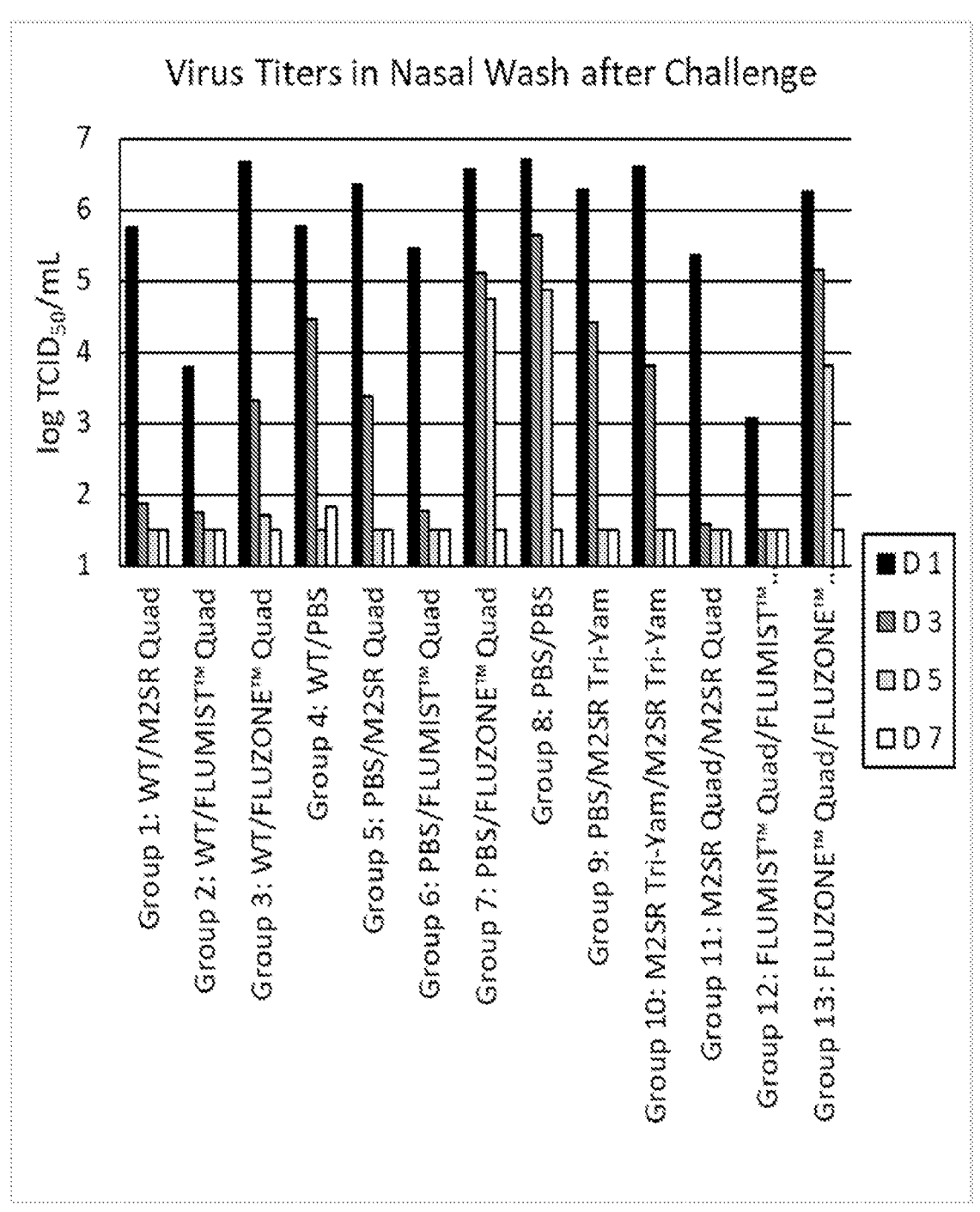

FIG. 17 is a graph depicting the challenge virus titers in nasal wash on days 1, 3, 5, and 7 after challenge with influenza B/Vic as described in Example 14. Average titers per group are plotted. Detection limit was 1.6 log $TCID_{50}$/mL.

Figure 18A:
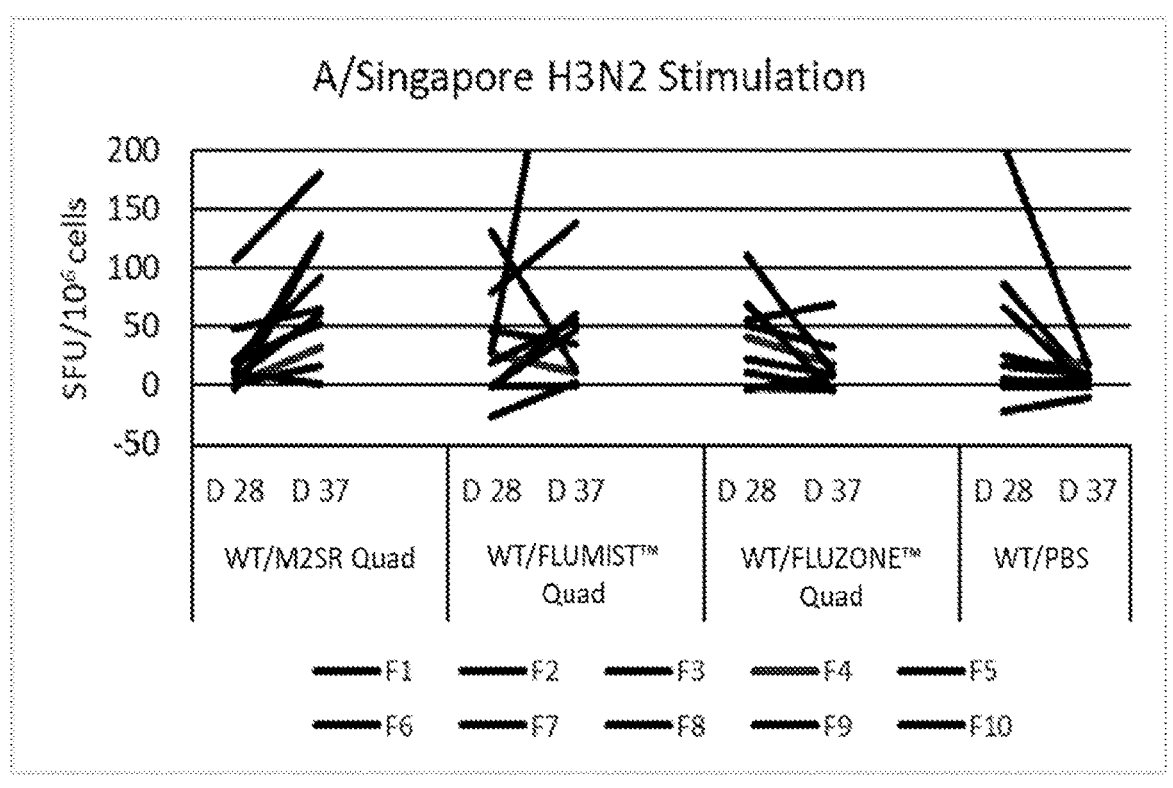

FIG. 18A is a graph depicting the frequency (spot forming unit per $10^6$ cells) of PBMCs producing IFN-$\gamma$ following A/Singapore/INFIMH-16-0019/2016 virus stimulation of cells harvested on days 28 and 37 post vaccination.

Figure 18B:
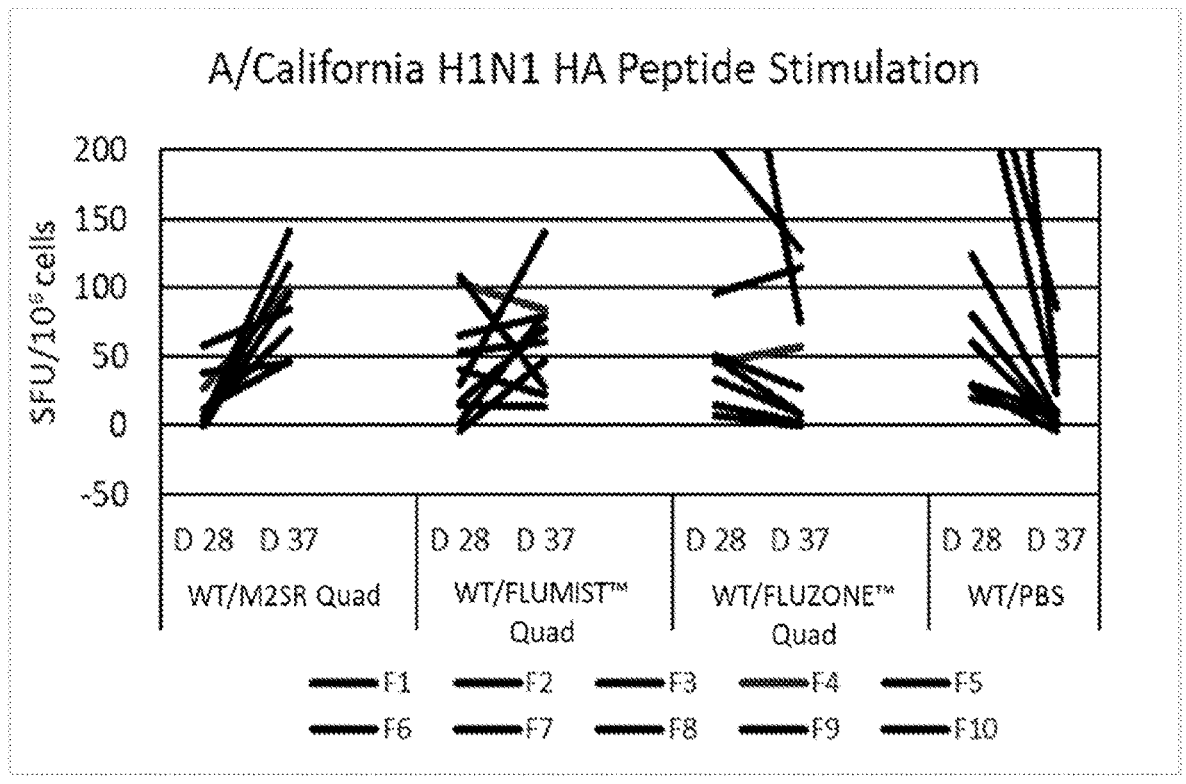

FIG. 18B is a graph depicting the frequency (spot forming unit per $10^6$ cells) of PMBCs producing IFN-$\gamma$ following A/California/07/2009 HA peptide pool stimulation of cells harvested on days 28 and 37 post vaccination.

FIG. 19A is a graph depicting the average percent body weight changes in each ferret group following challenge with influenza B/Vic.

Figure 19B:
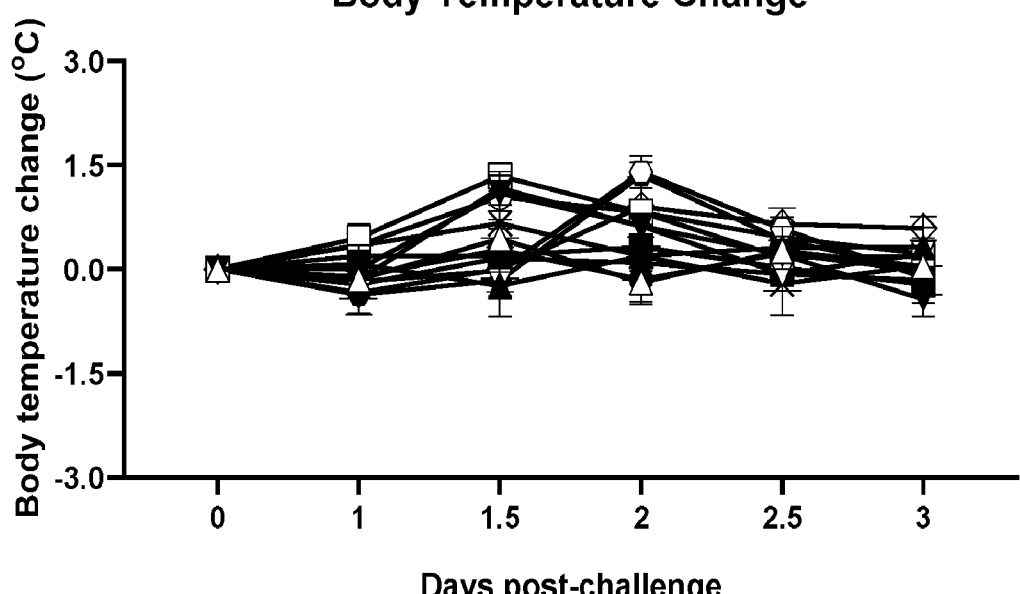

FIG. 19B is a graph depicting the average body temperature change in each ferret group following challenge with influenza B/Vic.

DETAILED DESCRIPTION OF THE INVENTION

The influenza virus of the invention may be any type of influenza virus. For example, the influenza virus may be any subtype of Influenza B (e.g., Victoria or Yamagata). In some embodiments, the influenza virus may be a seasonal Influenza B virus. In some embodiments, the influenza virus may be a recombinant influenza virus. As used herein, a recombinant influenza virus (e.g., a reassortant influenza virus) is an influenza virus comprising genetic material (e.g., gene segments) derived from a genetically distinct, i.e., different, influenza virus (e.g., heterologous gene segments). The influenza virus may also be an isolated influenza virus.

As used herein, the term "gene segment" refers to the nucleotide sequence that encodes a viral protein. The gene segment may be represented by the cDNA (complementary DNA) sequence encoding the viral RNA (vRNA), i.e., SEQ ID NOs: 8-12 and 18, that encodes the viral protein or proteins.

As used herein, the term "backbone" refers to the influenza gene segments encoding the PB1, PB2, PA, NP, NS1 and/or NS2, and M proteins. The gene segments of the invention encode proteins that can have selected amino acids.

As used herein, the term "selected amino acid" refers to a specific amino acid in a particular position of an amino acid sequence. In some embodiments, the selected amino acid is the result of a genetic mutation to a parent amino acid sequence. The parent amino acid sequence may be identical to the amino acid sequence comprising the selected amino acid, except for the position corresponding to the selected amino acid.

The Influenza Virus (A) Backbone Proteins

In one embodiment of the invention, the influenza virus comprises PA, NP, and NS gene segments, wherein (a) the PA gene segment comprises a thymine at nucleotide position 2272; (b) the NP gene segment encodes a NP protein having an amino acid sequence comprising selected amino acids, wherein the selected amino acids comprise a serine at position 40, an asparagine or glycine at position 161, a threonine at position 204, and optionally a valine at position 93; and (c) the NS gene segment comprises a guanine at nucleotide position 39, and wherein the NS gene segment encodes an NS1 protein having an amino acid sequence comprising selected amino acids, wherein the selected amino acids comprise a glutamine at position 176.

The PB1 (polymerase basic protein 1) gene segment of the invention may encode a protein, i.e., a PB1 protein, comprising at least one selected amino acid. The selected amino acids may be acquired by genetic mutation to a parent PB1 sequence, e.g., a sequence identical to the PB1 amino acid sequence of the invention, except for the positions corresponding to the selected amino acids. The PB2 (polymerase basic protein 2) gene segment of the invention may also encode a protein, i.e., a PB2 protein, comprising at least one selected amino acid.

The PA (polymerase acidic protein) gene segment of the invention may also encode a protein, i.e., a PA protein, comprising at least one selected amino acid. In a preferred embodiment, the gene segment comprises a thymine at nucleotide position 2272.

The NP (nucleoprotein) gene segment of the invention may also encode a protein, i.e., an NP protein, comprising at least one selected amino acid. In a preferred embodiment, the NP segment comprises a thymine at position 177, an adenine at position 540 and a thymine at position 670 and the NP gene segment encodes a protein having selected amino acids comprise a serine at position 40, an asparagine or glycine at position 161, a threonine at position 204, and optionally a valine at position 93.

The NS (non-structural) gene segment of the invention may also encode a protein, i.e., an NS1 and/or NS2 protein, comprising at least one selected amino acid. In a preferred embodiment, the NS segment comprises a guanine at nucleotide position 39 and a cytosine at position 570, and the NS gene segment encodes an NS protein having selected amino acids comprising a glutamine at position 176 (NS1 protein).

In one embodiment of the invention, the influenza virus comprises a PB1 gene segment encoding a protein, i.e., a PB1 protein, having selected amino acids. The PB1 gene segment may have a nucleotide sequence represented by SEQ ID NO: 8. The PB1 gene segment may encode a protein, i.e., a PB1 protein, having an amino acid sequence of SEQ ID NO: 13. In another aspect of the embodiment, the influenza virus may comprise a PB2 gene segment encoding a protein, i.e., a PB2 protein, having selected amino acids. The PB2 gene segment may have a nucleotide sequence represented by SEQ ID NO: 9. The PB2 gene segment may encode a protein, i.e., a PB2 protein, having an amino acid sequence of SEQ ID NO: 14. In another aspect of the embodiment, the influenza virus may comprise a NP gene segment encoding a protein, i.e., a NP protein, having selected amino acids at positions 40, 161, and 204, i.e., a serine at position 40, an asparagine or glycine at position 161, a threonine at position 204, and optionally a valine at position 93. The NP gene segment may have a nucleotide sequence represented by SEQ ID NO: 11. The NP gene segment may encode a protein, i.e., an NP protein, having an amino acid sequence of SEQ ID NO: 16. In another aspect of the embodiment, the influenza virus may comprise a NS gene segment encoding a protein, i.e., a NS1 and/or NS2 protein, having selected amino acids at position 176, i.e., a glutamine at position 176. The NS gene segment may comprise a guanine at nucleotide position 39 and cytosine at position 570. The NS gene segment may have a nucleotide sequence represented by SEQ ID NO: 12. The NS gene segment may encode a protein, i.e., an NS1 and/or NS2 protein, having an amino acid sequence of SEQ ID NO: 17. In another aspect of the embodiment, the influenza virus may comprise a PA gene segment encoding a protein, i.e., a PA protein. The PA gene segment may have a nucleotide sequence represented by SEQ ID NO: 10. The PA gene segment may encode a protein, i.e., a PA protein, having an amino acid sequence of SEQ ID NO: 15.

The selected amino acids of the embodiments, particularly in most proteins of the backbone, confer enhanced growth properties onto the influenza virus, as compared to an influenza virus that is the same except without the selected amino acids, under the same conditions. For example, the influenza virus of the invention exhibits enhanced growth in Vero cells.

The influenza virus of the invention may also comprise an M (matrix protein) gene segment. In one embodiment of the invention, the M gene segment may be a mutant gene segment from influenza B, such that the virus lacks expression of functional BM2 protein. Such a virus is herein referred to as a "BM2SR" virus. The BM2SR virus is a single replication influenza B virus. The M gene segment of the BM2SR virus may be represented by SEQ ID NO: 18. The M gene segment may encode a protein, e.g., a truncated BM2 protein, having the amino acid sequence of SEQ ID NO: 20. The BM2SR virus may be propagated in Vero cells that stably express the BM2 protein (i.e., BM2Vero cells) to allow for multicycle replication. High yield in Vero cells is not dependent on mutation in the M gene segment. Therefore, the influenza virus of the invention may comprise an M gene segment that encodes a functional M2 protein.

(B) Surface Proteins

In a further embodiment of the invention, the influenza virus comprises an NA (neuraminidase) and HA (hemagglutinin) gene segment. In one embodiment of the invention, the HA gene segment may encode a HA protein having an amino acid sequence comprising at least one selected amino acid (e.g., an amino acid mutation) in the HA1 subunit of the protein and/or at least one selected amino acid (e.g., amino acid mutation) in the HA2 subunit of the protein. For example, the at least one amino acid mutation in the HA2 subunit may be a glutamic acid at position 61. In another embodiment, the at least one amino acid mutation in the HA2 subunit may be glutamic acid at position 112. The amino acid mutations may be present in any of the subtypes or lineages of influenza B virus (i.e., Victoria or Yamagata). In a preferred embodiment, the amino acid mutation in the HA2 subunit may be glutamic acid at position 61 in the Victoria lineage of influenza B virus. In another preferred embodiment, the amino acid mutation in the HA2 subunit may be glutamic acid at position 112 in the Yamagata lineage of the influenza B virus. Such mutations may also contribute to enhanced growth of the virus during production.

In one embodiment of the invention, PA, NP, and NS gene segments are derived from a single influenza strain. In another embodiment of the invention, the PB1, PB2, PA, NP, and NS gene segments are derived from a single influenza strain. In one embodiment, the HA gene segment may be derived from an influenza strain different from the single influenza strain from which the PA, NP, and NS gene segments are derived. In another embodiment, the HA gene segment may be derived from an influenza strain different from the single influenza strain from which the PB1, PB2, PA, NP, and NS gene segments are derived. Likewise, the NA gene segment may be derived from an influenza strain different from the single influenza strain from which the PA, NP, and NS gene segments are derived. In another embodiment, the NA gene segment may be derived from an influenza strain different from the single influenza strain from which the PB1, PB2, PA, NP, and NS gene segments are derived. Accordingly, the influenza virus of the invention may be a seasonal influenza virus (e.g., Influenza B).

(C) Properties of the Influenza Virus

The backbone of the inventive influenza virus confers high growth properties onto influenza viruses, particularly in Vero cells, regardless of the type of influenza virus. The inventive influenza virus exhibits high yields even in manufacturing processes using low multiplicity of infection (MOI) (e.g., 0.001). MOI refers to the average number of agent (e.g., virus) per infection target (e.g., cell). A lower MOI is used when multiple cycles of infection are required (e.g., virus vaccine production). Current Good Manufacturing Practice regulations are enforced by the FDA and generally necessitate use of the lowest MOI that still produces high yields of the virus. This is because master seed stocks are costly, and toxicity resulting from noninfectious particles and excess cellular proteins can decrease virus production.

In a further embodiment of the invention, the influenza virus is genetically stable, such that the selected amino acids of the backbone proteins, particularly the PB1, PB2, PA, NP, and NS1 proteins, are highly conserved, even when propagated at low MOI. For example, in one embodiment of the invention, the selected amino acids are conserved in at least one of the PB1, PB2, NP, and NS proteins after at least one, at least two, at least three, at least four, at least five, at least six, at least seven, at least eight, at least nine, at least ten, or more than ten serial passages in a Vero cell line. In one embodiment, the Vero cell line may comprise Vero cells that stably express the BM2 ion channel protein of Influenza B virus (i.e., BM2Vero cells). In a preferred embodiment of the invention, the selected amino acids are conserved in at least one of the NP and NS proteins after at least ten serial passages in a Vero cell line that stably expresses the BM2 ion channel protein of influenza B virus. BM2 is considered to be a functional counterpart to Influenza A virus M2. In such an embodiment, the selected amino acids may be conserved even when the influenza virus is an influenza A virus.

Genetically modified Vero cells (i.e., those that express influenza M2 or BM2 proteins) behave like normal Vero cells and support growth of influenza A or B viruses comparable to normal Vero cells. Virus titers for M2SR viruses in M2VeroA cells are comparable to replicating influenza viruses that express functional M2 in unmodified Vero cell lines. Further, virus titers for BM2SR viruses (i.e., influenza viruses that comprise a mutant M gene segment from Influenza B and consequently do not express a functional BM2 protein) in BM2Vero cells are comparable to replicating influenza viruses that express functional BM2 in unmodified Vero cell lines. Accordingly, M2SR and BM2SR viruses behave like replicating influenza viruses in the M2VeroA and BM2Vero cell lines.

In one embodiment of the invention, the influenza virus is capable of replication in human cells.

Method of Generating the Influenza Virus

Also provided herewith is a method of generating an influenza virus, wherein, in one embodiment, the generated influenza virus comprises PA, NP, and NS gene segments that express proteins having selected amino acids, i.e., the recombinant influenza virus of the invention as disclosed herein. In another embodiment, the generated influenza virus comprises PB1, PB2, NP, and NS gene segments that express proteins having selected amino acids, i.e., another embodiment of the invention as disclosed herein.

In one embodiment of the inventive method, the method of generating the recombinant influenza virus comprises serially passaging a recombinant influenza virus (e.g., a first influenza virus) in Vero cells to generate the generated influenza virus (e.g., a second influenza virus). The first influenza virus may comprise PA, NP, and NS gene segments that express proteins, i.e., PA, NP, and NS1 proteins having selected amino acids, as described with respect to the inventive influenza virus. For example, the first influenza virus may comprise a PA gene segment comprising a thymine at nucleotide position 2272. The PA gene segment may encode a protein, i.e., a PA protein. The NP gene segment of the first influenza virus may comprise a thymine at position 177, an adenine at position 540, and a thymine at position 670 and encode a protein, i.e., a NP protein, comprising a serine at position 40, an asparagine or glycine at position 161, a threonine at position 204, and optionally a valine at position 93. The NS gene segment of the first influenza virus may comprise a guanine at nucleotide position 39 and encode a protein, i.e., and NS1 and/or NS2 protein, comprising a glutamine at position 176. In one embodiment of the invention, the second influenza virus (e.g., the generated influenza virus) is generated after at least four or at least five serial passages of the first influenza virus in Vero cells. The first influenza virus may further comprise PB1 and PB2 gene segments that express proteins, i.e., PB1 and PB2 proteins having selected amino acids, as described with respect to the inventive influenza virus.

The influenza virus of the invention may also be generated using standard virus rescue techniques. For example, in one embodiment of the invention, one or more plasmids into which cDNAs for each of the eight viral gene segments (i.e., PB1, PB2, PA, NP, M, NS, HA, and NA) are cloned are transfected into eukaryotic host cells, wherein each cDNA sequence is flanked by an RNA polymerase I promoter and an RNA polymerase I terminator (i.e., pPolI plasmids). The gene segments encoding the PB1, PB2, PA, NP, and NS1 and/or NS2 proteins may encode proteins having the selected amino acids of the invention. The gene segment encoding the M2 or BM2 protein may comprise the mutant M2 or BM2 gene segment, such that the gene segment does not encode functional M2 or BM2. The host cell may also be transfected with one or more expression plasmids encoding the viral proteins (e.g., at least one or more of the PA, PB1, PB2, and NP proteins, or at least one or more of the PB1, PB2, PA, NP, M, NS1 and/or NS2, HA, and NA proteins). The eight influenza vRNAs (i.e., gene segments) are then synthesized after transfection of at least one or more plasmids into the host cell. The co-transfected viral polymerases and nucleoproteins assemble the vRNAs into functional vRNPs (i.e., viral ribonucleoprotein complexes) that are replicated and transcribed, ultimately forming the recombinant influenza virus of the invention. This plasmid-based reverse genetics system is further detailed by Neumann et al., *PNAS*, 96: 9345-9350 (1999). The influenza virus of the invention may also be generated using other methods known in the art, such as, but not limited to, a ribonucleoprotein (RNP) transfection system, as described in U.S. Pat. No. 9,284,533 (incorporated herein by reference).

Pharmaceutical Formulation

The invention provides a pharmaceutical formulation (e.g., a vaccine or other immunogenic composition) comprising the inventive recombinant virus as described herein.

The pharmaceutical formulation can further comprise at least one pharmaceutically acceptable carrier or excipient. As used herein, the term "pharmaceutically acceptable carrier or excipient" refers to any component of the pharmaceutical formulation other than the inventive influenza virus. The pharmaceutically acceptable carrier or excipient can enhance efficacy of the inventive recombinant virus or maintain stability of the pharmaceutical formulation, desirably without significantly inactivating the inventive recombinant virus.

The at least one pharmaceutically acceptable carrier or excipient may be any suitable pharmaceutically acceptable carrier or excipient, many of which are known in the art. Exemplary pharmaceutically acceptable carriers or excipients include components that maintain a pH of the pharmaceutical formulation (e.g., buffers), adjust tonicity (e.g., tonicity modifying agents such as an inorganic salt), improve protein (e.g., virus) stability and/or immunogenicity, improve mucoadhesion, prevent protein aggregation, and/or preserve the pharmaceutical formulation (e.g., preservatives). For example, the pharmaceutically acceptable carrier or excipient may comprise at least one of an inorganic salt, surfactant, amino acid, polymer or polymeric compound (e.g., protein, polysaccharide, or hydrogel), chelating agent, sugar, polyol, and/or adjuvant (e.g., any substance that augments a specific immune response), many of which are known in the art. A particular carrier or excipient may serve more than one purpose in the pharmaceutical formulation, and, thus, the following embodiments are not limited to the descriptions recited herein.

Any suitable buffer can be present in the pharmaceutical formulation. In one embodiment, the buffer comprises at least one of an imidazole buffer, a potassium phosphate buffer, phosphate-buffered saline (PBS), Dulbecco's phosphate-buffered saline (DPBS) (e.g., 1×DPBS), a histidine buffer, a sodium citrate buffer, and sucrose phosphate glutamate buffer (SPG). PBS and/or DPBS preparations may comprise, for example, sodium chloride, potassium chloride, potassium phosphate monobasic, and sodium phosphate dibasic, and may optionally further comprise calcium chloride and/or magnesium chloride. In some embodiments, the PBS and/or DPBS preparations comprise about 136.9 mM sodium chloride, about 2.67 mM potassium chloride, about 1.47 mM potassium phosphate monobasic, and about 8.1 mM sodium phosphate dibasic, although any suitable PBS and/or DPBS preparation, many of which are known in the art, may be used as a buffer in the pharmaceutical formulation.

The buffer can be present in the pharmaceutical formulation in any suitable concentration. The buffer can be present in the pharmaceutical formulation at a concentration of about 0.1 mM or more, about 1 mM or more, about 10 mM or more, about 20 mM or more, about 30 mM or more, about 40 mM or more, about 50 mM or more, about 60 mM or more, about 70 mM or more, about 80 mM or more, about 90 mM or more, about 100 mM or more, about 120 mM or more, about 140 mM or more, about 160 mM or more, about 180 mM or more, about 200 mM or more, about 250 mM or more, about 300 mM or more, about 350 mM or more, about 400 mM or more, about 450 mM or more, or about 500 mM or more. Alternatively, or in addition, the buffer can be present in the pharmaceutical formulation at a concentration of about 1,000 mM or less, about 500 mM or less, about 450 mM or less, about 400 mM or less, about 350 mM or less, about 300 mM or less, about 250 mM or less, about 200 mM or less, about 180 mM or less, about 160 mM or less, about 140 mM or less, about 120 mM or less, about 100 mM or less, about 90 mM or less, about 80 mM or less, about 70 mM or less, about 60 mM or less, about 50 mM or less, about 40 mM or less, about 30 mM or less, about 20 mM or less, about 10 mM or less, or about 1 mM or less. The buffer can be present in the pharmaceutical formulation at any concentration within a range bounded by any of the aforementioned endpoints. For example, the buffer can be present in the pharmaceutical formulation at a concentration of about 0.1 mM to about 1000 mM, about 0.1 mM to about 500 mM, about 0.1 mM to about 100 mM, about 1 mM to about 1000 mM, about 1 mM to about 500 mM, about 1 mM to about 100 mM, about 100 mM to about 1000 mM, about 100 mM to about 500 mM, and the like.

In further embodiments, the buffer is present in the pharmaceutical formulation at a percentage concentration (e.g., volume/volume percentage (% v/v); weight/volume percentage (% w/v); or weight/weight percentage (% w/w)). The buffer can be present in the pharmaceutical formulation at a percentage concentration of about 0.1% or more, about 1% or more, about 5% or more, about 10% or more, about 15% or more, about 20% or more, about 30% or more, about 40% or more, or about 50% or more. Alternatively, or in addition, the buffer can be present in the pharmaceutical formulation at a percentage concentration of about 60% or less, about 50% or less, about 40% or less, about 30% or less, about 20% or less, about 15% or less, about 10% or less, about 5% or less, or about 1% or less. The buffer can be present in the pharmaceutical formulation at any percentage concentration within a range bounded by any of the foregoing endpoints. For example, the buffer can be present in the pharmaceutical formulation at a percentage concentration of about 0.1% to about 60%, about 1% to about 60%, about 10% to about 60%, about 0.1% to about 50%, about 1% to about 50%, about 10% to about 50%, about 20% to about 60%, about 20% to about 50%, about 20% to about 40%, about 20% to about 30%, about 30% to about 40%, about 40% to about 50%, and the like.

The buffer can maintain the pH of the pharmaceutical formulation at any suitable pH. The buffer can maintain the pH of the pharmaceutical formulation at a pH of, for example, about 4 or higher, about 4.5 or higher, about 5 or higher, about 5.5 or higher, about 6 or higher, about 6.5 or higher, about 7 or higher, or about 7.5 or higher. Alternatively, or in addition, the buffer can maintain the pH of the pharmaceutical formulation at a pH of, for example, about 8 or lower, about 7.5 or lower, about 7 or lower, about 6.5 or lower, about 6 or lower, about 5.5 or lower, about 5 or lower, or about 4.5 or lower. The buffer can maintain the pH of the pharmaceutical formulation at a pH within a range bounded by any of the foregoing endpoints. For example, the buffer can maintain the pH of the pharmaceutical formulation at a pH of about 4 to about 8, about 4.5 to about 8, about 5 to about 8, about 5.5 to about 8, about 6 to about 8, about 6.5 to about 8, about 7 to about 8, about 7.5 to about 8, about 4 to about 7.5, about 5 to about 7.5, about 6 to about 7.5, about 7 to about 7.5, about 4 to about 7, about 5 to about 7, about 6 to about 7, and the like.

Any suitable tonicity modifying agent can be present in the pharmaceutical formulation. In certain embodiments, one or more inorganic salts are present in the pharmaceutical formulation as tonicity modifying agents. The inorganic salt(s) may be at least one of sodium chloride (NaCl), magnesium sulfate ($MgSO_4$), and magnesium chloride ($MgCl_2$). The tonicity modifying agent, e.g., inorganic salt(s), can be present in the pharmaceutical formulation in any suitable amount. The tonicity modifying agent, e.g., inorganic salt(s), can be present in the pharmaceutical formulation at a concentration of about 0.1 mM or more, about 0.2 mM or more, about 0.4 mM or more, about 0.6 mM or more, about 0.8 mM or more, about 1 mM or more, about 1.2 mM or more, about 1.4 mM or more about 1.6 mM or more, about 1.8 mM or more, about 2 mM or more, about 3 mM or more, about 4 mM or more, about 5 mM or more, about 6 mM or more, about 7 mM or more, about 8 mM or more, about 9 mM or more, about 10 mM or more, about 20 mM or more, about 30 mM or more, about 40 mM or more, about 50 mM or more, about 100 mM or more, about 200 mM or more, about 300 mM or more, about 400 mM or more, about 500 mM or more, about 600 mM or more, about 700 mM or more, about 800 mM or more, about 900 mM or more, about 1000 mM or more, or about 1500 mM or more. Alternatively, or in addition, the tonicity modifying agent, e.g., inorganic salt(s), can be present in the pharmaceutical formulation at a concentration of about 2000 mM or less, about 1500 mM or less, about 1000 mM or less, about 900 mM or less, about 800 mM or less, about 700 mM or less, about 600 mM or less, about 500 mM or less, about 450 mM or less, about 400 mM or less, about 350 mM or less, about 300 mM or less, about 250 mM or less, about 200 mM or less, about 150 mM or less, about 100 mM or less, about 50 mM or less, about 45 mM or less, about 40 mM or less, about 35 mM or less, about 30 mM or less, about 25 mM or less, about 20 mM or less, about 10 mM or less, about 9 mM or less, about 8 mM or less, about 7 mM or less, about 6 mM or less, about 5 mM or less, about 4 mM or less, about 3 mM or less, about 2 mM or less, about 1.8 mM or less, about 1.6 mM or less, about 1.4 mM or less, about 1.2 mM or less, about 1 mM or less, about 0.8 mM or less, about 0.6 mM or less, about 0.4 mM or less, or about 0.2 mM or less. The tonicity modifying agent, e.g., inorganic salt(s), can be present in the pharmaceutical formulation at any concentration within a range bounded by any of the aforementioned endpoints. For example, the tonicity modifying agent, e.g., inorganic salt(s), can be present in the pharmaceutical formulation at a concentration of about 0.1 mM to about 2000 mM, about 0.1 mM to about 1500 mM, about 0.1 mM to about 1000 mM, about 0.1 mM to about 500 mM, about 0.1 mM to about 250 mM, about 0.1 mM to about 100 mM, about 0.1 to about 50 mM, about 0.1 mM to about 10 mM, about 1 mM to about 2000 mM, about 1 mM to about 1500 mM, about 1 mM to about 1000 mM, about 1 mM to about 500 mM, about 1 mM to about 250 mM, about 1 mM to about 100 mM, about 1 mM to about 50 mM, about 1 mM to about 10 mM, about 10 mM to about 2000 mM, about 10 mM to about 1500 mM, about 10 mM to about 1000 mM, about 10 mM to about 500 mM, about 10 mM to about 250 mM, about 10 mM to about 100 mM, about 10 mM to about 50 mM, about 100 mM to about 2000 mM, about 100 mM to about 1500 mM, about 100 mM to about 1000 mM, about 100 mM to about 500 mM, about 100 mM to about 250 mM, about 500 mM to about 2000 mM, about 500 mM to about 1500 mM, about 500 mM to about 1000 mM, and the like.

In further embodiments, the inorganic salt is present in the pharmaceutical formulation at a percentage concentration (e.g., volume/volume percentage (% v/v); weight/volume percentage (% w/v); or weight/weight percentage (% w/w)). The tonicity modifying agent, e.g., inorganic salt(s), be present in the pharmaceutical formulation at a percentage concentration of about 0.1% or more, about 1% or more, about 2% or more, about 3% or more, about 4% or more, about 5% or more, about 6% or more, about 7% or more, about 8% or more, about 9% or more, or about 10% or more. Alternatively, or in addition, the tonicity modifying agent, e.g., inorganic salt(s), can be present in the pharmaceutical formulation at a percentage concentration of about 10% or less, about 9% or less, about 8% or less, about 7% or less, about 6% or less, about 5% or less, about 4% or less, about 3% or less, about 2% or less, or about 1% or less. The tonicity modifying agent, e.g., inorganic salt(s), can be present in the pharmaceutical formulation at any percentage concentration within a range bounded by any of the foregoing endpoints. For example, the tonicity modifying agent, e.g., inorganic salt(s), can be present in the pharmaceutical formulation at a percentage concentration of about 0.1% to about 1%, about 0.1% to about 2%, about 0.1% to about 5%, about 0.1% to about 10%, about 1% to about 2%, about 1% to about 5%, about 1% to about 10%, about 2% to about 10%, about 3% to about 10%, about 4% to about 10%, about 5% to about 10%, and the like.

Any suitable surfactant can be present in the pharmaceutical formulation. In certain embodiments, the surfactant can comprise at least one of polysorbate 20, polysorbate 80, sodium deoxycholate, and poloxamer 188. The surfactant can be present in the pharmaceutical formulation in any suitable amount. In some embodiments, the surfactant is present in the pharmaceutical formulation at a percent concentration (e.g., volume/volume percentage (% v/v); weight/volume percentage (% w/v); or weight/weight percentage (% w/w)). The surfactant can be present in the pharmaceutical formulation at a percentage concentration of about 0.01% or more, about 0.02% or more, about 0.03% or more, about 0.04% or more, about 0.05% or more, about 0.06% or more, about 0.07% or more, about 0.08% or more, about 0.09% or more, about 0.1% or more, about 0.2% or more, about 0.3% or more, about 0.4% or more, about 0.5% or more, about 0.6% or more, about 0.7% or more, about 0.8% or more, about 0.9% or more, or about 1% or more. Alternatively, or in addition, the surfactant can be present in the pharmaceutical formulation at a percentage concentration of about 1% or less, about 0.9% or less, about 0.8% or less, about 0.7% or less, about 0.6% or less, about 0.5% or less, about 0.4% or less, about 0.3% or less, about 0.2% or less, or about 0.1% or less. The surfactant can be present in the pharmaceutical formulation at any percentage concentration within a range bounded by any of the foregoing endpoints. For example, the surfactant can be present in the pharmaceutical formulation at a percentage concentration of about 0.01% to about 1%, about 0.01% to about 0.1%, about 0.05% to about 1%, about 0.05% to about 0.1%, about 0.1% to about 1%, about 0.1% to about 0.5%, about 0.2% to about 1%, about 0.5% to about 1%, and the like.

Any suitable amino acids can be present in the pharmaceutical formulation. In certain embodiments, the amino acid may be one or more of arginine, glutamic acid or glutamate, asparagine, histidine, and glycine. The amino acid(s) can be present in the pharmaceutical formulation in any suitable amount. The amino acid(s) can be present in the pharmaceutical formulation at a concentration of about 1 mM or more, about 2 mM or more, about 3 mM or more, about 5 mM or more, about 6 mM or more, about 7 mM or more, about 8 mM or more, about 9 mM or more, or about 10 mM or more. Alternatively, or in addition, the amino acid(s) can be present in the pharmaceutical formulation at a concentration of about 100 mM or less, about 90 mM or less, about 80 mM or less, about 70 mM or less, about 60 mM or less, about 50 mM or less, about 40 mM or less, about 30 mM or less, about 20 mM or less, or about 10 mM or less. The amino acid(s) can be present in the pharmaceutical formulation at any concentration within a range bounded by any of the foregoing endpoints. For example, the amino acid(s) can be present in the pharmaceutical formulation at a concentration of about 1 mM to about 10 mM, about 1 mM to about 50 mM, about 1 mM to about 100 mM, about 5 mM to about 50 mM, about 10 mM to about 50 mM, about 20 mM to about 50 mM, and the like.

In some embodiments, the amino acid(s) is present in the pharmaceutical formulation at a percentage concentration (e.g., volume/volume percentage (% v/v); weight/volume percentage (% w/v); or weight/weight percentage (% w/w)). The amino acid(s) can be present in the pharmaceutical formulation at a percentage concentration of about 0.1% or more, about 0.2% or more, about 0.3% or more, about 0.4% or more, about 0.5% or more, about 0.6% or more, about 0.7% or more, about 0.8% or more, about 0.9% or more, about 1% or more, about 2% or more, about 3% or more, about 4% or more, or about 5% or more. Alternatively, or in addition, the amino acid(s) can be present in the pharmaceutical formulation at a percentage concentration of about 10% or less, about 9% or less, about 8% or less, about 7% or less, about 6% or less, about 5% or less, about 4% or less, about 3% or less, about 2% or less, or about 1% or less. The amino acid(s) can be present in the pharmaceutical formulation at any percentage concentration within a range bounded by any of the foregoing endpoints. For example, the amino acid(s) can be present in the pharmaceutical formulation at a percentage concentration of about 0.1% to 10%, 0 about. 2% to about 10%, about 0.5% to about 10%, about 0.1% to about 5%, about 0.1% to about 2%, about 0.2% to about 2%, about 0.5% to about 1%, and the like.

Any suitable polymers or polymeric compounds can be present in the pharmaceutical formulation. The polymer or polymeric compound can be, for example, a protein, a polysaccharide, a hydrogel, or any other suitable polymer or polymeric compound, many of which are known in the art. For example, the polymer or polymeric compound can be recombinant human serum albumin (rHSA), serum albumin (SA), gelatin, hydroxyethyl starch (HES), chitosan, dextran (DEX70K, DEX40K), and polyvinylpyrrolidone (PVP40K).

The polymer(s) or polymeric compound(s) can be present in the pharmaceutical formulation in any suitable amount. The polymer(s) or polymeric compound(s) can be present in the pharmaceutical formulation at a percentage concentration (e.g., volume/volume percentage (% v/v); weight/volume percentage (% w/v); or weight/weight percentage (% w/w)). The polymer(s) or polymeric compound(s) can be present in the pharmaceutical formulation at a percentage concentration of about 0.1% or more, about 0.2% or more, about 0.3% or more, about 0.4% or more, about 0.5% or more, about 0.6% or more, about 0.7% or more, about 0.8% or more, about 0.9% or more, about 1% or more, about 2% or more, about 3% or more, about 4% or more, or about 5% or more. Alternatively, or in addition, the polymer(s) or polymeric compound(s) can be present in the pharmaceutical formulation at a percentage concentration of about 10% or less, about 9% or less, about 8% or less, about 7% or less, about 6% or less, about 5% or less, about 4% or less, about 3% or less, about 2% or less, or about 1% or less. The polymer(s) or polymeric compound(s) can be present in the pharmaceutical formulation at any percentage concentration within a range bounded by any of the foregoing endpoints. For example, the polymer(s) or polymeric compound(s) can be present in the pharmaceutical formulation at a percentage concentration of about 0.1% to about 10%, about 0.2% to 1 about 0%, about 0.5% to about 10%, about 0.1% to about 5%, about 0.1% to about 2%, about 0.2% to about 2%, about 0.5 to about 2%, about 0.1% to about 1%, about 0.2% to about 1%, about 0.5% to about 1%, and the like.

Any suitable chelating agent can be present in the pharmaceutical formulation. The chelating agent can be, for example, ethylenediaminetetraacetic acid (EDTA), an amidoxime compound (AOX), and/or dithiothreitol (DTT). The chelating agent can be present in the pharmaceutical formulation at any suitable concentration. The chelating agent can be present in the pharmaceutical formulation at a concentration of 10 μM or more, about 20 μM or more, about 30 μM or more, about 40 μM or more, about 50 μM or more, about 60 μM or more, about 70 μM or more, about 80 μM or more, about 90 μM or more, about 100 μM or more, about 120 μM or more, or about 150 μM or more. Alternatively, or in addition, the chelating agent can be present in the pharmaceutical formulation at a concentration of about 500 μM or less, about 400 μM or less, about 300 μM or less, about 200 μM or less, about 150 μM or less, about 140 μM or less, about 130 μM or less, about 120 μM or less, about 110 μM or less, about 100 μM or less, about 80 μM or less, about 70 μM or less, about 60 μM or less, or about 50 μM or less. The chelating agent can be present in the pharmaceutical formulation at any concentration within a range bounded by any of the foregoing endpoints. For example, the chelating agent can be present in the pharmaceutical formulation at a concentration of about 10 μM to about 500 μM, about 10 μM to about 200 μM, about 10 μM to about 150 μM, about 10 μM to about 100 μM, about 50 μM to about 500 μM, about 50 μM to about 200 μM, about 50 μM to about 150 μM, about 50 μM to about 100 μM, and the like.

Any suitable sugar can be present in the pharmaceutical formulation. The sugar can be, for example, one or more of sucrose, trehalose, mannose, and lactose. The sugar(s) can be present in the pharmaceutical formulation at any suitable concentration. The sugar(s) can be present in the pharmaceutical formulation at a concentration of about 0.1 mM or more, about 0.2 mM or more, about 0.4 mM or more, about 0.6 mM or more, about 0.8 mM or more, about 1 mM or more, about 1.2 mM or more about 1.4 mM or more about 1.6 mM or more about 1.8 mM or more, about 2 mM or more about 3 mM or more about 4 mM or more, about 5 mM or more, about 6 mM or more, about 7 mM or more, about 8 mM or more, about 9 mM or more, about 10 mM or more, about 20 mM or more, about 30 mM or more, about 40 mM or more, about 50 mM or more, about 60 mM or more, about 70 mM or more, about 80 mM or more, about 90 mM or more, or about 100 mM or more, about 200 mM or more, about 300 mM or more, about 400 mM or more, about 500 mM or more, about 600 mM or more, about 700 mM or more, about 800 mM or more, about 900 mM or more, about 1000 mM or more, or about 1500 mM or more. Alternatively, or in addition, the sugar(s) can be present in the pharmaceutical formulation at a concentration of about 2000 mM or less, about 1500 mM or less, about 1000 mM or less, about 900 mM or less, about 800 mM or less, about 700 mM or less, about 600 mM or less, about 500 mM or less, about 450 mM or less, about 400 mM or less, about 350 mM or less, about 300 mM or less, about 250 mM or less, about 200 mM or less, about 150 mM or less, about 100 mM or less, about 50 mM or less, about 45 mM or less, about 40 mM or less, about 35 mM or less, about 30 mM or less, about 25 mM or less, about 20 mM or less, about 10 mM or less, about 9 mM or less, about 8 mM or less, about 7 mM or less, about 6 mM or less, about 5 mM or less, about 4 mM or less, about 3 mM or less, about 2 mM or less, about 1.8 mM or less, about 1.6 mM or less, about 1.4 mM or less, about 1.2 mM or less, about 1 mM or less, about 0.8 mM or less, about 0.6 mM or less, about 0.4 mM or less, or about 0.2 mM or less. The sugar(s) can be present in the pharmaceutical formulation at any concentration within a range bounded by any of the foregoing endpoints. For example, the sugar(s) can be present in the pharmaceutical formulation at a concentration of about 0.1 mM to about 2000 mM, about 0.1 mM to about 1500 mM, about 0.1 mM to about 1000 mM, about 0.1 mM to about 500 mM, about 0.1 mM to about 250 mM, about 0.1 mM to about 100 mM, about 0.1 to about 50 mM, about 0.1 mM to about 10 mM, about 1 mM to about 2000 mM, about 1 mM to about 1500 mM, about 1 mM to about 1000 mM, about 1 mM to about 500 mM, about 1 mM to about 250 mM, about 1 mM to about 100 mM, about 1 mM to about 50 mM, about 1 mM to about 10 mM, about 10 mM to about 2000 mM, about 10 mM to about 1500 mM, v10 mM to about 1000 mM, about 10 mM to about 500 mM, about 10 mM to about 250 mM, about 10 mM to about 100 mM, about 10 mM to about 50 mM, about 100 mM to about 2000 mM, about 100 mM to about 1500 mM, about 100 mM to about 1000 mM, about 100 mM to about 500 mM, about 100 mM to about 250 mM, about 500 mM to about 2000 mM, about 500 mM to about 1500 mM, about 500 mM to about 1000 mM, and the like.

In other embodiments, the sugar(s) is present in the pharmaceutical formulation at a percentage concentration (e.g., volume/volume percentage (% v/v); weight/volume percentage (% w/v); or weight/weight percentage (% w/w)). The sugar(s) can be present in the pharmaceutical formulation at a percentage concentration of about 0.1% or more, about 1% or more, about 5% or more, about 10% or more, about 15% or more, about 20% or more, about 30% or more, about 40% or more. Alternatively, or in addition, the sugar(s) can be present in the pharmaceutical formulation at a percentage concentration of about 50% or less, about 40% or less, about 30% or less, about 20% or less, about 15% or less, about 10% or less, about 5% or less, or about 1% or less. The sugar(s) can be present in the pharmaceutical formulation at any percentage concentration within a range bounded by any of the foregoing endpoints. For example, the sugar(s) can be present in the pharmaceutical formulation at a percentage concentration of about 0.1% to about 50%, about 1% to about 50%, about 10% to about 50%, about 0.1% to about 20%, about 1% to about 20%, about 10% to about 20%, about 0.1% to about 10%, about 1% to about 10%, and the like.

Any suitable polyol can be present in the pharmaceutical formulation. The polyol can be, for example, sorbitol and/or mannitol. The polyol can be present in the pharmaceutical formulation at any suitable concentration. The polyol can be present in the pharmaceutical formulation at a concentration of about 0.1 mM or more, about 1 mM or more, about 10 mM or more, about 20 mM or more, about 30 mM or more, about 40 mM or more, about 50 mM or more, about 60 mM or more, about 70 mM or more, about 80 mM or more, about 90 mM or more, about 100 mM or more, about 120 mM or more, about 140 mM or more, about 160 mM or more, about 180 mM or more, about 200 mM or more, about 250 mM or more, about 300 mM or more, about 350 mM or more, about 400 mM or more, about 450 mM or more, or about 500 mM or more. Alternatively, or in addition, the polyol can be present in the pharmaceutical formulation at a concentration of about 1000 mM or less, about 500 mM or less, about 450 mM or less, about 400 mM or less, about 350 mM or less, about 300 mM or less, about 250 mM or less, about 200 mM or less, about 180 mM or less, about 160 mM or less, about 140 mM or less, about 120 mM or less, about 100 mM or less, about 90 mM or less, about 80 mM or less, about 70 mM or less, about 60 mM or less, about 50 mM or less, about 40 mM or less, about 30 mM or less, about 20 mM or less, about 10 mM or less, or about 1 mM or less. The polyol can be present in the pharmaceutical formulation at any concentration within a range bounded by any of the foregoing endpoints. For example, the polyol can be present in the pharmaceutical formulation at a concentration of about 0.1 mM to about 1000 mM, about 0.1 mM to about 500 mM, about 0.1 mM to about 100 mM, about 1 mM to about 1000 mM, about 1 mM to about 500 mM, about 1 mM to about 100 mM, about 100 mM to about 1000 mM, about 100 mM to about 500 mM, and the like.

In other embodiments, the polyol is present in the pharmaceutical formulation at a percentage concentration (e.g., volume/volume percentage (% v/v); weight/volume percentage (% w/v); or weight/weight percentage (% w/w)). The polyol can be present in the pharmaceutical formulation at a percentage concentration of about 0.1% or more, about 1% or more, about 2% or more, about 3% or more, about 4% or more, or about 5% or more, about 10% or more, about 15% or more, about 20% or more, about 25% or more, about 30% or more, about 35% or more, about 40% or more, about 45% or more. Alternatively, or in addition, the polyol can be present in the pharmaceutical formulation at a percentage concentration of about 50% or less, about 45% or less, about 40% or less, about 35% or less, about 30% or less, about 25% or less, about 20% or less, about 15% or less, about 10% or less, about 5% or less, about 4% or less, about 3% or less, about 2% or less, or about 1% or less. The polyol can be present in the pharmaceutical formulation at any percentage concentration within a range bounded by any of the foregoing endpoints. For example, the polyol can be present in the pharmaceutical formulation at a percentage concentration of about 0.1% to about 50%, about 1% to about 50%, about 5% to about 50%, about 10% to about 50%, about 15% to about 50%, about 0.1% to about 25%, about 1% to about 25%, about 5% to about 25%, about 10% to about 25%, about 15% to about 25%, about 0.1% to about 15%, about 1% to about 15%, about 5% to about 15%, about 10% to about 15%, about 0.1% to about 10%, about 1% to about 10%, about 5% to about 10%, about 0.1% to about 5%, about 1% to about 5%, and the like.

In one embodiment, the pharmaceutical formulation comprises the inventive influenza virus, about 0.5 M sucrose, about 0.1 M or about 0.5 M mannose, about 0.3 M or about 0.5 M trehalose, about 50% SPG, and about 0.05% polysorbate 20. In another embodiment, the pharmaceutical formulation comprises the inventive influenza virus, about 0.5 M sucrose, about 0.3 M trehalose, and about 0.05% polysorbate 20.

The at least one pharmaceutically acceptable carrier or excipient can be a component that serves to bind the ingredients of the pharmaceutical formulation (e.g., a binder). The binder may include, but is not limited to, proteins (e.g., gelatin), polymers (e.g., polyethylene glycol, polyvinylpyrrolidone), and/or polysaccharides or derivatives thereof (e.g., starch and cellulose). The at least one pharmaceutically acceptable carrier or excipient can be a component that increases bulk of the pharmaceutical formulation (e.g., a bulking agent, diluent, and/or filler). Such bulking agents may include, but are not limited to, polysaccharides or derivatives thereof, sugars, and/or inorganic compounds. The pharmaceutically acceptable carrier or excipient can be a component that enhances taste and/or appearance of the pharmaceutical formulation (e.g., a flavor, sweetener, and/or color). The pharmaceutically acceptable carrier or excipient can be a component that moisture-proofs the pharmaceutical formulation by absorbing or adsorbing liquids or gases (e.g., a sorbent). A sorbent includes, but is not limited to, starch, calcium phosphate, and/or colloidal silicon dioxide. The pharmaceutically acceptable carrier or excipient can be a component that promotes dissolution of the pharmaceutical formulation (e.g., a disintegrant), such as a starch, cellulose and/or any other polymer known in the art, or derivative thereof (e.g., cross-linked polyvinylpyrrolidone or sodium carboxymethylcellulose).

In some embodiments, the pharmaceutically acceptable carrier or excipient is a component that reduces interparticle adhesion and/or optimizes product flow in and during manufacture of a pharmaceutical formulation (e.g., a glidant). Examples of glidants include, but are not limited to, talc, colloidal silicon dioxide, and corn starch. The pharmaceutically acceptable carrier or excipient can be a component that provides non-sticking properties, such as reducing adhesion between the ingredients and, for example, the punch faces or lubricant in and during manufacture of a pharmaceutical formulation (e.g., an anti-adherent), particularly when the pharmaceutical formulation is formulated as an oral preparation. For example, the anti-adherent may comprise magnesium stearate. In other embodiments, the pharmaceutically acceptable carrier or excipient can be a component that reduces clumping of ingredients and/or reduce friction between, for example, the surface of a pharmaceutical formulation, i.e., formulated as an oral preparation, and the die wall during manufacture (e.g., a lubricant). Both water-soluble or water-insoluble lubricants may be used according to certain embodiments, such as magnesium stearate, stearic acid, vegetable oil, mineral oil, polyethylene glycol, and/or sodium lauryl sulfate. The pharmaceutically acceptable carrier or excipient can be a component that acts as a coating agent. Coating agents include, but are not limited to, gelatin and/or cellulose-based coating agents (e.g., hydroxypropyl methylcellulose).

Other suitable binders, flavors, sweeteners, colors, disintegrants, glidants, anti-adherents, lubricants, and coating agents are well known and readily identifiable in the art.

The pharmaceutical formulation can further comprise a therapeutic agent (e.g., a chemotherapeutic or anti-inflammatory agent). The pharmaceutical formulation can also comprise an agent that triggers an immune response separate from the influenza virus. Such additional components other than the inventive influenza virus can be present in any suitable amount(s).

The additional components can be mixed with the other components to form the pharmaceutical formulation prior to presentation to the immune system. The additional components can also be presented to the immune system separately from the pharmaceutical formulation. For example, the additional components and the pharmaceutical formulation can be presented to the immune system (e.g., administered to an organism) separately. When the additional components and the pharmaceutical formulation are administered separately, the additional components and the pharmaceutical formulation can be administered to the same site of the organism being immunized.

In one embodiment of the pharmaceutical formulation, the pharmaceutical formulation is a virus vaccine. The virus vaccine may be a live, attenuated virus vaccine or an inactivated virus vaccine (e.g., a whole virus vaccine, split virus vaccine, or subunit vaccine). The virus vaccine may be formulated as a monovalent vaccine, a bivalent vaccine, a trivalent vaccine, or a quadrivalent vaccine. For example, the vaccine may comprise multiple embodiments of the inventive influenza virus. In some embodiments, the vaccine may further comprise at least one influenza virus different from the influenza virus of the invention.

The virus vaccine can be formulated into a composition for any suitable means of administration. For example, the virus vaccine can be formulated as an oral preparation (e.g., capsule, tablet, or oral film), a spray (e.g., nasal spray), or any composition suitable for intranasal administration, or parenteral administration, e.g., intravenous, intramuscular, intradermal, or subcutaneous administration, such as an aqueous or non-aqueous emulsion, solution, or suspension.

Method of Eliciting an Immune Response

The invention provides a method of eliciting an immune response in a mammal comprising administering the inventive influenza virus to the mammal. In one embodiment, the influenza virus comprises a PB1 gene segment, a PB2 gene segment, a PA gene segment, an NP gene segment, and an NS gene segment, encoding proteins, i.e., a PB1 protein, a PB2 protein, a PA protein, an NP protein, and an NS1 protein, respectively, comprising selected amino acids, i.e., the influenza virus of the invention as described herein.

The mammal may be, for example, a human or primate, but is not limited thereto.

In one embodiment of the invention, the inventive influenza virus is administered in a pharmaceutical formulation (e.g., a vaccine or other immunogenic composition), as described herein. The pharmaceutical formulation can be administered intranasally. In another embodiment, the pharmaceutical formulation is administered intramuscularly. The pharmaceutical formulation also can be administered subcutaneously or orally.

The dosing regimen of the pharmaceutical formulation, e.g., the virus vaccine, may depend on the age, weight, sex, and medical history of the mammal. For example, in one embodiment, a single dose of an attenuated virus vaccine to a human can contain about $10^3$, $10^4$, $10^5$, $10^6$, $10^7$, $10^8$, $10^9$, $10^{10}$, $10^{11}$, or $10^{12}$, or any range between two of the foregoing values, particle forming units (PFU), focus forming units (FFU), or TCID$_{50}$ of the inventive influenza virus. In some embodiments, the regimen for preventing or treating an influenza virus comprises administering the pharmaceutical formulation as a single treatment. The pharmaceutical formulation also can be administered more than once, e.g., the dosing regimen can comprise a booster dosage. For example, the booster dose of the pharmaceutical formulation can be administered over a period ranging from 7 days or more, e.g., 8 days or more, 9 days or more, 10 days or more, 11 days or more, 12 days or more, 13 days or more, 14 days or more, 3 weeks or more, 4 weeks or more, 1 month or more, 2 months or more, 3 months or more, 4 months or more, 5 months or more, 6 months or more, 7 months or more, 8 months or more, 9 months or more, 10 months or more, 11 months or more, 1 year or more, 2 years or more, 3 years or more, 4 years or more, or five years or more, after the initial dose.

EMBODIMENTS

The invention provides the following embodiments:

(1) An influenza virus comprising PA, NP, and NS gene segments, wherein (a) the PA gene segment comprises a thymine at nucleotide position 2272; (b) the NP gene segment encodes a NP protein having an amino acid sequence comprising selected amino acids, wherein the selected amino acids comprise a serine at position 40, an asparagine or glycine at position 161, a threonine at position 204, and optionally a valine at position 93; and (c) the NS gene segment comprises a guanine at nucleotide position 39, and the NS gene segment encodes an NS1 protein having an amino acid sequence comprising selected amino acids, wherein the selected amino acids comprise a glutamine at position 176.

(2) The influenza virus of embodiment 1, wherein the PA gene segment has a nucleotide sequence represented by SEQ ID NO: 10.

(3) The influenza virus of embodiment 1 or 2, wherein the NP gene segment has a nucleotide sequence represented by SEQ ID NO: 11.

(4) The influenza virus of any one of claims 1-3, wherein the PA gene segment encodes a PA protein having an amino acid sequence of SEQ ID NO: 15.

(5) The influenza virus of any one of embodiments 1-4, wherein the NP gene segment encodes an NP protein having an amino acid sequence of SEQ ID NO: 16.

(6) The influenza virus of any one of embodiments 1-5, wherein the NS gene segment has a nucleotide sequence represented by SEQ ID NO: 12.

(7) The influenza virus of any one of embodiments 1-6, wherein the NS gene segment encodes an NS1 protein having an amino acid sequence of SEQ ID NO: 17.

(8) The influenza virus of any one of embodiments 1-7, wherein the selected amino acids are conserved in at least one of the NP and NS proteins after at least ten serial passages in a Vero cell line.

(9) The influenza virus of any one of embodiments 1-8, wherein the selected amino acids are conserved in at least one of the NP and NS proteins after at least ten serial passages in a Vero cell line that stably expresses the BM2 ion channel protein of influenza B virus.

(10) The influenza virus of any one of embodiments 1-9 wherein the influenza virus is a recombinant influenza virus.

(11) The influenza virus of any one of embodiments 1-10, wherein the virus further comprises a PB gene segment.

(12) The influenza virus of any one of embodiments 1-11, wherein the virus further comprises a NA gene segment and an HA gene segment.

(13) The influenza virus of embodiment 12, wherein the HA gene segment encodes an HA protein having an amino acid sequence comprising at least one amino acid mutation in HA2.

(14) The influenza virus of embodiment 13, wherein the at least one amino acid mutation in HA2 is a glutamic acid at position 61.

(15) The influenza virus of embodiment 13, wherein the at least one amino acid mutation in HA2 is a glutamic acid at position 112.

(16) The influenza virus of any one of embodiments 1-15, wherein the PA, NP, and NS gene segments are derived from a single influenza strain.

(17) The influenza virus of embodiment 16, wherein the HA gene segment is derived from an influenza strain different from the single influenza strain from which the PA, NP, and NS gene segments are derived.

(18) The influenza virus of embodiment 16 or 17, wherein the NA gene segment is derived from an influenza strain different form the single influenza strain from which the PA, NP, and NS gene segments are derived.

(19) The influenza virus of any one of embodiments 1-18, further comprising a mutant M gene segment.

(20) The influenza virus of embodiment 19, wherein the influenza virus does not encode a functional BM2 protein.

(21) The influenza virus of any one of embodiments 1-20, wherein the virus is capable of replication in human cells.

(22) The influenza virus of any one of embodiments 1-21, wherein the virus has enhanced growth as compared to an influenza virus that is the same except without the selected amino acids in Vero cells under the same conditions.

(23) The pharmaceutical formulation comprising the influenza virus of any one of embodiments 1-22.

(24) The pharmaceutical formulation of embodiment 23, wherein the pharmaceutical formulation is a vaccine.

(25) The pharmaceutical formulation of embodiment 24, wherein the vaccine is formulated as a monovalent vaccine.

(26) The pharmaceutical formulation of embodiment 24, wherein the vaccine is formulated as a bivalent vaccine.

(27) The pharmaceutical formulation of embodiment 24, wherein the vaccine is formulated as a trivalent vaccine.

(28) The pharmaceutical formulation of embodiment 24, wherein the vaccine is formulated as a quadrivalent vaccine.

(29) A method of eliciting an immune response in a mammal, the method comprising administering the influenza virus of any one of embodiments 1-22 or the pharmaceutical formulation of any one of embodiments 23-28 to the mammal, thereby eliciting an immune response to the influenza virus in the mammal.

(30) The method of embodiment 29, wherein the mammal is a human.

(31) A method of generating the influenza virus of any one of embodiments 1-22, the method comprising serially passaging in influenza virus in a Vero cell line.

EXAMPLES

The following examples further illustrate the invention but, of course, should not be construed as in any way limiting its scope.

Example 1

This example demonstrates the successful isolation of lineage agnostic growth enhancing influenza B NP D161N mutation.

Two vaccine candidate influenza B BM2SR strains that contained deletion of the BM2 ion channel function essential for multi-cycle replication were constructed by plasmid-based virus rescue procedures (see e.g., Neumann et al., *PNAS*, 96: 9345-9350 (1999)) in permissive BM2Vero cells that constitutively over express cDNA encoding BM2 from influenza B/Lee/40. The 2 segments encoding major antigens hemagglutinin (HA) and neuraminidase (NA) were obtained from Victoria lineage (VL) strain B/Brisbane/60/2008 (Bris60) and Yamagata lineage (YL) strain B/Wisconsin/01/2010 (WI01), both strains that were recommended by WHO for use in vaccination against seasonal influenza B disease. The BM2-deficient segment 7 was obtained by engineering the influenza B/Florida/4/2006 M segment to: (1) remove the BM2 transmembrane H+-channel, (2) introduce multiple stop codons in all translational reading frames, and (3) maintain native RNA structure for genetic stability and proper expression of M1 polypeptide. Five of the 8 genomic segments (i.e., PA, PB1, PB2, NP, and NS) were derived by selection from a virus library of influenza B/Yamagata/1/73 for VL and for YL strains with enhanced growth for high yield during Vero cell culture in vitro (Ping et al. 2016, supra). After 3 passages (P3) in BM2Vero the complete nucleotide sequence of each BM2SR strain was verified by Sanger sequencing of reverse transcriptase-polymerase chain reaction (RT-PCR) amplified cDNA from all 8 segments. The sequence of all 8 virus segments was identical to that of the 8 RNA segment expression plasmids used to rescue the viruses from both the YL and VL.

The vaccine candidate Bris60 (VL) and WI01 (YL) BM2SR P3 strains were then subjected to 10 additional viral passages at low multiplicity of infection (MOI) for a total of 13 passages (P13). After each passage round the viral titer was determined by tissue culture infectious dose 50% assay $(TCID_{50})$ in modified MDCK cells permissive for BM2SR replication (BM2CK, Hatta et al., *J. Virol.*, 78(11): 5576-5583 (2004)). Each subsequent passage was performed by infecting at MOI=0.001 $TCID_{50}$ equivalent per BM2Vero cell to allow for multi-cycle replication. After the many cycles of virus replication in 10 passages the nucleotide sequence of the two P13 strains was again obtained. Comparison of the P13 VL and YL strain sequences to the P3 strain sequences was performed to identify potentially adaptive mutations. Only 1 mutation identical in VL and YL or agnostic to influenza B lineage was identified in viral genomes from three independent passage experiments. The unique agnostic mutation was g540a in influenza B genomic segment 5 encoding aspartate 161 to asparagine substitution in nucleoprotein (NP D161N).

The initial B/Yamagata/1/73 high yield (HY) segment sequences of the VL and YL P3 strains differ for 2 segments: the nucleoprotein (NP) segment 5, and the non-structural protein (NS) segment 8. At P3 the Bris60 (VL) encoded NP P40S/M204T, NS g38insg and the WI01 (YL) BM2SR contained NP-P40S, and NS a39g, NS1-K176Q (Ping et al. 2016, supra). Following the extended passage, the VL NP segment 5 was found to encode NP P40S/D161N/M204T and the YL segment 5 encoded NP P40S/D161N. The same D161N mutation was present in both strains. Isolation of the identical substitution was not random and therefore D161N promotes growth of influenza B in Vero cells in culture. This is in contrast to the lineage specific mutations described for high growth viruses in Vero cells (Ping et al. 2016, supra).

A third passaging experiment was performed using the same BM2SR single replication vaccine virus backbone except the HA and NA segments were obtained from B/CA/12/2015 (YL). After 6 passages another NP segment nucleotide mutation a541g was isolated, resulting in a similar aspartate 161 to glycine substitution D161G. This example demonstrates that site 161 relates to high yield growth in Vero culture.

Figure 1:
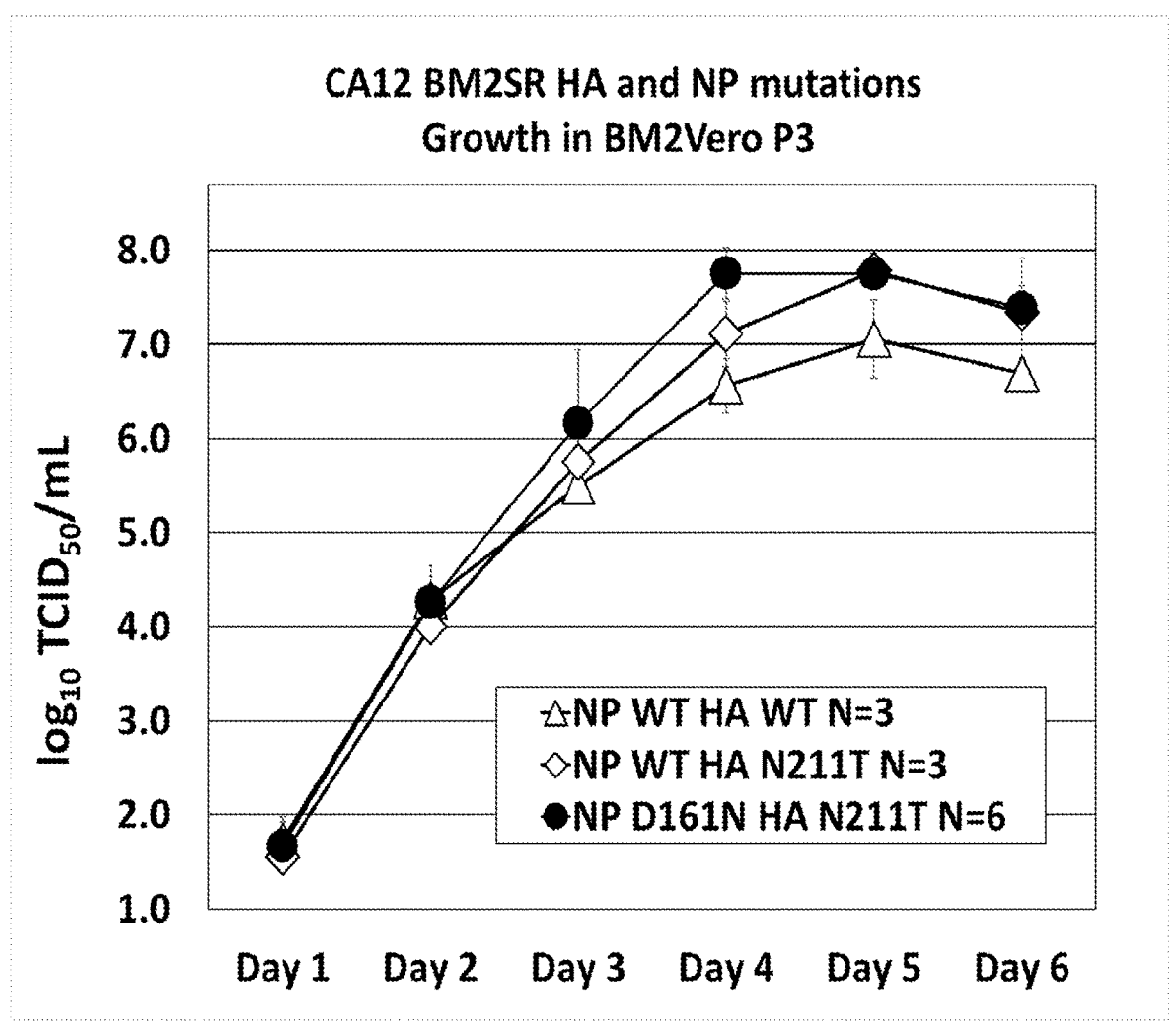
FIG. 1 is a graph depicting the growth of influenza BM2SR4 CA12 BM2SR HA and NP mutations in BM2Vero P3 versus time (days).

NP D161N mutation was added to the B/CA/12/2015 HA in combination with HA1 N211T mutation known to improve influenza B YL growth in culture. The HA1 N211T improved growth rate and titer. The NP D161N mutation was synergistic to HA1 N211T and decreased the time to maximum titer by 1 day as seen in FIG. 1.

Another influenza B NP mutation a336g encoding NP M93V was isolated multiple times but only when HA and NA were derived from VL. A mixture of g1164r encoding a mixture of WT and NP V369I was also isolated once.

Example 2

This example demonstrates successful growth of influenza B strains containing influenza B NP D161N adaptive mutation.

Various vaccine candidate influenza B BM2SR strains that contain deletion of the BM2 ion channel function essential for multi-cycle replication were constructed by plasmid-based virus rescue procedures (Neumann et al., supra) in permissive BM2Vero cells that constitutively over express cDNA encoding BM2 from influenza B/Lee/40. The 2 segments encoding hemagglutinin (HA) and neuraminidase (NA) antigens were obtained from Victoria lineage (VL) strain B/CO/06/2017 (CO06) strain as recommended by World Health Organization (WHO) for use in vaccination against seasonal influenza B disease. The BM2-deficient segment 7 was obtained by engineering the influenza B/Florida/4/2006 M segment to: (1) remove the BM2 transmembrane H+-channel, (2) introduce multiple stop codons in all translational reading frames, and (3) maintain native RNA structure for genetic stability and proper expression of M1 polypeptide. Four of the 8 genomic segments (PA, PB1, PB2, and NS) were derived by selection from a virus library of influenza B/Yamagata/1/73 for a VL strain with enhanced growth for high yield during Vero cell culture in vitro (Ping et al. 2016, supra).

The six strains differed only in the segment 5 nucleoprotein (NP) and contain permutations of 3 high yield mutations that were isolated from influenza B NP sequences obtained after passage in BM2Vero cells. Three strains were made that carry a single amino-acid substitution in NP: P40S, D161N or M204T. A control wild-type NP strain with no NP substitutions was made. Finally, a strain carrying two changes D161N/M204T and a strain with all three mutations were constructed. After 2 passages (P2) in BM2Vero the nucleotide sequence of the NP and BM2SR segments of each strain were verified by Sanger sequencing of RT-PCR amplified cDNA from all 8 segments.

Figure 2:
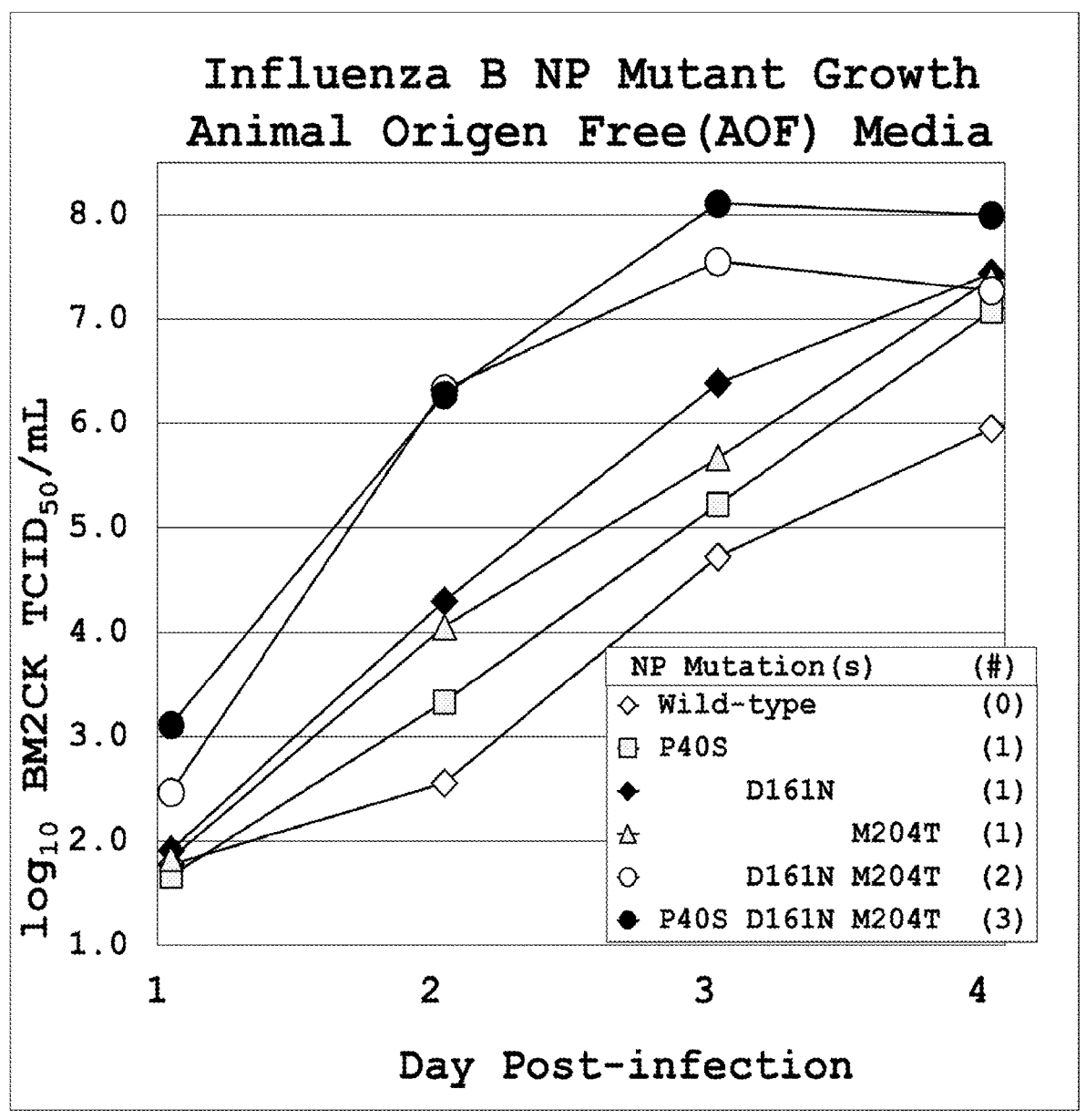
FIG. 2 is a graph depicting the growth of influenza B NP Mutants in Animal Origin Free (AOF) media versus time (days post-infection).

To compare growth characteristics, a third passage in BM2Vero was performed in triplicate for each virus. Each day for 4 days following inoculation at MOI=0.001 the cultures were sampled, and aliquots were stored frozen at −80° C. for later analysis by BM2CK $TCID_{50}$ assay. The mean of the triplicate determinations was calculated for each day as and is plotted in FIG. 2. Each of the single mutations alone conferred a growth benefit, but the D161N mutation had the greatest effect by itself. When the D161N was combined with M204T the double mutant strain achieved faster growth kinetics as compared to wild-type and to the single mutants. The triple mutant had fast kinetics and achieved highest maximum titer in 4 days as compared to the double mutant. Thus, D161N is a growth enhancing NP mutation that acts in synergy with other known NP substitutions to allow influenza B strains with more rapid growth that reach an even higher maximum titer.

Example 3

This example demonstrates the stability of influenza B NS segment during passage in culture.

NS1 function is known to be dispensable for influenza B virus culture in vitro in Vero cell culture. During passaging experiments, the NS segment accumulated various mutations. However, these mutations did not completely resolve, they were observed as mixtures with the starting sequence.

Many mutants were expansions of poly nucleotide tracts. Within the sequence read of B/Brisbane/60/2008 BM2SR4 P13 NS segment carrying g38insg there is a mixture of polyA7 expansion to polyA8 in the UTR (mRNA sense) just 5' of AUG (SEQ ID NO: 1), AAAAAAAUG (SEQ ID NO: 2) to AAAAAAAAUG (SEQ ID NO: 3). A B/CO/06/2017 strain that had NS g38insg was grown to P6 also had polyA7 expansion to A8 that was combined with reversion of the published g38insg HY promoter mutation. These sequencing data showed a complex mixture of sequences in the 5' UTR suggesting that NS g38insg was unstable in these experiments.

Figure 3:
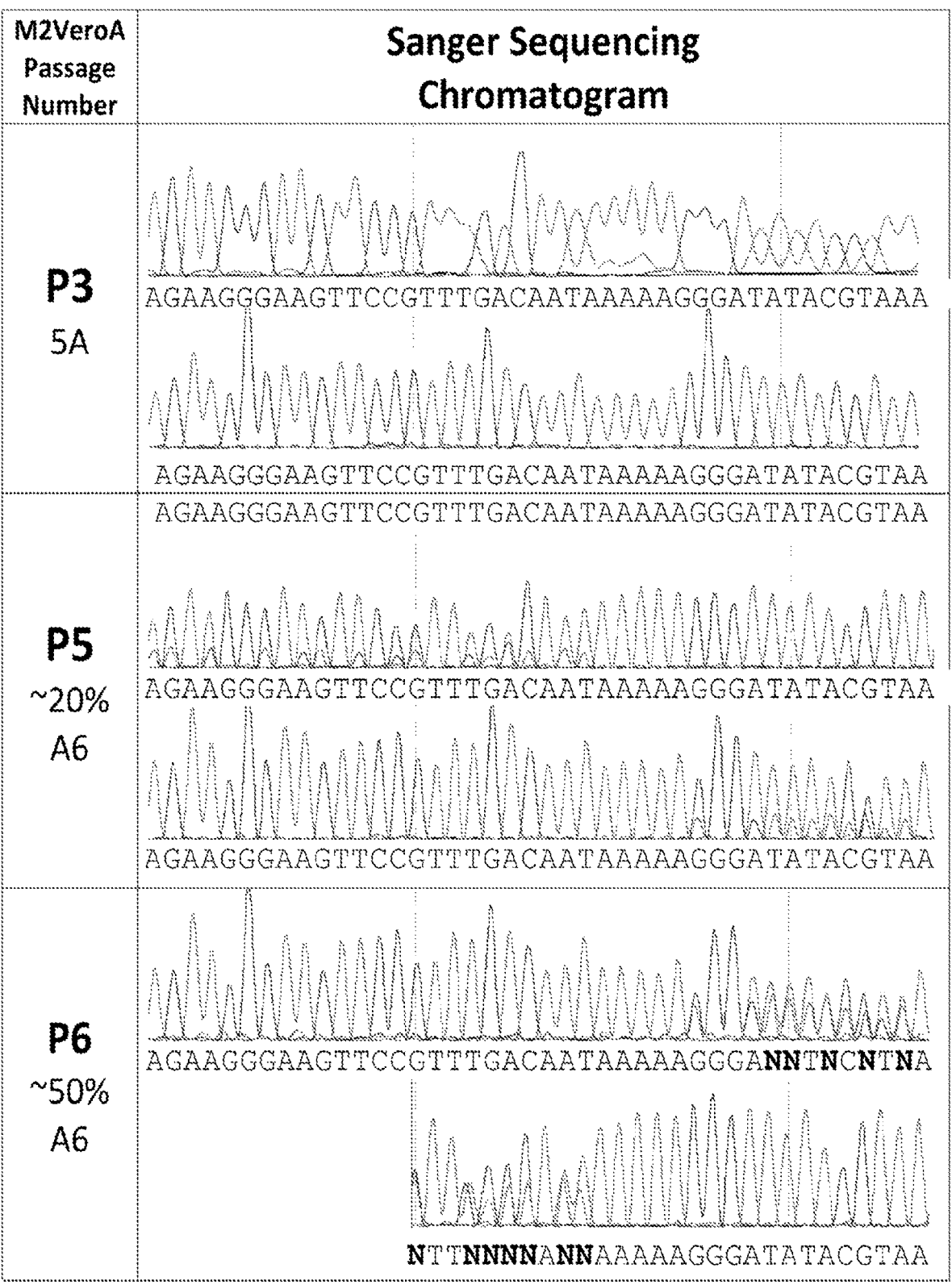
FIG. 3 is a set of Sanger sequence chromatogram data indicating that the frequency of mutation NS 569_570insA in an influenza B backbone increased from about 20% to about 50% mutant over subsequent passage.

A B/CA/12/2015 BM2SR strain with NS segment carrying g38insg was passaged 6 times and a mixture of the starting WT NS1 sequence with expansion of a polyA6 tract to polyA7 at position 569 was observed. The 569_570insA mutation causes a 176 amino acid NS1 truncation protein with 4 residue C-terminal extension. This mutation is within the same polyA6 tract site as the previously identified NS HY mutation, a570c, encoding K176Q. After passages P3, P5, and P6 genomic RNA was extracted from viral culture supernatant, and then RT-PCR was performed to amplify cDNA from all 8 genomic segments. Sequence chromatogram data given in FIG. 3 indicates that over time in passage a polyA stretch at base pairs 570-574 of NS segment 8 was increasing in length from 5 to 6 nucleotides. The frequency of the mutation, NS 569_570insA, increased from about 20% to about 50% mutant over subsequent passage indicating that the mutation is beneficial for growth in Vero cells.

The result of NS 569_570insA mutation (SEQ ID NO: 4) is translational frame shift in the NS1 open reading frame (ORF) after amino acid K176. The frameshift causes fusion of 4 new amino acids, KGYT (SEQ ID NO: 5), and then a TAA stop codon (SEQ ID NO: 6). Thus, a 176 amino acid NS1 truncation protein with 4 residue C-terminal extension is expressed as a 180 amino acid peptide (SEQ ID NO: 7, with X being any amino acid including G, R, or V). In this example, X was G. Splicing and expression of the NEP ORF is not affected by this mutation.

Truncation of the C terminal 105 amino acids of the 281-residue influenza B is likely to abrogate some or all NS1 functionality. NS1 performs several functions including repurposing of host mRNA metabolism such as polyadenylation and splicing, as well as impeding interferon dependent host cell innate immune responses like induction of RIG-I. Vero cells in culture are deficient in interferon response, which allows propagation of even complete NS1 deletion influenza strains in that cell line. Loss of NS1 C-terminus is favorable for the BM2SR backbone growth in Vero and this mutation could enhance production of vaccine material. The K176Q mutation may promote genetic stability at this site by insertion of G within the polyA6 run.

Passaging B/WI/01/2010 BM2SR4 containing the K176Q to P13 a mixture of NP sequences was obtained. The segment 8 sequence was same as starting plasmid including K176Q in about 70% of sequence. The rest of the sequence had deletion of 25 bp, 416del25 from NS1 ORF at ~30% of sequence. This deletion resulted in truncation of 158 residues after P123+12 new amino acids (AA) for 135 AA NS1 truncation mutant. These data indicate that the NS segment a39g K176Q is more stable overall. The combination of NS a39g K176Q segment and NP D161N HY mutation was tested in BM2Vero cells for improved stability. A B/CA/12/2015 strain that contains NS a39g K176Q and the NP P40S D161N M204T segment was passaged 10 times in BM2Vero cells. No NS or NP mutations were observed suggesting improved stability when the 2 HY segments were combined.

Example 4

This example demonstrates isolation of adaptive influenza B HA mutations during passage in culture.

Multiple BM2SR strains from both VL and YL were passaged within BM2Vero cells and the nucleotide sequence of the HA segments were determined. Silent mutations that did not change the coding sequence were not characterized. Eighteen mutations that did change the amino acid at fourteen sites were identified in the HA segment (Table 1). The mutations fell into two broad groups. Mutations in HA1 were often directly on a well-known N-linked glycosylation site at N209 (WA02 VL)/N210 (CO/06 VL)/N211 (YL) or to nearby residues important for glycosylase recognition. The majority of mutations isolated were located to the HA2 coiled coil region. Two HA2 mutations stood out. The HA a1294g mutation was observed in multiple experiments where B/CO/06/2017 BM2SR strains were passaged, independent of NP or NS segment identity. The glycosylation site adaptations likely have effect upon the affinity of HA binding to target Vero cells. Changes in the HA2 coiled coil are thought to influence the pH-dependent conformational change required for HA fusion with the membrane of a target cell.

TABLE 1

HA Segment Mutations Isolated by BM2SR Passage in BM2Vero
Cells and Introduced HA2 Mutations at Same Sites

| Nucleotide Mutation Isolated | Source Strain for Mutation Isolated | HA0 Amino Acid*, (HA2) Mutation | HA Region |
|---|---|---|---|
| a141c | CO/06/2017 (VL) | Q36H | HA1 |
| a659g | WA/02/2019 (VL) | N209S* | HA1 Glycosylation Site |
| c662t | CA/12/2015 (YL) | M211T* | HA1 Glycosylation Site |
| a670r, c671y, c671m | CA/12/2015 (YL) | T213X* | HA1 Glycosylation Site |
| g846a | Bris/60/2008 (VL) | G271E* | HA1 |
| g1213a | CO/06/2017 (VL) | V394M* (V34M) | HA2 coiled coil |
| a1264g | CO/06/2017 (VL) | N411D* (K51D) | HA2 coiled coil |
| a1300g | Bris/60/2008 (VL) | K423E* (K61E) | HA2 coiled coil |
| a1294g, a1294r | CO/06/2017 (VL) | K421E* (K61E) | HA2 coiled coil |
| @a1291g | WA/02/2017 (VL) | K420E* (K61E) | HA2 coiled coil |
| g1307a | CO/06/2017 (VL) | R425K* (R65K) | HA2 coiled coil |
| a1344g | CA/12/2015 (YL) | I438M* (I77M) | HA2 coiled coil |
| a1448g | CO/06/2017 (VL) | D472G* (D112G) | HA2 coiled coil |
| @c1452a | CA/12/2015 (YL) | D473E* (D112E) | HA2 coiled coil |
| @g1450a | CA/12/2015 (YL) | D473N* (D112N) | HA2 coiled coil |
| g1592a, g1592r | CO/06/2017 (VL) | G520E* (G160E) | HA2 |
| t1613y | CO/06/2017 (VL) | F527S* (F166S) | HA2 |
| t1653actmix | CA/12/2015 (YL) | D540E* (D179E) | HA2 |

*= HA0 Amino acid number differs between the strains due to a 1, 2, or 3 amino acid deletion in the HA1 of newer strains as compared to Bris/60/2008 HA0 (HA2 number unchanged).
@= Introduced Mutation Different influenza B lineages and strains may have a different number of amino acids due to a sequential 1, 2 or 3 amino acid deletion in influenza B VL HA1 gene segments (depending on the year) and a 1 AA deletion in influenza B YL in the HA1 gene segment as compared to influenza B/Bris/60/2008 HA1. The amino acids with an asterisk in Table 1 indicate that the mutations may occur at a different position in different strains. Table 2 shows examples of the different positions the amino acid mutations that occur in different strains. Some isolated mutations were introduced to HA of other strains and were tested for growth enhancement.

TABLE 2

HA0 Positions of Certain Amino Acid Mutations
Identified in Table 1 per Strain

| WA/02/2019 | CO/06/2017 | CA/12/2015 | Bris/60/2008 |
|---|---|---|---|
| N209S[a, b, c] | N210T[a, b] | N211T[a, b] | N212D[b] |
| K420E[c] | K421E[a] | K422E[c] | K423E[a] |
| D471G[d] | D472G[a] | D473G[c] | D474G[d] |
| D471E[d] | D472E[d] | D473E[c] | D474E[d] |
| D471N[d] | D472N[d] | D473N[c] | D474N[d] |

[a]Isolated at FluGen.
[b]From sequence database, egg-passaged strain.
[c]Introduced.
[d]Not determined.

Example 5

This example demonstrates the rescue of influenza B/WA/02/2019 BM2SR (VL) strains with influenza B HA adaptive mutations.

Three versions of cDNA encoding the influenza HA segment 5 of WHO-recommended vaccine strain B/WA/02/2019 (VL) were synthesized and inserted into RNA expression plasmid vector for influenza B plasmid-based virus rescue. The first HA version encoded the wild-type (WT) HA protein sequence obtained directly from influenza patient primary isolate. The WT HA has an intact N209 glycosylation site in the HA1. Passaging of the influenza B/WA/02/2019 (VL) strain in cell or egg culture resulted in loss of glycosylation at this site, primarily by N209S substitution (GISAID). A second plasmid encoded a mutant HA2 K61E (K421E) obtained from passage of B/CO/06/2017 strains. A double mutant with addition of glycosylation minus N209S HA1 mutant to the HA2 K61E change was also built.

Figure 4:
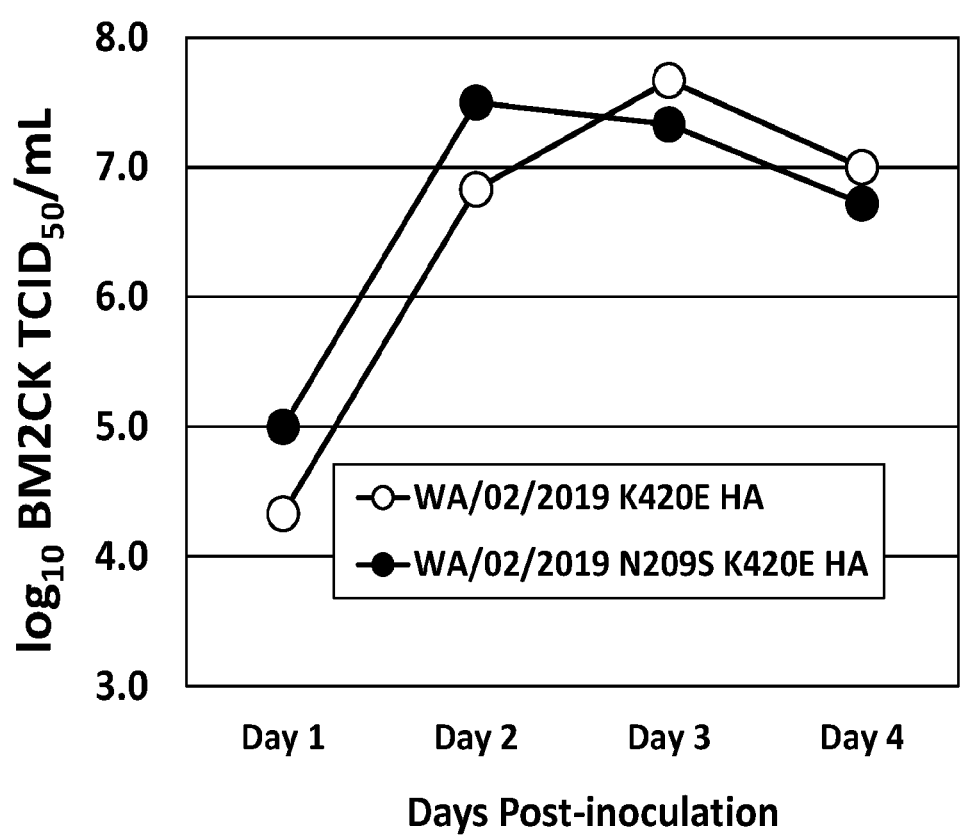
FIG. 4 is a graph depicting the growth of WA/02/2019 N209S and K420E HA in BM2Vero P3 in AOF versus time (days post-inoculation).

Standard plasmid-based virus rescue procedure using the three types of HA plasmid was employed to construct B/WA/02/2019 BM2SR (VL) viruses by transfection of BM2Vero cells. Both the single and double mutant HA plasmids did support rescue of BM2SR virus, but the fully WT HA sequence did not generate viable virus (assay LOD=$\log_{10}$ 0.67 TCID$_{50}$/mL). Both the successful vaccine candidates were passaged to P2 in BM2Vero and HA sequence was confirmed. The viruses were passaged to P3 at MOI=0.01 and daily aliquots were frozen for TCID$_{50}$ determination of virus titer as shown in FIG. 4 and Table 3. The single mutant strain with K420E (K61E HA2) mutation alone grew well allowing the glycosylation plus strain to reach maximum $\log_{10}$ TCID$_{50}$/mL of 7.67 in 3 days. Double mutant, glyco-HA strain grew faster but to a similar peak titer of $\log_{10}$ 7.50 in 2 days.

TABLE 3

Growth of B/WA/02/2019 BM2SR Strains with HA1 and
HA2 Mutations (assay LOD = $\log_{10}$ 0.67 TCID$_{50}$/mL).

| Virus Strain | Virus Titer ($\log_{10}$ TCID$_{50}$/mL) | | | |
|---|---|---|---|---|
| | Day 1 | Day 2 | Day 3 | Day 4 |
| B/WA/02/2019 K420E HA | 4.33 | 6.83 | 7.67 | 7.00 |
| B/WA/02/2019 N209S K420E HA | 5.00 | 7.50 | 7.33 | 6.72 |

Example 6

This example demonstrates growth of influenza B/CA/12/2015 BM2SR (YL) strains with influenza B HA adaptive mutations.

Figure 5:
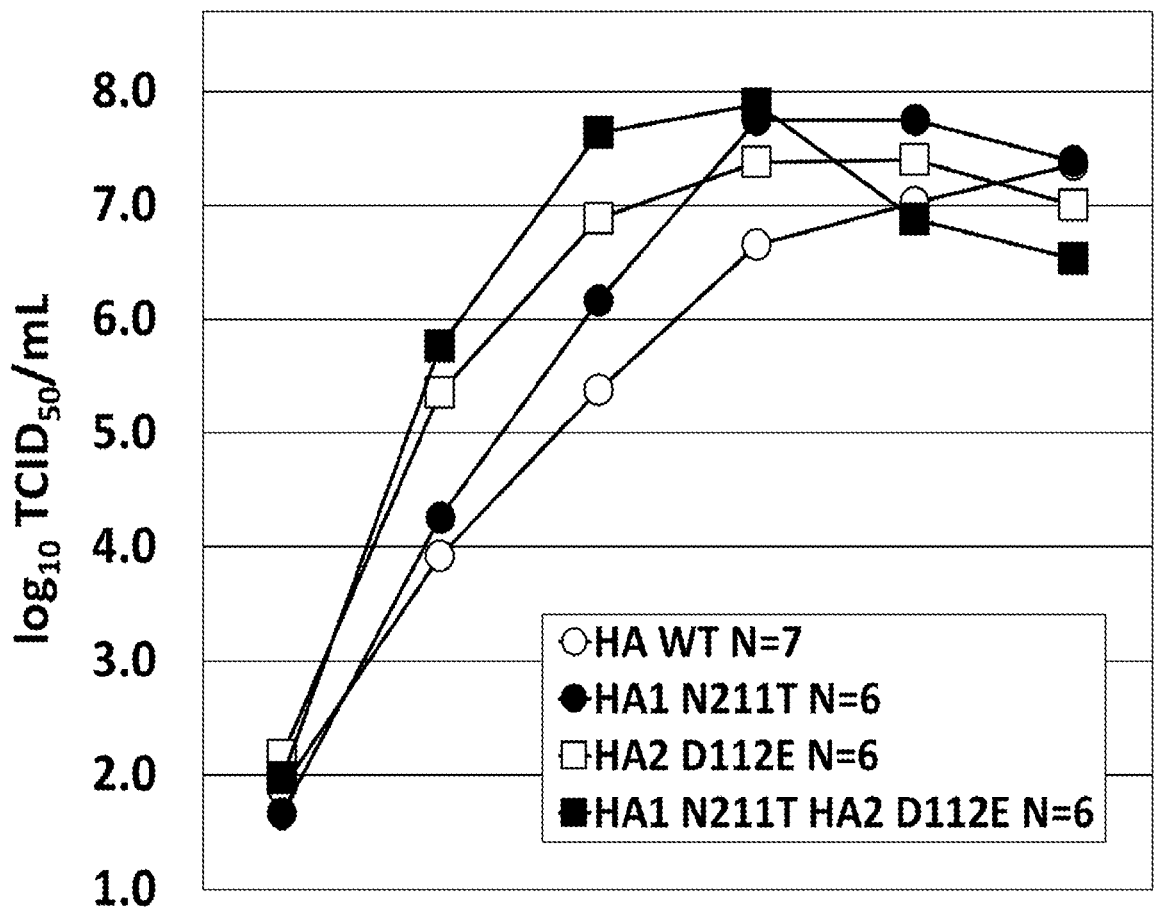
FIG. 5 is a graph depicting the growth of influenza BM2SR4 CA12 HA2 mutations in BM2Vero P3 versus time (days).

Eight versions of cDNA encoding the influenza HA segment 5 of WHO-recommended vaccine strain B/CA/12/2015 (YL) were synthesized and inserted into RNA expression plasmid vector for influenza B reverse genetic rescue to create four HA mutant strains. These four HA mutant strains derived from Vero passage comprised five mutations at four HA2 residues: 1.) N51D and D61E; 2.) D90N; 3.) D112E; and 4.) D112K all combined with the HA1 glycosylation site mutation N211T. The HA2 N51D, K61E mutation obtained by passage of B/CO/06/2017 helped growth but only if combined with N211T. The HA2 D90N and D112K mutations obtained by passage of influenza A H3N2 in Vero harmed growth or had no effect when in combination with N211T. The D112E (D473E) was beneficial conferring faster growth to maximum titer, regardless of the glycosylation site N211 as shown in FIG. 5.

Example 7

This example further demonstrates growth of influenza B/CA/12/2015 BM2SR strains with influenza B HA adaptive mutations.

Figure 6:
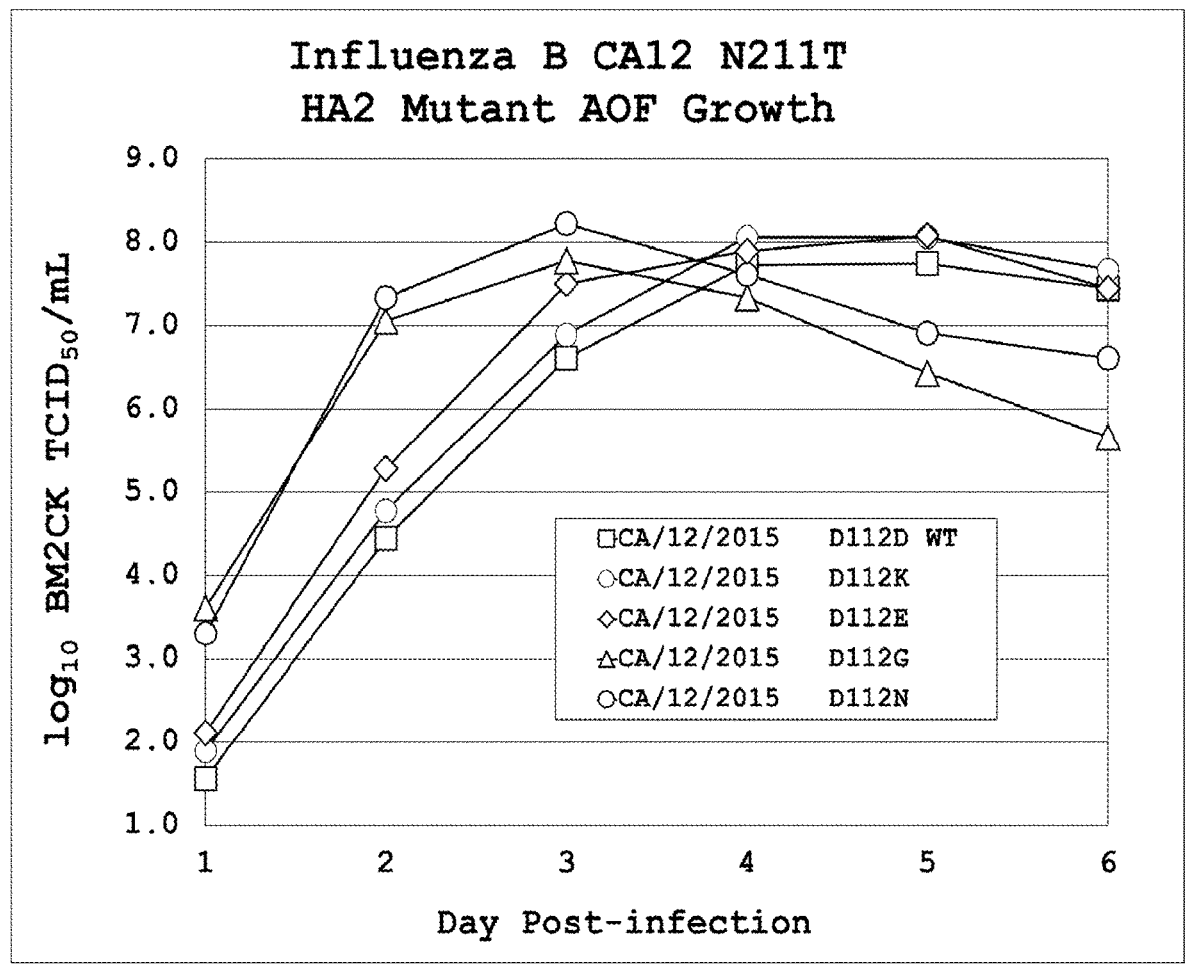
FIG. 6 is a graph depicting the growth of influenza B CA12 N211T HA2 mutants in AOF versus time (days post-infection).

The HA2 D112 site in influenza B YL had significant effects on growth in culture. Independent of the glycosylation site N211 the HA2 D112 mutation D473E (D112E) was beneficial to influenza BM2SR conferring faster growth to maximum titer than other B/CA/12/2015 (YL) HA2 112 mutants, so additional substitutions HA2 D112G and HA2 D112N were made. These HA2 mutations are influenza A HA2 mutations at position E112 that confer amantadine resistance and significantly raise the pH where the HA spike protein conformational change can occur (Byrd-Leotis et al., *J. Virol.*, 89(8): 4504-4516 (2015)). The HA2 D112G has been shown to function in the context of every influenza A HA in which it has been tested. For influenza B, the HA2 D112G and HA2 D112N were beneficial and synergistic conferring faster growth to maximum titer, in combination with N211 as shown in FIG. 6.

Example 8

This example further demonstrates successful isolation of other adaptive influenza B HA mutations during passage in culture.

In accordance with the previous examples, additional adaptive influenza B HA mutations were isolated during passage in culture. These mutations are summarized below in Table 4.

TABLE 4

| Segment | Nucleotide | Amino Acid |
| --- | --- | --- |
| PB2 | 446de19 mixture | 3AA deletion |
| | a1059c | I346V |
| PB1 | a1761t | E508D |
| PA | a838r | Y270C |
| NA | a23insa | 5' UTR |
| | t58y, t58c | NA L2P, NB A4A |
| | c64t | NA S4L, NB F6F |
| | c89t | NA F12F, NB P15S |
| | t150c | NA Y33H, NB I35T |
| | t166c | NA L36P |
| | t1429c | V459A |
| BM2SR4 | c406c, about 70% C | M1 L128I |
| | Expansion of g4 to g5 g817insg | Past stops |

Example 9

This example demonstrates that BM2SR viruses elicit antibody responses against influenza B viruses formulated in multivalent vaccines.

Influenza BM2SR-Vic or BM2SR-Yam viruses (viruses comprising PB1, PB2, PA, NP, NS, and M gene segments with nucleotide sequences represented by SEQ ID NOs: 8, 9, 10, 11, 12, and 18, respectively) elicit antibody responses when formulated as a monovalent, bivalent, trivalent, or quadrivalent vaccine.

Seven-week-old BALB/c female mice (N=8) were immunized intranasally with monovalent BM2SR-Vic, monovalent BM2SR-Yam, bivalent BM2SR, trivalent BM2SR-Vic+BM2SR-Yam+M2SR-H1N1, trivalent BM2SR-Vic+BM2SR-Yam+M2SR-H3N2, or quadrivalent BM2SR-Vic and -Yam and M2SR-H1N1 and -H3N2 vaccines. A control group of mice were mock immunized with SPG buffer (sucrose phosphate glutamate buffer). 28 days after vaccination, the mice were immunized intranasally with a boost immunization consisting of the same vaccine administered for the prime immunization. Serum samples were taken on days 7, 14, and 21 following prime immunization and on days 35, 42, and 49 following the boost immunization (day 28). Anti-Influenza B-Vic HA and anti-Influenza B-Yam HA serum IgG antibody titers from the serum samples were determined by ELISA.

Figure 7A:
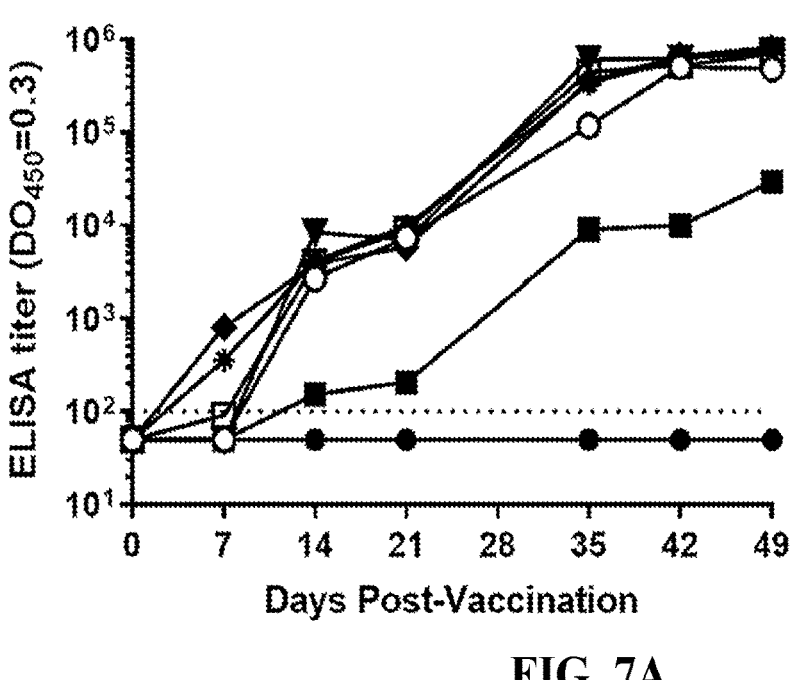
FIG. 7A is a graph depicting the anti-Influenza B-Vic HA titer in sera from mice immunized with monovalent BM2SR-Vic, monovalent BM2SR-Yam, bivalent BM2SR, trivalent BM2SR+M2SR-H1N1, trivalent BM2SR+M2SR-H3N2, quadrivalent M2SR, or sucrose phosphate glutamate buffer ("SPG"; control) versus time (days post-immunization).
Figure 7B:
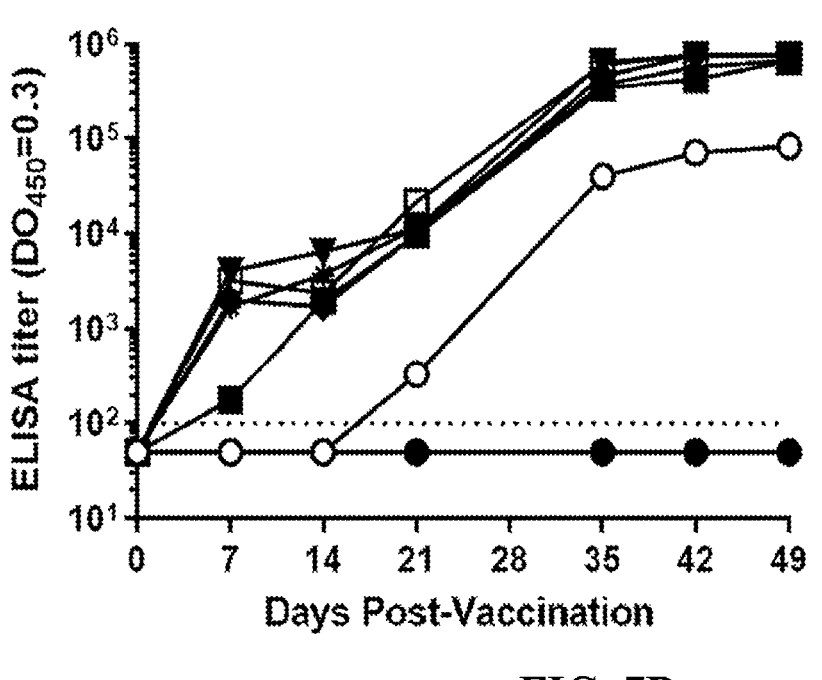
FIG. 7B is a graph depicting the anti-Influenza B-Yam HA titer in sera from mice immunized with monovalent BM2SR-Vic, monovalent BM2SR-Yam, bivalent BM2SR, trivalent BM2SR+M2SR-H1N1, trivalent BM2SR+M2SR-H3N2, quadrivalent M2SR, or SPG (control) versus time (days post-immunization).

The resulting anti-Influenza B-Vic HA data is shown in FIG. 7A. The resulting anti-Influenza B-Yam HA data is shown in FIG. 7B. The results demonstrated that all vaccines were able to elevate anti-influenza virus antibodies above SPG control and that these increases were comparable across vaccine formulations. These results demonstrate that there is no interference between the monovalent components when formulated into multivalent vaccines.

Example 10

This example demonstrates that the intranasally administered monovalent or quadrivalent M2SR vaccine protects mice from lethal influenza B virus that is not contained in the vaccine.

Figure 8:
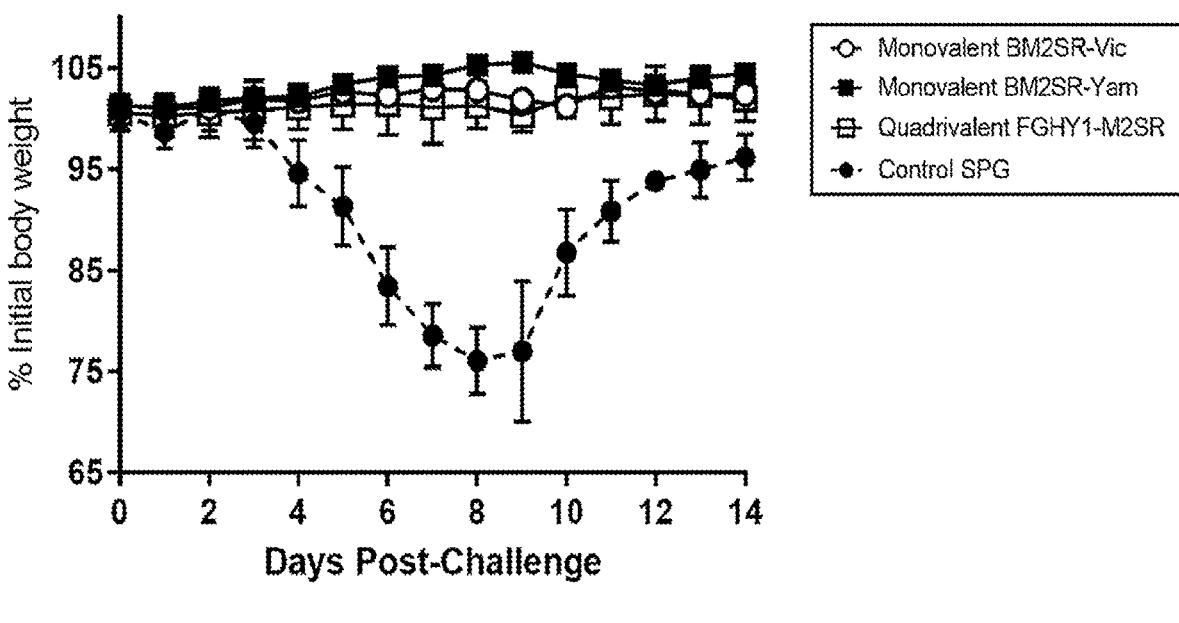
FIG. 8 is a graph depicting mouse percent body weight change after challenge with B/Malaysia/2506/2004 (Vic) virus of mice immunized with monovalent BM2SR-Vic, monovalent BM2SR-Yam, quadrivalent M2SR, or SPG (control) versus time (days post-challenge).

The BALB/c female mice described in Example 9 were challenged with a lethal dose of influenza B/Malaysia/2506/2004 (Vic) virus (>10 mouse 50% lethal dose ($MLD_{50}$)) 70 days after the first immunization (6 weeks after the boost immunization). All mice immunized with the monovalent BM2SR-Vic (influenza B/CO/06/2017) or BM2SR-Yam (influenza B/Phuket/3073/2013) and quadrivalent M2SR vaccines survived the challenge. The mice immunized with monovalent BM2SR-Vic, monovalent BM2SR-Yam and quadrivalent M2SR vaccines remained healthy with no body weight loss. The resulting body weight loss data is shown in FIG. 8. The control mice that were mock immunized with only SPG lost body weight and 4 out of 8 succumbed to infection within 10 days post-challenge. On day 3 post-challenge, lungs were obtained from 3 mice per group, and viral load was determined via plaque assay in MDCK cells. As shown in Table 5, virus titers in the lungs of mice that were immunized with monovalent BM2SR-Vic, monovalent BM2SR-Yam, and quadrivalent M2SR vaccine were below the limit of detection (less than 76 plaque forming units (PFU) per lung). Viral load was detected in mice immunized with only SPG control (average of 6.86 log PFU/g). These results indicate that the BM2SR monovalent and quadrivalent vaccines confer cross-protection and limit the replication of a challenge virus that does not match any vaccine component.

TABLE 5

Challenge Virus Titer in Lungs, 3 Days Post-Challenge

| Vaccine | Mouse | Lung Virus Titer (log PFU/g) | Average Lung Virus Titer ± SD (log PFU/g) |
|---|---|---|---|
| BM2SR-Vic | 1 | —* | — |
| | 2 | — | |
| | 3 | — | |
| BM2SR-Yam | 1 | — | — |
| | 2 | — | |
| | 3 | — | |
| Quadrivalent M2SR | 1 | — | — |
| | 2 | — | |
| | 3 | — | |
| Control SPG | 1 | 6.88 | 6.86 ± 0.09 |
| | 2 | 6.95 | |
| | 3 | 6.77 | |

*Below detection limit (76 PFU/g)

Example 11

This example demonstrates that the bivalent, trivalent or quadrivalent M2SR that contains the BM2SR components provides a favorable safety profile compared to a licensed intranasal influenza vaccine as well as superior protection to licensed intramuscular inactivated influenza vaccines against influenza viruses that are not contained in the vaccine. The antigenically distinct monovalent BM2SR-Vic and monovalent BM2SR-Yam vaccines provide comparable protection to antigenically matched licensed vaccines in protection of mice from lethal influenza B virus.

Seven-week-old BALB/c female mice (N=13) were immunized with one of the following vaccines: monovalent BM2SR-Vic, monovalent BM2SR-Yam, quadrivalent FGHY-M2SR, FLUMIST™ Quadrivalent (AstraZeneca, Wilmington, DE), FLUZONE™ Quadrivalent (Sanofi, Bridgewater, NJ) or FLUZONE™ High Dose (Sanofi). Strain components for each vaccine are shown in Table 6. BM2SR, M2SR, and FLUMIST™ were intranasally dosed while both FLUZONE™ vaccines were intramuscularly dosed. A control group of mice were intranasally mock immunized with SPG. The mice were observed for 14 days after immunization for any change in body weight.

TABLE 6

Strain Components for Each Vaccine

| Vaccine | Influenza A | | Influenza B | |
| | (H1N1pdm) | (H3N2) | Yamagata Lineage | Victoria Lineage |
|---|---|---|---|---|
| M2SR-H1N1 | A/MI/45/2015-like A/Montana/50/2016 | None | None | None |
| M2SR-H3N2 | None | A/Singapore/IN FIMH -16- 0019/2016 | None | None |
| BM2SR-Vic | None | None | None | B/Colorado/ 06/2017 |
| BM2SR-Yam | None | None | B/Phuket/3073/2013-like B/California/12/2015 | None |
| M2SR Bi | A/MI/45/2015-like A/Montana/50/2016 | A/Singapore/IN FIMH -16- 0019/2016 | None | None |
| BM2SR Bi | None | None | B/Phuket/3073/2013-like B/California/12/2015 | B/Colorado/ 06/2017 |
| M2SR Tri- Vic | A/MI/45/2015-like A/Montana/50/2016 | A/Singapore/IN FIMH -16- 0019/2016 | None | B/Colorado/ 06/2017 |
| M2SR Tri- Yam | A/MI/45/2015-like A/Montana/50/2016 | A/Singapore/IN FIMH -16- 0019/2016 | B/Phuket/3073/2013-like B/California/12/2015 | None |
| BM2SR Tri- H1N1 | A/MI/45/2015-like A/Montana/50/2016 | None | B/Phuket/3073/2013-like B/California/12/2015 | B/Colorado/ 06/2017 |
| BM2SR Tri- H3N2 | None | A/Singapore/IN FIMH -16- 0019/2016 | B/Phuket/3073/2013-like B/California/12/2015 | B/Colorado/ 06/2017 |
| Quadrivalent M2SR | A/MI/45/2015-like A/Montana/50/2016 | A/Singapore/IN FIMH -16- 0019/2016 | B/Phuket/3073/2013-like B/California/12/2015 | B/Colorado/ 06/2017 |
| FLUMIST ™ Quadrivalent | A/MI/45/2015-like A/Slovenia/2903/ 2015 | A/Singapore/IN FIMH -16- 0019/2016 | B/Phuket/3073/2013 | B/Colorado/ 06/2017 |
| FLUZONE ™ Quadrivalent | A/MI/45/2015 | A/Singapore/IN FIMH -16- 0019/2016 | B/Phuket/3073/2013 | B/Colorado/ 06/2017-like B/Maryland/ 15/2016 |
| FLUZONE ™ High Dose | A/MI/45/2015 | A/Singapore/IN FIMH -16- 0019/2016 | None | B/Colorado/ 06/2017-like B/Maryland/ 15/2016 |

Figure 9:
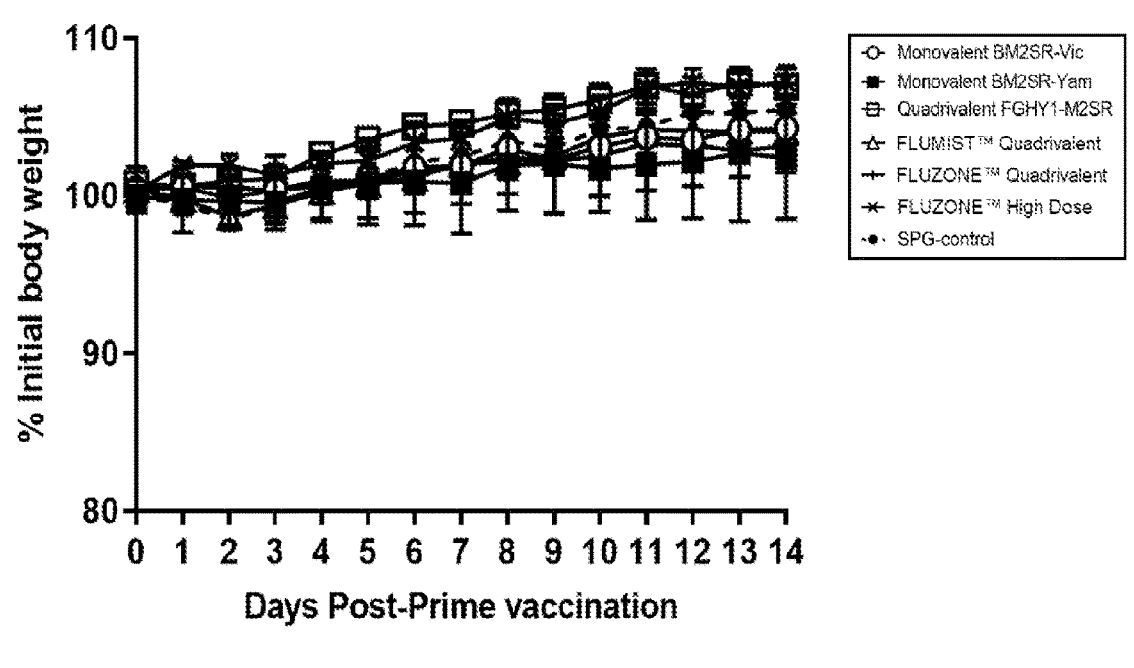
FIG. 9 is a graph depicting mouse percent body weight change after immunization with monovalent BM2SR-Vic, monovalent BM2SR-Yam, quadrivalent M2SR, FLU-MIST™ Quadrivalent, FLUZONE™ Quadrivalent, FLU-ZONE™ High Dose, or SPG (control) versus time (days post-vaccination).

The resulting weight-loss data is shown in FIG. 9. Mice that were immunized with monovalent BM2SR-Vic, monovalent BM2SR-Yam, quadrivalent M2SR, FLUZONE™ Quadrivalent, FLUZONE™ High Dose, or SPG control experienced no body weight loss over the 14-day period. These data indicate that BM2SR vaccines have an equivalent safety profile to licensed influenza vaccines.

Figure 10A:
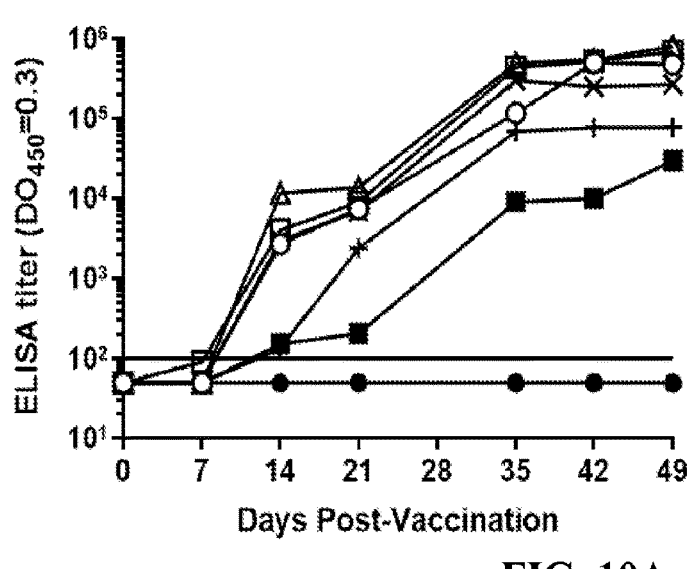
FIG. 10A is a graph depicting the anti-influenza B-Vic HA serum IgG ELISA titers in sera of mice immunized with monovalent BM2SR-Vic, monovalent BM2SR-Yam, quadrivalent M2SR, FLUMIST™ Quadrivalent, FLUZONE™ Quadrivalent, FLUZONE™ High Dose, or SPG (control) versus time (days post-vaccination).
Figure 10B:
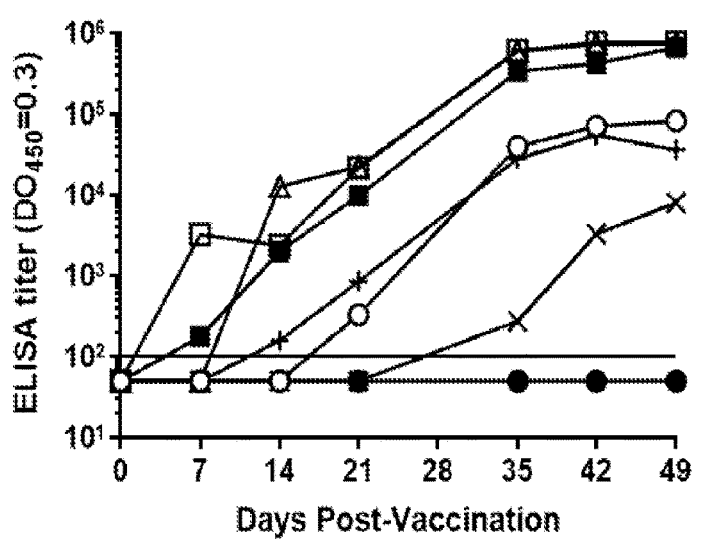
FIG. 10B is a graph depicting the anti-influenza B-Yam HA serum IgG ELISA titers in sera of mice immunized with monovalent BM2SR-Vic, BM2SR-Yam, quadrivalent M2SR, FLUMIST™ Quadrivalent, FLUZONE™ Quadrivalent, FLUZONE™ High Dose, or SPG (control) versus time (days post-vaccination).
Figure 10C:
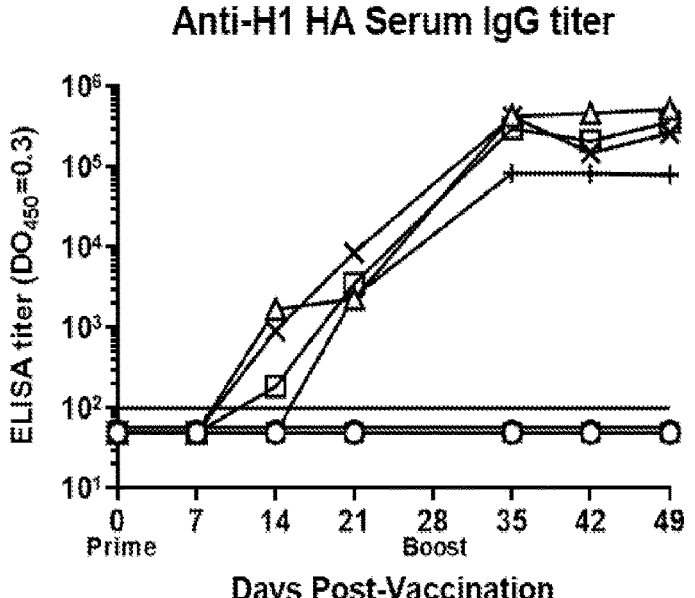
FIG. 10C is a graph depicting the anti-influenza A/H1 HA serum IgG ELISA titers in sera of mice immunized with monovalent BM2SR-Vic, monovalent BM2SR-Yam, quadrivalent M2SR, FLUMIST™ Quadrivalent, FLUZONE™ Quadrivalent, FLUZONE™ High Dose, or SPG (control) versus time (days post-vaccination).
Figure 10D:
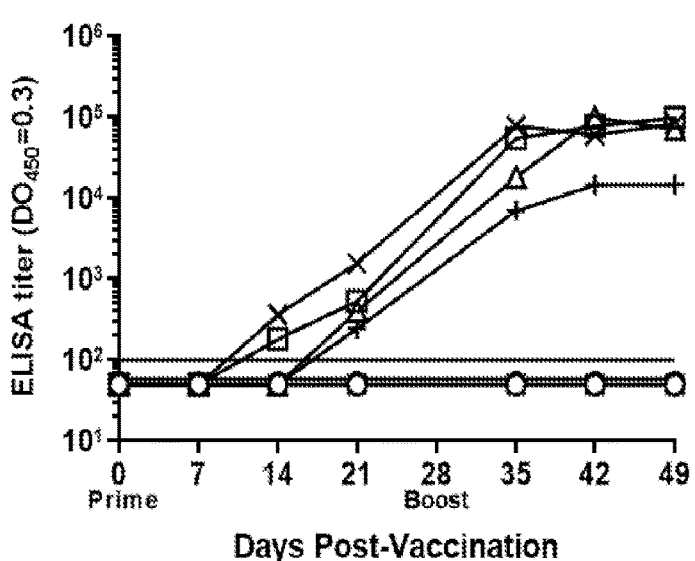
FIG. 10D is a graph depicting the anti-influenza A/H3 HA serum IgG ELISA titers in sera of mice immunized with monovalent BM2SR-Vic, monovalent BM2SR-Yam, quadrivalent M2SR, FLUMIST™ Quadrivalent, FLUZONE™ Quadrivalent, FLUZONE™ High Dose, or SPG (control) versus time (days post-vaccination).

The mice were immunized with a boost immunization on day 28 post-prime immunization. The boost immunization consisted of the same vaccine the mice were immunized with in the prime immunization. Serum samples were collected weekly after prime and boost immunizations, and pooled serum IgG titers against each of the vaccine components were determined by ELISA. Resulting anti-influenza B-Vic HA serum IgG ELISA titers data are shown in in FIG. 10A. Resulting anti-influenza B-Yam HA serum IgG ELISA titers data are shown in FIG. 10B. Resulting anti-influenza A/H1 HA serum IgG ELISA titers data are shown in FIG. 10C. Resulting anti-influenza A/H3 HA serum IgG ELISA titers data are shown in FIG. 10D. The results demonstrate that all vaccines were able to elevate serum IgG titers against influenza B-Vic HA and B-Yam HA above SPG control, and that these increases were comparable across vaccine formulations. FLUZONE™ Quadrivalent and FLUZONE™ High Dose elicited lower serum IgG titers against influenza B HA antigens compared to live vaccines.

Figure 11A:
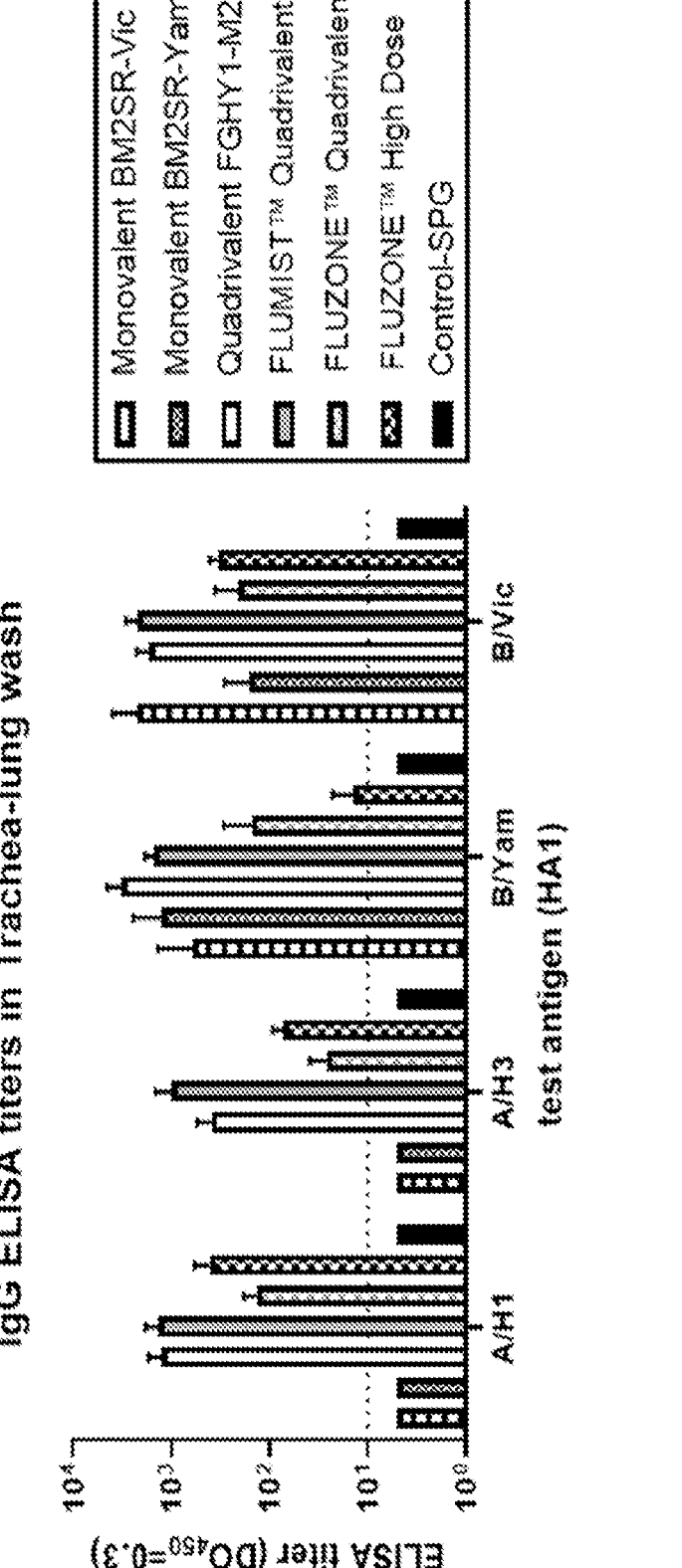
FIG. 11A is a graph depicting IgG ELISA titers in trachea-lung wash of mice immunized with monovalent BM2SR-Vic, monovalent BM2SR-Yam, quadrivalent M2SR, FLUMIST™ Quadrivalent, FLUZONE™ Quadrivalent, FLUZONE™ High Dose, or SPG (control) versus HA1 test antigen (A/H1, A/H3, B/Yam, or B/Vic).
Figure 11B:
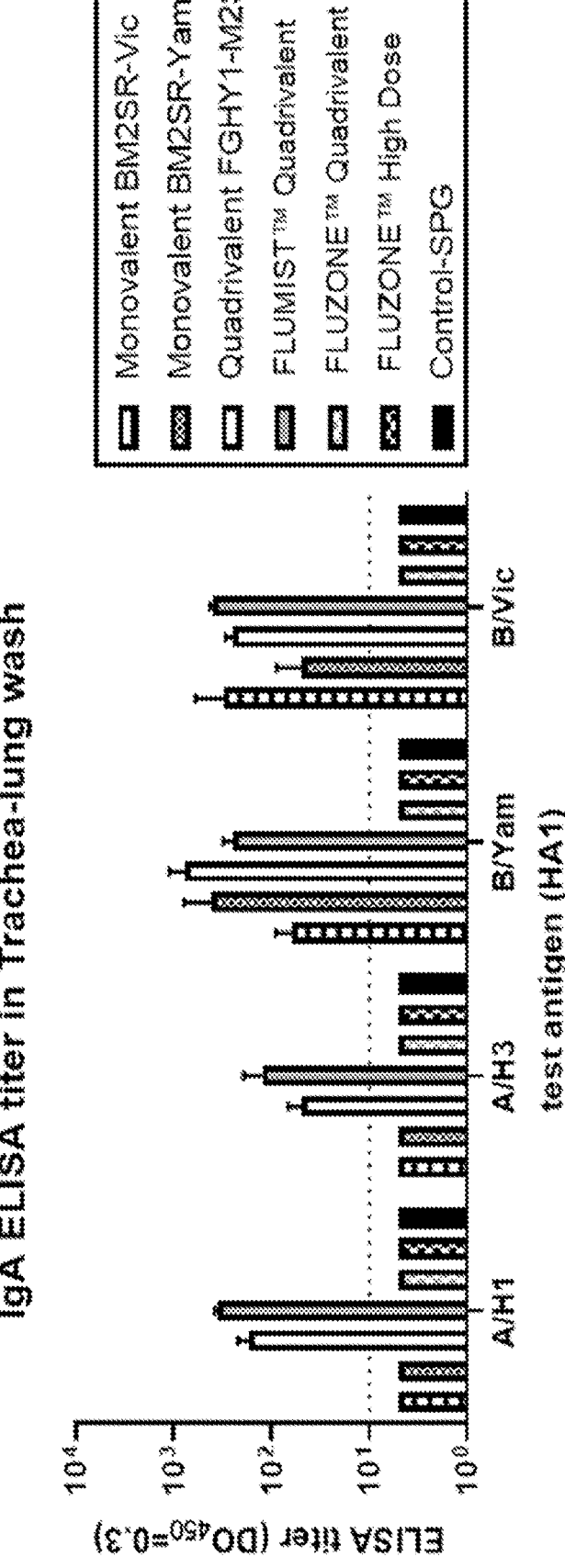
FIG. 11B is a graph depicting anti-influenza HA1 IgA ELISA titers in trachea-lung wash of mice immunized with monovalent BM2SR-Vic, monovalent BM2SR-Yam, quadrivalent M2SR, FLUMIST™ Quadrivalent, FLUZONE™ Quadrivalent, FLUZONE™ High Dose, or SPG (control) versus HA1 test antigen (A/H1, A/H3, B/Yam, or B/Vic).

Trachea-lung washes were obtained from 4 mice per group on day 49 post-prime immunization (21 days post-boost) and IgG and IgA titers were determined by ELISA to evaluate mucosal immune responses. The resulting IgG titers data is shown in FIG. 11A and resulting IgA titers data is shown in FIG. 11B. Quadrivalent M2SR and FLUMIST™ Quadrivalent elicited both IgG and IgA titers against all test antigens. Mice immunized with monovalent BM2SR-Vic and BM2SR-Yam exhibited IgG and IgA titers against both B-Vic and B-Yam HA antigen, but not against H1 or H3 HA antigens. IgG titers against all four antigens were elevated in groups that were immunized with FLUZONE™ Quadrivalent and FLUZONE™ High Dose vaccine, however, no IgA antibody titer was detected to any antigen. These data indicate that BM2SR vaccines elicit mucosal immune responses comparable to licensed live attenuated influenza vaccine, FLUMIST™ Quadrivalent, whereas licensed intramuscular influenza vaccines do not elicit any mucosal immune responses.

Figure 12:
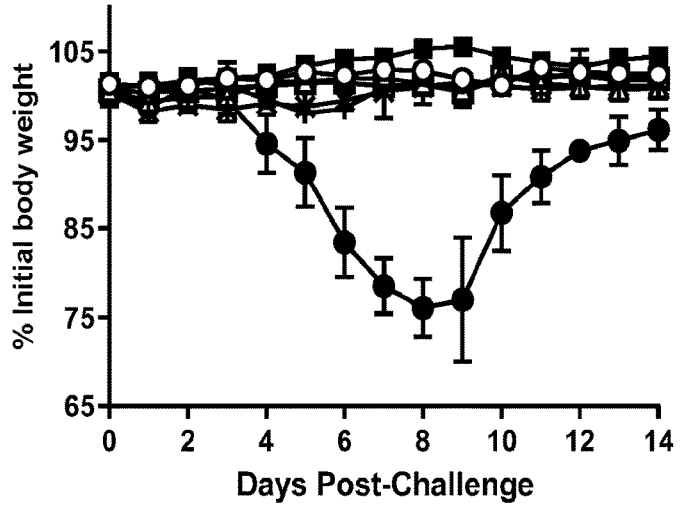
FIG. 12 is a graph depicting mouse percent body weight change after challenge with influenza B/Malaysia/2506/2004 (Vic) of mice immunized with monovalent BM2SR-Vic, monovalent BM2SR-Yam, quadrivalent M2SR, FLU-MIST™ Quadrivalent, FLUZONE™ Quadrivalent, FLUZONE™ High Dose, or SPG (control) versus time (days post-challenge).

Mice were challenged with a lethal dose of influenza B/Malaysia/2506/2004 (Vic) 6 weeks after the boost immunization. Four out of eight mice that were mock immunized with SPG control succumbed to infection by day 10 post-challenge, while all vaccine groups survived. The resulting body weight change after challenge is shown in FIG. 12. Mice who received monovalent BM2SRs, quadrivalent M2SR and licensed vaccines remained healthy with no body weight loss whereas surviving mock immunized mice lost −25% of their body weight. No challenge virus was detected in lungs on day 3 post-challenge in the vaccinated groups except for the FLUZONE™ Quadrivalent (Table 7). The BM2SR-Yam provided protection against lethal infection with a drifted influenza virus B/Malaysia, Victoria lineage. No infectious virus was detected in the lungs of BM2SR-Vic or BM2SR-Yam immunized mice or in any multivalent vaccine containing one or more BM2SR components (Table 7). Infectious virus was detected in lungs of the naïve mock immunized mice. Virus was also detected in the nasal turbinates post-challenge. The BM2SR groups (monovalent, bivalent, trivalent or quadrivalent) had >2 logs less virus in the nasal turbinates than the mock immunized mice indicating that intranasally administered vaccine protects against challenge virus better than the intramuscular vaccines (FLUZONE™ Quadrivalent and High Dose) as shown in Table 7. Furthermore, BM2SR-Yam (as monovalent or formulated with H1N1 or H3N2) provides superior protection against Victoria lineage challenge than FLUZONE™ High Dose (containing Yam) or FLUZONE™ Quadrivalent (containing both Vic and Yam).

These data indicate that the intranasally administered BM2SR vaccine provides better protection against challenge in mice than the intramuscularly administered licensed inactivated vaccines.

TABLE 7

Virus Titers in Mouse Organs After Influenza B/Malaysia/2506/2004 (Vic)

| Vaccine | Virus Titers[a] in | |
| | Lungs | NT |
| --- | --- | --- |
| BM2SR-Vic | —[b] | 4.96 |
| BM2SR-Yam | — | 4.66 |
| BM2SR Bi | — | 3.78 |
| M2SR Tri-Vic | — | 5.30 |
| M2SR Tri-Yam | — | 4.71 |
| BM2SR Tri-H1N1 | — | 2.89 |
| BM2SR Tri-H3N2 | — | 2.88 |
| Quadrivalent M2SR | — | 2.52 |
| FLUMIST ™ Quadrivalent | — | — |
| FLUZONE ™ Quadrivalent | 5.16 | 6.46 |
| FLUZONE ™ High Dose | — | 5.94 |
| Mock | 6.87 | 7.27 |

[a]Organs were collected from 3 mice per group on day 3 post-challenge. Organs were homogenized in 1 mL of 0.3% BSA-MEM, and titrated in MDCK cells. Titers are shown in log PFU/g, average.
[b]—: Below detection limit 1 PFU/0.1 mL Example 12

This example demonstrates that BM2SR virus manufacturing is scalable in the BM2Vero cells used for production.

BM2Vero cells (Vero cells that stably express influenza B BM2 protein) were cultured in humidified incubators at 37° C. at 5% $CO_2$ atmosphere using OptiVero medium (InVitria, Aurora, CO). Approximately 242 million cells in a CELL-STACK™ culture chamber—5 Chamber (CS5; Corning, Corning, NY), 2-4 culture chambers per lot, were infected in OptiVero medium with either a BM2SR-Vic virus encoding the HA and NA genes of Influenza B/Colorado/06/2017 (Vic) or a BM2SR-Yam virus encoding the HA and NA genes of Influenza B/California/12/2015 (Yam) at multiplicity of infection (MOI) of 0.01. After 2-3 days at 35° C., 5% $CO_2$, when the HA titer of the supernatant was at least 32 HAU/50 µL, the culture medium was harvested, and the cells and cell debris were removed by low speed centrifugation. The supernatant was further clarified and sterilized by vacuum filtration through a 0.2 µM pore PES membrane. The clarified supernatant was then treated with non-specific RNA and DNA nuclease (BENZONASE™ enzonase, 5 units/mL) for 2 hours at 37° C. to digest/hydrolyze residual cellular RNA and DNA. The BENZONASE™ benzonase digested material was then purified by tangential flow filtration (TFF) using a 235 cm² 300 kD MWCO Modified Polyethersulfone (mPES) MIDIKROS™ hollow fiber filter module (Repligen, Waltham, MA). The material was concentrated 10 to 20-fold. Then the contaminating host cell proteins (HCP) and residual DNA fragments were removed by diafiltration using at least 15 column volumes SPG. The purified virus in SPG buffer was further concentrated 10 to 100-fold by ultracentrifugation at 25,000 rpm through a 25% sucrose phosphate buffered saline (PBS) cushion. Resultant virus pellets were resuspended in SPG, aliquoted and then flash frozen in liquid N2 followed by storage at −80° C.

The sequence homology of concentrated and purified BM2SR-Vic and BM2SR-Yam genes were compared against those of the reference sequences of the virus seed stock. Viral RNA extracted from the purified viruses was subjected to RT-PCR to generate cDNA followed by Sanger sequencing. Analyses of ORFs encoded by the 8 viral segments indicated that all segments had 100% nucleotide sequence identity to the reference.

The infectious titer of concentrated and purified BM2SR-Vic and BM2SR-Yam viruses was determined by the 50% tissue culture infectious dose ($TCID_{50}$) assay by at least three independent measurements using BM2CK cells (MDCK cells that stably express influenza B BM2). In the procedure, serial dilutions of the vaccine sample were applied to replicate BM2CK cells in 96 well plates and cultured 4 days at 35° C. at 5% $CO_2$ atmosphere. At 4 days post-inoculation, the cell monolayers were visually examined and scored for CPE. The titer of the virus was calculated using the Reed and Muench method and expressed as the $TCID_{50}$/mL. Additionally, HA activity were tested in aliquots of each well supernatant to verify the virus titer determined by CPE. As shown in Table 8, after concentration and purification, BM2SR viruses consistently reached a high titer of over $10^{8.6}$ $TCID_{50}$/mL.

TABLE 8

| | | | | |
|---|---|---|---|---|
| | Virus Titer after Concentration and Purification | | | |
| Lot # | Virus Culture Scale | Beginning Sample Volume | End Sample Volume | Mean Virus Titer ± s.d. (Log $TCID_{50}$/mL) |
| 19E08MM129-041 (B/Co) | 2 CS5 | 1.5 L | 59 mL | 8.68 ± 0.39 |
| 19E31MM129-072 (B/Ca) | 4 CS5 | 3.1 L | 11 mL | 8.72 ± 0.30 |

To confirm that the BM2SR vaccine viruses maintained a replication-deficient phenotype after concentration and purification, the existence of any replicating virus was evaluated by three serial passages of the test article in MDCK cells which are permissive for wild-type influenza viruses but non-permissive for BM2SR virus. In the first round of infection, test virus was serially diluted and inoculated onto the cell monolayer. Infected cells were then cultured for 4 days at 35° C. at 5% $CO_2$ atmosphere. Infected cell culture supernatant was then transferred to a fresh MDCK monolayer and incubated for 4 days at 35° C. at 5% $CO_2$ atmosphere. For the third and final round of passage, this infected cell culture media was transferred to another fresh MDCK monolayer and incubated for an additional 4 days at 35° C. at 5% $CO_2$ atmosphere. MDCK cells were observed for CPEs after every 4-day 35° C. culture and HA activity in culture supernatants were determined to confirm existence of progeny virions. For each round of infection, a previous lot of replication-deficient reference virus, B/California/12/2015 BM2SR was tested as a positive control. Negative control inoculum was media only. The results indicated that the controls performed as expected, and that no infectious progeny were detected after inoculation of normal cells with any of the four test articles. Thus, the BM2SR vaccine virus preparations were demonstrated to be replication incompetent, not capable of replication.

Sterility of the vaccine preparations was verified by a procedure based upon WHO specifications for pharmaceutical preparations. Vaccine preparations were inoculated under aseptic conditions into three types of liquid medium, Luria-Bertani broth (LB), tryptic soy broth (TSB), and thioglycolate medium (TGM). Cultures were grown at 37° C. (LB and TSB) and at ambient temperature (TGM). The cultures were grown for 14 days and then examined visually for microbial growth. All of the preparations tested were negative for microbial growth in all growth conditions.

Example 13

This example demonstrates that the BM2SR backbone is attenuated, does not shed, and is not transmitted in the ferret model.

The M2SR virus is a recombinant influenza A virus that does not express a functional M2 protein, encoding, for example, the HA and NA genes of Influenza A/Brisbane/10/2007-like A/Uruguay/716/2007 (H3N2) or A/California/07/2009 (H1N1pdm). The BM2SR virus is a recombinant influenza B virus that does not express a functional BM2 protein encoding the HA and NA of B/Brisbane/60/2008 (Victoria) or B/Wisconsin/01/2010 (Yamagata), for example. The Quadrivalent M2SR, also referred to herein as M2SR Quad, is composed of 2 M2SR and 2 BM2SR viruses that encode for A/H1N1, A/H3N2, B/Victoria, B/Yamagata HA and NA.

Animals and Animal Care. Male ferrets purchased from Triple F Farms were placed in the study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages were cleaned and sanitized prior to animal receipt, in accordance with accepted animal care practices and relevant standard operating procedures. Certified Teklad Global Ferret Diet #2072 (Teklad Diets, Madison, WI) and water were provided ad libitum and was refreshed at least three time per week. Fluorescent lighting in the animal rooms were maintained on a 12-hr light/dark cycle. Animal room temperature and relative humidity were within respective protocol limits and ranged from 20.0 to 25.0° C. and 30 to 63%, respectively, during the study.

Animal Quarantine and Randomization. The ferrets were held in quarantine for seven days prior to randomization and observed daily. Based on daily observations indicating general good health of the animals, the ferrets were released from quarantine for randomization and testing. Following quarantine, ferrets were weighed and assigned to treatment groups using a computerized randomization procedure based on body weights that produced similar group mean values (TOXDATA™ version 2.1.E.11 (PDS Pathology Data Systems, Inc., Basel, Switzerland)). Within a group, all body weights were within 20% of their mean. Animals selected for the study received a permanent identification number by ear tag and transponder and individual cage cards also identified the study animals by individual numbers and group. The identifying numbers assigned were unique within the study.

Pre-study Animal Procedures. All animal procedures were performed in an animal biosafety level-2 facility in accordance with the protocols approved by the animal care and use committee at IIT Research Institute. Prior to inoculation, ferrets were monitored for 3 days to measure body weight and establish baseline body temperatures. Temperature readings were recorded daily through a transponder (BioMedic data systems, Seaford, DE) implanted subcutaneously in each ferret. Blood was collected prior to study initiation, and serum was tested for influenza antibodies. Pre-vaccination serum samples were treated with receptor destroying enzyme (RDE) to remove nonspecific inhibitors, then serimore than 2.8% body weight. All 6 ferrets were euthanized and virus loads in the organs were titrated. As shown in Table 9, wild-type influenza B/Brisbane/60/2008 (Vic) was detected in the upper respiratory tract including nasal turbinates and trachea, and in brain. No virus was detected in any organs from ferrets inoculated with BM2SR virus

TABLE 9

| | | Virus Titer in Ferret Organs on Day 3 Post-inoculation | | | | | | | | | |
|---|---|---|---|---|---|---|---|---|---|---|---|
| | | Organ Titers | | | | | | | | | |
| Group | Animal Number | Nasal Turbinate | Trachea | Lung | Kidney | Spleen | Brain | Olfactory Bulb | Liver | Small Intestine | Large Intestine |
| Group 1 | F3128 | < | < | < | < | < | < | < | < | < | < |
| BM2SR- | F3129 | < | < | < | < | < | < | < | < | < | < |
| CO/06 | F3130 | < | < | < | < | < | < | < | < | < | < |
| Group 2 | F3140 | 4.25 | 2.75 | < | < | < | < | < | < | < | 2.5 |
| WT B/ | F3141 | 4.25 | < | < | < | < | < | < | < | < | < |
| Bris/60/08 | F3143 | 3.75 | 2.25 | < | < | < | 3.00 | < | < | < | < |

$\leq$below the assay limit of detection of 1.5 $TCID_{50}log_{10}/mL$ ally diluted, tested against a defined amount of influenza virus A/California/07/2009 (H1N1pdm), A/Switzerland/9715293/2013 (H3N2), B/Brisbane/60/2008 (Victoria Lineage) and B/Wisconsin/01/2010 (Yamagata Lineage) and mixed with 0.5% turkey red blood cells or 0.75-1.0% guinea pig red blood cells. Antibody titers were defined by the lowest serum dilution causing inhibition of red blood cell agglutination. Only ferrets with HAI (hemagglutination inhibition) titers less than 40 were considered seronegative and used in this study. Study animals were randomized and divided into groups as outlined below.

To assess the attenuation of BM2SR vaccine virus, a group of 3 ferrets were anesthetized and inoculated intranasally with a single dose of $1\times10^{8.2}$ $TCID_{50}$ of B/CO/06/2017 (Vic) BM2SR virus on Study Day 0. A control group (3 ferrets) were inoculated with a single target dose of $1\times10^{7.4}$ $TCID_{50}$ of wildtype B/Brisbane/60/2008 (Vic) virus. Following exposure on Study Day 0, body weights were recorded once daily, and temperature readings monitored for changes in body temperature six hours after exposure and then once daily. Survival checks were recorded twice daily. On Study Day 3, the animals (3 animals per group) were euthanized and the following tissue samples were collected: nasal turbinate, trachea, lung, kidneys, olfactory bulbs, brains, livers, spleens and intestines. One part of the collected samples were fixed with buffered neutral formalin for histological evaluation and the other part of the samples were stored at $\leq-65°$ C. for virus titration. Tissues harvested for titers included: right nasal turbinates, upper ⅓ of trachea, right cranial lung lobe (if it was of sufficient size) or a lung lobe with gross lesions (if only one lobe had lesions, the lobe was processed for histology and viral titers were determined from any other lobe. If there were lesions in multiple lobes, then one lobe was harvested for virus titers and the other for histology), right kidney, right olfactory bulb, right brain, right lateral lobe of liver, right half of spleen (end of spleen you see on opening the abdominal cavity), small intestine and large intestine.

Although one ferret inoculated with $1\times10^{7.4}$ $TCID_{50}$ of wild-type influenza B/Brisbane/60/2008 (Vic) had an elevated body temperature (2.2° C.) on day 1 post-inoculation, the other 2 ferrets inoculated with the wild-type virus together with the 3 ferrets inoculated with $1\times10^{8.2}$ $TCID_{50}$ of B/CO/06/2017 (Vic) BM2SR virus did not have fevers for 3 days post-dosing. No ferrets used in the study lost or gained To assess the possibility of BM2SR transmission in the ferret model, naïve donor ferrets were inoculated intranasally with Influenza B/CO/06/2017 (Vic) BM2SR vaccine at a dose level of $1\times10^{8.2}$ $TCID_{50}$ or control wild-type Influenza B/Brisbane/60/2008 (Vic) virus at a dosage of $1\times10^{7.4}$ $TCID_{50}$. After 24 hours, each donor ferret was placed in the same wire cage (dual housed) with 1 naïve ferret (direct contact). An additional naïve ferret (aerosol contact) was placed in a separate adjacent wire cage (single housed) within the transmission chamber, separated from the donor's cage by a distance of 10-12 cm. The distance prevented physical contact between the aerosol contact and the infected and direct contacts, allowing only air and the passage of respiratory droplets to be shared between the ferrets. Ferret body temperatures, weights, and clinical symptoms were monitored daily for 7 days post-inoculation. Nasal washes were collected from all inoculated donor ferrets on days 1, 3, 5, 7, 9 and from all contact ferrets on days 2, 4, 6, 8, 10. Nasal washes and serum were collected from all ferrets on day 14.

No virus was detected in nasal washes from three BM2SR vaccine virus donor ferrets and their direct and aerosol contact ferrets at any time-points (FIG. 13A). No ferrets in the BM2SR vaccine virus group had fevers, lost weight or showed any clinical symptoms. Wild-type Influenza B/Bris/60/2008 was detected in nasal washes from wild-type virus donor ferrets on days 1, 3, and 5 post-inoculation (FIG. 13B). Although no ferrets showed changes in body temperature, weight, or clinical symptoms, all direct and aerosol contact ferrets of the wild-type virus donor ferrets were infected and shed virus.

These data indicate that the test setting was appropriate, the virus that was replicable and transmissible was proved its replication and transmissibility. In the same test setting, BM2SR virus did not replicate in ferrets and was not detected in the direct and aerosol contact animals, indicating that the BM2SR virus is highly attenuated and does not replicate in the ferrets, thus it is not transmissible. BM2SR remains attenuated in the ferret model, with BM2SR inoculated ferrets exhibiting no clinical signs of illness and no viral replication in the respiratory track or other organs. Additionally, BM2SR was not detected in direct or aerosol contact animals, indicating that BM2SR is not transmissible.

Example 14

This example demonstrates that immune responses elicited by trivalent M2SR, also referred to herein as M2SR Tri-Yam, and Quadrivalent M2SR, also referred to herein as M2SR Quad, vaccines provide protective efficacy against drifted challenge virus in both naïve and preimmune ferret models.

Animal care, quarantine, randomization, and pre-study procedures were as outlined in Example 13.

(H3N2), B/California/12/2015 (Yam), and B/Colorado/06/2017 (Vic) (FIG. 14A-D and FIG. 15A-D) to demonstrate functional activity of the antibodies. Vaccination with M2SR Tri-Yam containing BM2SR-Yam elicited anti-influenza HAI and neutralizing antibodies against all vaccine components in naïve animals. M2SR Tri-Yam induced cross-lineage influenza B antibody production (against B Victoria) in naïve animals that were boosted after the second dose. Animals who received M2SR Quad as a single dose or in two consecutive doses produced HAI and neutralizing anti-

TABLE 10

| | | | | | | |
|---|---|---|---|---|---|---|
| | | | Experimental Design | | | |
| Group | # Ferrets | Preinfection Group[1] | Vaccine Day 30 | Readouts | Challenge Day 72 | Readouts post-challenge |
| 1 | 10 | WT[2] infected | M2SR Quad | Serum collection | Heterologous | Weight loss, |
| 2 | 10 | (IN) | FLUMIST ™ Quad | days −8 to −3, 28, 37, 51, 65. | Influenza B (Vic) | clinical scores. Nasal wash days 1, |
| 3 | 10 | | FLUZONE ™ Quad | PBMC collection days 28, 37. | Virus | 3, 5, and 7 for virus titer. |
| 4 | 10 | | PBS | | | Viral load in |
| 5 | 10 | Naïve (PBS) | M2SR Quad | | | respiratory tract |
| 6 | 10 | | FLUMIST ™ Quad | | | organs (nasal turbinates, |
| 7 | 10 | | FLUZONE ™ Quad | | | trachea, lungs) on day 3 |
| 8 | 10 | | PBS | | | (N = 4/group)[3]. |
| 9 | 10 | | M2SR Tri-Yam | | | |
| 10 | 10 | M2SR Tri-Yam | M2SR Tri-Yam | | | |
| 11 | 10 | M2SR Quad | M2SR Quad | | | |
| 12 | 10 | FLUMIST ™ Quad | FLUMIST ™ Quad | | | |
| 13 | 10 | FLUZONE ™ Quad | FLUZONE ™ Quad | | | |

[1]Rest 30 days after pre-infection
[2]A/California/07/2009 (H1N1pdm) and B/Wisconsin/01/2010 (Yamagata) wild-type viruses at a dose of 1 × 10$^3$ per virus
[3]No nasal wash collection from ferrets designated for organ harvest The experimental design is shown in Table 10. On Study Day 0, ferrets were either pre-infected with wildtype viruses or inoculated by intranasal administration of M2SR Tri-Yam, M2SR Quad, FLUMIST™ Quadrivalent, also referred to herein as FLUMIST™ Quad, PBS or by intramuscular injection of FLUZONE™ Quadrivalent, also referred to herein as FLUZONE™ Quad. On Study Day 30, ferrets were vaccinated by intranasal administration of M2SR Tri-Yam, M2SR Quad, FLUMIST™ Quad and PBS or by intramuscular injection of FLUZONE™ Quad. Strain components for each vaccine are shown in Table 6. Following vaccination/exposure, sera were collected from all animals on Study Days −8 to −3, 28, 37, 51, and 65. Additionally, peripheral blood mononuclear cells (PBMCs) were collected from all animals on Study Days 28 and 37. Ferrets were challenged with B/Brisbane/60/2008 (B Victoria lineage) on Study Day 72. Ferret body weight, body temperature and clinical symptoms were monitored for fourteen days post-challenge. Nasal washes were collected from all challenged ferrets (except those assigned for organ collection) on post-challenge days 1, 3, 5 and 7 (Study days 73, 75, 77 and 79) and samples were stored at ≤−65° C. for virus titration. On Study Day 75, four ferrets from each group were euthanized and necropsied. Nasal turbinates, trachea and lungs were collected for viral titer analysis. On study day 86, all remaining animals were terminally bled for serum recovery.

Serum HAI and PRNT (plaque reduction neutralization test) titers were measured against influenza A/Montana/50/2016 (H1N1), A/Singapore/INFIMH-16-0019/2016 bodies to all 4 strain components. Furthermore, the magnitude of antibody production from M2SR Quad was comparable to that of M2SR Tri-Yam, indicating that the addition of the second BM2SR component had no effect on vaccine performance and that the M2SR Quad formulation does not display strain interference (FIG. 14A-D and FIG. 15A-D).

M2SR Quad and FLUMIST™ Quad each elicited HAI and neutralizing antibodies in naïve animals, while FLU-ZONE™ Quad vaccine was not able to induce corresponding antibodies even after two consecutive doses. However, preimmune animals vaccinated with FLUMIST™ Quad had lower HAI and neutralizing antibody production against several strains when compared to M2SR Quad. Antibody production was also inhibited in animals who received two doses of FLUMIST™ Quad as compared to those who received two doses of M2SR Quad (FIG. 14A-D and FIG. 15A-D). These results indicate that M2SR Quad is not susceptible to pre-existing influenza immunity.

As a marker of the cellular immune response, influenza-specific IFN-γ secretion from whole blood PBMCs was measured by ferret-specific Enzyme-linked Immunospot (ELISpot). In preimmune animals who received M2SR Quad vaccination, 9 out of 10 ferrets exhibited increased cellular immune responses following H3N2 influenza virus stimulation as compared to only 6/10 for FLUMIST™ Quad and 2/10 for FLUZONE™ Quad (FIG. 18A). Similar responses were seen following stimulation with H1N1 HA peptides, with M2SR Quad demonstrating increased cellular immune responses from 10 out of 10 animals, while the frequency of increases for FLUMIST™ Quad and FLU-ZONE™ Quad were much lower (6/10 and 2/10 respectively, FIG. 18B). These results indicate that M2SR induces strong T cell responses in addition to antibody responses.

After influenza B-Vic challenge, naïve animals who received mock treatment displayed −5-6% transient body weight loss and increases in body temperature. Naïve ferrets who received a single dose of FLUZONE™ Quad were comparable to mock-treated animals, displaying −4-5% transient body weight loss, while M2SR Tri-Yam and M2SR Quad groups did not have any weight loss. Among the preimmune vaccine groups, the FLUZONE™ Quad ferrets displayed weight loss and temperature increases similar to the mock group whereas the Quad M2SR group did not have any weight loss or increases in body temperature (FIG. 19).

Nasal washes were harvested on days 1, 3, 5, and 7 post-challenge and titrated by $TCID_{50}$ assay in MDCK cells (FIG. 17). M2SR Tri-Yam provided cross lineage influenza B protection to naive ferrets, exhibiting decreased viral titers on all sampling days and reaching undetectable levels before control ferrets. Viral titers in naïve ferrets who received M2SR Quad were comparable or slightly lower than M2SR Tri-Yam, again demonstrating a lack of interference in the M2SR Quad formulation. In preimmune ferrets, M2SR Quad and FLUMIST™ Quad both controlled challenge virus replication quickly, with only low levels detected on day 3 post-challenge. In contrast, ferrets that received FLU-ZONE™ Quad shed virus at high levels until day 5 post-challenge. Decreased levels of virus in nasal washes were also seen in ferrets that received two doses of M2SR Quad or FLUMIST™ Quad, while titers in ferrets who received two doses of FLUZONE™ Quad remained high 5 days post-challenge (FIG. 17).

Respiratory organs (nasal turbinate, trachea, and lungs) were harvested on day 3 post-infection from 4 ferrets per group and virus titers were measured by plaque assay in MDCK cells. Influenza B challenge virus was not recovered from the lungs or tracheas of any ferret in any vaccination group. M2SR Tri-Yam provided cross lineage influenza B protection to naive ferrets, demonstrating decreased virus titer in nasal turbinates, especially after two consecutive doses. Viral titers in naïve ferrets who received M2SR Quad were further reduced. In preimmune ferrets, M2SR and FLUMIST™ Quad vaccination resulted in no detectable viral titer on day 3 post-challenge. Interestingly, high neutralization antibody titers seen in the HAI and PRNT serum analysis of preimmune ferrets vaccinated with FLUZONE™ Quad did not prevent challenge virus growth in nasal turbinates. Additionally, while virus titers remained undetectable in ferrets who received two doses of M2SR Quad or FLUMIST™ Quad, ferrets who received two doses of FLUZONE™ Quad were not protected.

This example demonstrated that intranasal administration of the M2SR Tri-Yam or M2SR Quad formulations is not associated with any vaccine-related adverse events in the ferret model (e.g., elevated body temperature, loss of weight, or clinical signs). M2SR Tri-Yam vaccine induced cross-lineage influenza B antibody production and post-challenge protection in naïve animals. HAI and neutralizing responses to all 4 strain components remained high in the M2SR Quad ferrets demonstrating no interference in the M2SR multivalent formulation. Furthermore, unlike licensed vaccine FLU-MIST™ Quad, M2SR Quad antibody production was not reduced in preimmune animals. Cellular immune responses following influenza-specific stimulation were higher and more frequent in ferrets vaccinated with M2SR Quad, further distinguishing it from the current licensed vaccines FLUMIST™ Quad and FLUZONE™ Quad.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Sequencing conventions are based on DNA referring to the four nucleotides: adenine (a), guanine (G), cytosine (C), and thymine (T). When referring to RNA or influenza virus, T means uracil (U).

The invention claimed is:

1. An influenza virus comprising PA, NP, and NS gene segments, wherein
   (a) the PA gene segment comprises a thymine at nucleotide position 2272;
   (b) the NP gene segment encodes a NP protein having an amino acid sequence comprising selected amino acids, wherein the selected amino acids comprise a serine at position 40, an asparagine or glycine at position 161, a threonine at position 204, and optionally a valine at position 93; and
   (c) the NS gene segment comprises a guanine at nucleotide position 39, and the NS gene segment encodes an NS1 protein having an amino acid sequence comprising selected amino acids, wherein the selected amino acids comprise a glutamine at position 176.

2. The influenza virus of claim 1, wherein the PA gene segment has a nucleotide sequence represented by SEQ ID NO: 10.

3. The influenza virus of claim 1, wherein the NP gene segment has a nucleotide sequence represented by SEQ ID NO: 11.

4. The influenza virus of claim 1, wherein the PA gene segment encodes a PA protein having an amino acid sequence of SEQ ID NO: 15.

5. The influenza virus of claim 1, wherein the NP gene segment encodes an NP protein having an amino acid sequence of SEQ ID NO: 16.

6. The influenza virus of claim 1, wherein the NS gene segment has a nucleotide sequence represented by SEQ ID NO: 12.

7. The influenza virus of claim 1, wherein the NS gene segment encodes an NS1 protein having an amino acid sequence of SEQ ID NO: 17.

8. The influenza virus of claim 1, wherein the selected amino acids are conserved in at least one of the NP and NS proteins after at least ten serial passages in a Vero cell line.

9. The influenza virus of claim 1, wherein the selected amino acids are conserved in at least one of the NP and NS proteins after at least ten serial passages in a Vero cell line that stably expresses the BM2 ion channel protein of influenza B virus.

10. The influenza virus of claim 1 wherein the influenza virus is a recombinant influenza virus.

11. The influenza virus of claim 1, wherein the virus further comprises a PB gene segment.

12. The influenza virus of claim 1, wherein the virus further comprises a NA gene segment and an HA gene segment.

13. The influenza virus of claim 12, wherein the HA gene segment encodes an HA protein having an amino acid sequence comprising at least one amino acid mutation in HA2.

14. The influenza virus of claim 13, wherein the at least one amino acid mutation in HA2 is a glutamic acid at position 61.

15. The influenza virus of claim 13, wherein the at least one amino acid mutation in HA2 is a glutamic acid at position 112.

16. The influenza virus of claim 1, wherein the PA, NP, and NS gene segments are derived from a single influenza strain.

17. The influenza virus of claim 16, wherein the HA gene segment is derived from an influenza strain different from the single influenza strain from which the PA, NP, and NS gene segments are derived.

18. The influenza virus of claim 16, wherein the NA gene segment is derived from an influenza strain different from the single influenza strain from which the PA, NP, and NS gene segments are derived.

19. The influenza virus of claim 1, further comprising a mutant M gene segment.

20. The influenza virus of claim 19, wherein the influenza virus does not encode a functional BM2 protein.

21. The influenza virus of claim 1, wherein the virus is capable of replication in human cells.

22. The influenza virus of claim 1, wherein the virus has enhanced growth as compared to an influenza virus that is the same except without the selected amino acids in Vero cells under the same conditions.

23. A pharmaceutical formulation comprising the influenza virus of claim 1.

24. The pharmaceutical formulation of claim 23, wherein the pharmaceutical formulation is a vaccine.

25. The pharmaceutical formulation of claim 24, wherein the vaccine is formulated as a monovalent vaccine, a bivalent vaccine, a trivalent vaccine, or a quadrivalent vaccine.

26. A method of eliciting an immune response in a mammal, the method comprising administering the influenza virus of claim 1 to the mammal, thereby eliciting an immune response to the influenza virus in the mammal.

27. The method of claim 26, wherein the mammal is a human.

28. A method of generating the influenza virus of claim 1, the method comprising serially passaging in influenza virus in a Vero cell line.

\* \* \* \* \*